US005723761A

United States Patent [19]
Voelker et al.

[11] Patent Number: 5,723,761
[45] Date of Patent: Mar. 3, 1998

[54] PLANT ACYL-ACP THIOESTERASE SEQUENCES

[75] Inventors: Toni A. Voelker, Davis; Ling Yuan, Vacaville; Jean Kridl; Deborah Hawkins, both of Davis; Aubrey Jones, Woodland, all of Calif.

[73] Assignee: Calgene, Inc., Davis, Calif.

[21] Appl. No.: 464,523

[22] Filed: Jun. 2, 1995

Related U.S. Application Data

[63] Continuation-in-part of PCT/US94/13131, Nov. 10, 1994, continuation-in-part of Ser. No. 261,695, Jun. 16, 1994, abandoned, and Ser. No. 152,004, Nov. 10, 1993, abandoned.

[51] Int. Cl.$^6$ .................. A01H 5/00; A01H 15/10; C12N 5/14; C12N 15/29; C12N 15/52; C12N 15/82

[52] U.S. Cl. .................. 800/205; 426/607; 435/172.3; 435/320.1; 435/419; 536/23.2; 536/23.6; 800/205; 800/255; 800/DIG. 9; 800/DIG. 17; 800/DIG. 59; 800/DIG. 65; 800/DIG. 69

[58] Field of Search .................. 435/320.1, 240.4, 435/172.3, 419; 536/23.2, 23.6, 24.1; 800/205, 255, DIG. 17, DIG. 9, DIG. 59, DIG. 65, DIG. 69; 426/601, 607

[56] References Cited

FOREIGN PATENT DOCUMENTS

| | | |
|---|---|---|
| WO 91/13972 | 9/1991 | WIPO . |
| 91 16421 | 10/1991 | WIPO . |
| WO 92/03919 | 3/1992 | WIPO . |
| WO 92/11373 | 7/1992 | WIPO . |
| WO 92/20236 | 11/1992 | WIPO . |
| WO 93/18158 | 9/1993 | WIPO . |
| 94 10288 | 5/1994 | WIPO . |

OTHER PUBLICATIONS

Yadav, et al., "Genetic Manipulation to Alter Fatty Acid Profiles of Oilseed Crops", *Biochemistry and Molecular Biology of Membrane and Storage Lipids of Plants* pp. 60–66 (1993).

Kridl, et al. "Progress in Expression of Genes Controlling Fatty Acid Biosynthesis to Alter Oil Composition and Content in Transgenic Rapeseed" *CRC Press*, Control of Gene Expression Chapter 30 (1993): 481–498.

Davies, et al. "Developmental Induction, Purification and Further Characterization of 12:0-ACP Thioesterase from Immature Cotyledons of *Umbelluria californica*" *Archives of Biochemistry and Biophysics* (1991) 290: No. 1, Oct.: 37–45.

Knutzon, et al. "Modification of Brassica Seed Oil by Antisense Expression of a Stearoyl–Acyl Protein Desaturase Gene" *Plant Biology* (1992) 89: 2624–2628.

Voelker, et al. "Fatty Acid Biosynthesis Redirected to Medium Chains in Transgenic Oilseed Plants" *Science* (1992) 257: 72–74.

Hernqvist, et al., "The Polymorphism of Low Erucic Rapeseed Oil with High Content of Palmitic Acid," *Fett Wissenschaft technologie* vol. 89, No. 5, (1987).

Bafor, et al., "Properties of the Glycerol Acylating Enzymes in Microsomal Preparations from the Developing Seeds of Safflower (*Carthamus tinctorius*) and Turnip Rape (*Brassica campestris*) and their Ability to Assemble Cocoa–butter Type Fats," *Journal of the American Oil Chemists Society*, vol. 67, No. 4, Apr. 1990.

Knauf, et al., "The Application of Genetic Engineering to Oilseed Crops", *Trends in Biotechnology* vol. 5, No. 2, Feb. 1987.

Persson, et al., "High Palimitic Acid Content in Summer Turnip Rape (*Brassica campestris* var annua L.)" Database CAB AN 86:25219 (from Cruciferae Newsletter No. 10, p. 137, (1985).

Persson, et al., "Increased Palmitic Acid Content in Summer Turnip Rape" Database CAB AN 84:62613 (from Sveriges Utsadesforenings Tidskrift vol. 93, No. 4:323–329 (1983).

Knutzon, et al. (Apr. 1992) Proc. Natl. Acad. Sci. USA 89: 2624–2628.

Hernquist, et al. (1989) Fat Science Technology #5: 190–193.

*Primary Examiner*—Douglas W. Robinson
*Assistant Examiner*—Amy J. Nelson
*Attorney, Agent, or Firm*—Donna E. Scherer; Carl J. Schwedler

[57] ABSTRACT

This invention relates to plant thioesterases, specifically plant acyl-ACP thioesterases having substantial activity on palmitoyl-ACP substrates. DNA constructs useful for the expression of a plant palmitoyl-ACP thioesterase in a plant seed cell are described. Such constructs will contain a DNA sequence encoding the plant palmitoyl-ACP thioesterase of interest under the control of regulatory elements capable of preferentially directing the expression of the plant palmitoyl-ACP thioesterase in seed tissue, as compared with other plant tissues, when such a construct is expressed in a transgenic plant. This invention also relates to methods of using a DNA sequence encoding a plant palmitoyl-ACP thioesterase for the modification of the proportion of free fatty acids produced in a plant seed cell. Plant palmitoyl-ACP thioesterase sequences exemplified herein include Cuphea, leek, mango and elm. Transgenic plants having increased levels of C16:0 fatty acids in their seeds as the result of expression of these palmitoyl-ACP thioesterase sequences are also provided.

42 Claims, 63 Drawing Sheets

```
CCAACCCCAA CTCCAACTCC GAACTGATGT TGGACCATGG CAGCCTCGTA ATTTATGGCA      60

AAACCTAGTG TCATTTACTT TGTCACGGCA CAACCTCGGT CCCATCGACA AAATCAAACA     120

TACACTTTAA ATACTAAGGC AGTCGCACGG CTCCTCGTCT CTGTATCTCT CTCTCACGAT     180

TCTACAGAGA TAACTATATT GCTCCGGGCGA GCCTTTGTTT TTGTTTCAGC TTTACATAGA    240

ACAACAGAAC ATG TCG CAG TTT ACA TGC AAT GTC ACG GAC CAA ATT CAC        289
           Met Ser Gln Phe Thr Cys Asn Val Thr Asp Gln Ile His
            1               5                  10

ATT CGA AAC CAG CCC CAA TGC AGA TTC ATG GGC CTT CCG AAG CCT GTA       337
Ile Arg Asn Gln Pro Gln Cys Arg Phe Met Gly Leu Pro Lys Pro Val
 15                  20                  25

TCC TCT TTT CGC CGA AAC GAT GTC GTT TCT TCT TCC CTT CCG ATT           385
Ser Ser Phe Arg Arg Asn Asp Val Val Ser Ser Ser Leu Pro Ile
 30                  35                  40                 45

CCT AAA CCT CGA AAT CCG GTC AAA ATT CAG GCT GTA GTA TCG GAA CAC       433
Pro Lys Pro Arg Asn Pro Val Lys Ile Gln Ala Val Val Ser Glu His
 50                  55                  60
```

FIG. 1A

```
GGA GGT CCA GCT GTC ACC GAC ACT GGG TCT GGT ACG TTG GCG GAC AGA    481
Gly Gly Pro Ala Val Thr Asp Thr Gly Ser Gly Thr Leu Ala Asp Arg
             65                  70                  75

CTC CGT TTA GGG AGC TTA ACG GAA GAT GGA TTG TCC TAT AAG GAG AAG    529
Leu Arg Leu Gly Ser Leu Thr Glu Asp Gly Leu Ser Tyr Lys Glu Lys
         80                  85                  90

TTT ATA GTG AGA TGT TAT GAG GTT GGG ATT AAC AAA ACT GCC ACG GTT    577
Phe Ile Val Arg Cys Tyr Glu Val Gly Ile Asn Lys Thr Ala Thr Val
     95                 100                 105

GAA ACC ATT GCT AAT CTC CTG CAG GAG GTT GGA TGT AAC CAT GCT CAA    625
Glu Thr Ile Ala Asn Leu Leu Gln Glu Val Gly Cys Asn His Ala Gln
 110                 115                 120                 125

AGT GTT GGA TTT TCA ACG GAT GGA TTT GCA ACA ACC CCC ACC ATG AGA    673
Ser Val Gly Phe Ser Thr Asp Gly Phe Ala Thr Thr Pro Thr Met Arg
                 130                 135                 140

AAA TTC AAT CTT ATA TGG GTG ACG GCT CGG ATG CAT ATT GAA ATC TTA    721
Lys Phe Asn Leu Ile Trp Val Thr Ala Arg Met His Ile Glu Ile Leu
             145                 150                 155
```

FIG. 1B

```
AAA TAT CCA GCT TGG AGT GAT GTG GTT GAA ATC GAA ACA TGG TGT CAT      769
Lys Tyr Pro Ala Trp Ser Asp Val Val Glu Ile Glu Thr Trp Cys His
160                 165                 170

AGT GAA GGC AGA ATT GGA ACT AGA CGT GAT TGG ATT ATA AAA GAC TAT      817
Ser Glu Gly Arg Ile Gly Thr Arg Arg Asp Trp Ile Ile Lys Asp Tyr
    175                 180                 185

GCC ACT GGT CAA GTT ATT GGA AGA GCA ACA AGC AAG TGG GTG ATG ATG      865
Ala Thr Gly Gln Val Ile Gly Arg Ala Thr Ser Lys Trp Val Met Met
190                 195                 200                 205

AAC ACG GTC ACT AGG CGG CTA CAG AAA GCC AGT GAT GAA GTT CGA GAA      913
Asn Thr Val Thr Arg Arg Leu Gln Lys Ala Ser Asp Glu Val Arg Glu
            210                 215                 220

GAA TAT TTA GTT TTC TGT CCA CGA GAA CCC AGA TAC TCT TTT CCA GAG      961
Glu Tyr Leu Val Phe Cys Pro Arg Glu Pro Arg Tyr Ser Phe Pro Glu
225                 230                 235

AAG GAC AAT GCC AGC CTG AGG AAA ATT TCT AAA CTC GAA GAT CCT GCT     1009
Lys Asp Asn Ala Ser Leu Arg Lys Ile Ser Lys Leu Glu Asp Pro Ala
    240                 245                 250
```

FIG. 1C

```
GAG TAT TCC AGG ACA GGG CTT ATG CCT AGG AGA GCT GAT CTT GAC ATG      1057
Glu Tyr Ser Arg Thr Gly Leu Met Pro Arg Arg Ala Asp Leu Asp Met
255                 260                 265

AAC CAG CAC GTT AAC AAT GTT ACC TAC ATT GGA TGG GTT CTA GAG AGC      1105
Asn Gln His Val Asn Asn Val Thr Tyr Ile Gly Trp Val Leu Glu Ser
270                 275                 280                 285

ATG CCT CAA GAT ATC ATT GAC ACT CAC GAA CTG CAA ACG ATC ACC TTA      1153
Met Pro Gln Asp Ile Ile Asp Thr His Glu Leu Gln Thr Ile Thr Leu
        290                 295                 300

GAT TAC AGA CGA GAA TGC CAA CGA GAC ATA GTC GAT TCC CTC ACA          1201
Asp Tyr Arg Arg Glu Cys Gln Arg Asp Ile Val Asp Ser Leu Thr
305                 310                 315

AGT CCT GAA CTG ATC ATC GAG GAT TCT GAT GCA ATT TCA AAT CTT AAA GGA  1249
Ser Pro Glu Leu Ile Ile Glu Asp Ser Asp Ala Ile Ser Asn Leu Lys Gly
320                 325                 330

GCA AAT GGG TCT CCT GCA ACA GGA GAC AAA GAA GAC TAC CGT CAA TTT      1297
Ala Asn Gly Ser Pro Ala Thr Gly Asp Lys Glu Asp Tyr Arg Gln Phe
335                 340                 345
```

FIG. 1D

```
TTG CAC TTG CTG AGA TTG TCA AGC GAT GGC TCT GAA ATA AAC CGA GGT    1345
Leu His Leu Leu Arg Leu Ser Ser Asp Gly Ser Glu Ile Asn Arg Gly
350                 355                 360                 365

CGC ACT GAG TGG AGA AGG AAA CCT GGT AGA TAAGGAAATA GTGTAGTTTA       1395
Arg Thr Glu Trp Arg Arg Lys Pro Gly Arg
                370                 375

CCCCAGTCTC CTCTCTTCAA TGTGTTCGGA AAAGTTGTTT GTTTCTGTTT CTTTTGCCTT   1455

TCATAAGGGG GTTGGCTCC  AAATCTGTGT GTTGTTGGA  ACTTTAGAAT CATCAGTAGA   1515

TTACGAGGCA AATGTGTAGT TTTTTTTCCG GTCGGTCATC CATCAATTGT TGTATCTTTA   1575

CTGTTTGTAA TTTTGTCAGA AGCTTTCGTG TTTATATGTA ATGTTTCTTG TTTGAAAAGT   1635

CCATATGGAA TTAGATTCCT AGTTTTCAGG CTCTGCATTT GGTGTAAGGT TTGGGACTCT   1695

GTTTCGCCAA CATGAAATTT AACATTTGA  AAAAAAAAA  AAAAAAAAAA              1745
```

FIG. 1E

```
GCAGCATCAG GATTAGCAGA TCCAAAATGA AGCAATGGTG TCTTCTTGCC TGACTATTTT         60

TACGACGTTC GGATAATTTA TTCTTGCTTC TCTTCGWCAT TTCTCTGTTT CTCGCCGGTT        120

AAGGTGGTTC CCTCTACATT TTCAAG ATG GCT TCT ACT GCT GCT GCA TGT             173
                              Met Ala Ser Thr Ala Ala Ala Thr Ala Cys
                                1               5

TTT TTT CCA GTT TCT TCT TCA GAT TCT GTT GCA AAG ACC AAG                  221
Phe Phe Pro Val Ser Ser Ser Asp Ser Val Ala Lys Thr Lys
10               15              20              25

AAT ATT GGA TCT GCT AGT TTG GGA GGT ATG AAA GCC AAA TCA TCT TCT          269
Asn Ile Gly Ser Ala Ser Leu Gly Gly Met Lys Ala Lys Ser Ser Ser
         30              35              40

GGG GGT TTG CAG GTT AAG GCC AGT GCC CAA GCG CCT TCC AAA ATA AAT          317
Gly Gly Leu Gln Val Lys Ala Ser Ala Gln Ala Pro Ser Lys Ile Asn
         45              50              55

GGT ACT TCA GTT GGT TTG ACA AAA CCA TCG GAA AGC CTG AAG AAT GAG          365
Gly Thr Ser Val Gly Leu Thr Lys Pro Ser Glu Ser Leu Lys Asn Glu
         60              65              70
```

```
GAT GAG ATG CCT TCA TCT CAC CCA AGG ACT TTT ATT AAC CAA TTA CCC    413
Asp Glu Met Pro Ser Ser His Pro Arg Thr Phe Ile Asn Gln Leu Pro
 75                      80                      85

GAC TGG AGC ATG CTT CTT GCT GCC ATA ACA ACC ATA TTC TTG GCA GCG    461
Asp Trp Ser Met Leu Leu Ala Ala Ile Thr Thr Ile Phe Leu Ala Ala
 90                      95                     100                 105

GAG AAA CAG TGG ATG ATG CTT GAC TGG AAA CCA AGA AGG TCC GAC ATG    509
Glu Lys Gln Trp Met Met Leu Asp Trp Lys Pro Arg Arg Ser Asp Met
                        110                     115                 120

CTT ATT GAT CCA TTT GGT ATT GGG AGG ATT GTT CAG GAT GGT CTG ATA    557
Leu Ile Asp Pro Phe Gly Ile Gly Arg Ile Val Gln Asp Gly Leu Ile
             125                     130                     135

TTC CGA CAA AAT TTT TCA ATT AGA TCC TAT GAG ATA GGT GCT GAT CGT    605
Phe Arg Gln Asn Phe Ser Ile Arg Ser Tyr Glu Ile Gly Ala Asp Arg
         140                     145                     150

ACT GCA TCT ATA GAG ACA TTG ATG AAT CAT TTA CAG GAG ACA GCT CTT    653
Thr Ala Ser Ile Glu Thr Leu Met Asn His Leu Gln Glu Thr Ala Leu
 155                     160                     165
```

```
AAT CAT GTT AAG AGT GCT GGT CTT GGT GAT GGC TTC GGT TCA ACC     701
Asn His Val Lys Ser Ala Gly Leu Gly Asp Gly Phe Gly Ser Thr
170             175                 180                 185

CCA GGG ATG TGC AAG AAT CTG ATA TGG GTG GTT ACC CGA ATG CAG     749
Pro Gly Met Cys Lys Asn Leu Ile Trp Val Val Thr Arg Met Gln
        190                 195                 200

GTT GTA GAT CGT TAT CCT ACC TGG GGT GAT GTT GTT GAG GTA GAT     797
Val Val Asp Arg Tyr Pro Thr Trp Gly Asp Val Val Glu Val Asp
            205                 210                 215

TCT TGG GTT AGT GCA TCG GGA AAG AAT GGT ATG CGC CGT GAT TGG CTT 845
Ser Trp Val Ser Ala Ser Gly Lys Asn Gly Met Arg Arg Asp Trp Leu
        220                 225                 230

GCC CGC GAT AGT AAA ACA GGG GAA ACT TTA ACA AGG GCC TCC AGT GTG 893
Ala Arg Asp Ser Lys Thr Gly Glu Thr Leu Thr Arg Ala Ser Ser Val
    235                 240                 245

TGG GTG ATG ATG AAT AAA CAG ACT AGG AGA TTA TCC AAA ATT CCA GAC 941
Trp Val Met Met Asn Lys Gln Thr Arg Arg Leu Ser Lys Ile Pro Asp
250                 255                 260                 265
```

FIG. 2C

```
GAA AGA GGG GAA ATT GAG CCT TAT TTT GTA AAC TCT GAT CCT GTT      989
Glu Arg Gly Glu Ile Glu Pro Tyr Phe Val Asn Ser Asp Pro Val
                270                 275                 280

GTG GAT GAG GAT GGT AGG AAA TTA CCA AAA CTT GAC GAC AAC ACA GCT 1037
Val Asp Glu Asp Gly Arg Lys Leu Pro Lys Leu Asp Asp Asn Thr Ala
            285                 290                 295

GAT TAT GTT CAC AGA GGT TTA ACT CCT AGA TGG AGT GAT TTA GAT GTC 1085
Asp Tyr Val His Arg Gly Leu Thr Pro Arg Trp Ser Asp Leu Asp Val
300                 305                 310

AAC CAG CAT GTT AAC AAT GTG AAG TAC ATT GGC TGG ATC CTT GAG AGT 1133
Asn Gln His Val Asn Asn Val Lys Tyr Ile Gly Trp Ile Leu Glu Ser
315                 320                 325

GCT CCG CAG GCA ATC CTG GAG AGT CAC GAG CTT GCA TCT ATG ACT TTG 1181
Ala Pro Gln Ala Ile Leu Glu Ser His Glu Leu Ala Ser Met Thr Leu
330                 335                 340                 345

GAG TAT CGG AGG GAG TGT GGG AAG GAC AGT GTG TTA AAG TCT CTT ACT 1229
Glu Tyr Arg Arg Glu Cys Gly Lys Asp Ser Val Leu Lys Ser Leu Thr
350                 355                 360
```

FIG. 2D

```
GCT GTC TCT GGT TCT GAT GTT GGC AAT TTG AGC CAC CTT GGC CGT GTC   1277
Ala Val Ser Gly Ser Asp Val Gly Asn Leu Ser His Leu Gly Arg Val
            365                 370                 375

GAG TGC CAG CAC ATG CTA CAA CTC GAG GAT GGG GCT GAA ATA GTG AGA   1325
Glu Cys Gln His Met Leu Gln Leu Glu Asp Gly Ala Glu Ile Val Arg
        380                 385                 390

GGA AGG ACT GAA TGG AGG CCT AAA TAT GCA AAC AAC TTT GGG AAT GTG   1373
Gly Arg Thr Glu Trp Arg Pro Lys Tyr Ala Asn Asn Phe Gly Asn Val
        395                 400                 405

GGT GAG GTT CCG GCT GAA AGC GCA TAAAACTTGA TCATTGTGGC TAGGAGGCCA   1427
Gly Glu Val Pro Ala Glu Ser Ala
        410                 415

TGGTCACATT GCTTGTGCAG AATCCAATCC TGCTTGTGTT GGATGATTTT TATGCTTCTT   1487

TATATGTATT TACTTGTTTG TCCTACTTTA AGAAAGCTG GAAGTTCAGT GTAATTAGCC   1547

TTGCTGCAGT CTCGAATTCC ACCAATTCAA TTAGCCCTCT TCCCACGGAT   1607

GCAATGCAAA GATGGATGAA TTATATAGAG GGAAATTCTA TGGTTGCTTA ACCTGTTGAG   1667

TTGTTAATTG TTAAGCCCTT TTATTTTCAC CTAAAAAAAA AAAAAAAAAA   1717
```

FIG. 2E

```
C ATG GAT GCA AAA ACA CAT GCT CAA GCT GTT CCA AAA ATA AAT GGA ACA
  Met Asp Ala Lys Thr His Ala Gln Ala Val Pro Lys Ile Asn Gly Thr>

AAG GTC GAT ACA AGG AGA AAT GAT TCT TCA AGA GGG GAG GAC GAG GCT
Lys Val Asp Thr Arg Arg Asn Asp Ser Ser Arg Gly Glu Asp Glu Ala>

ATA TAC ACT ACT TCT TCT GCC CCT AGG ACA TTC TAT AAC CAG TTG CCT
Ile Tyr Thr Thr Ser Ser Ala Pro Arg Thr Phe Tyr Asn Gln Leu Pro>

GAT TGG AGC ATG TTG CTA GCT GCC ATT ACT ACT ATA TTT TTG GCA GCT
Asp Trp Ser Met Leu Leu Ala Ala Ile Thr Thr Ile Phe Leu Ala Ala>

GAG AAG CAA TGG ACT CTT ATT GAT TGG AAG CCT AGG CGA CCT GAT ATG
Glu Lys Gln Trp Thr Leu Ile Asp Trp Lys Pro Arg Arg Pro Asp Met>

CTT TCT GAT GCG TTT GGA CTT GGA AAG ATT GTT CAA GAT GGG CTC GTG
Leu Ser Asp Ala Phe Gly Leu Gly Lys Ile Val Gln Asp Gly Leu Val>

TTT ACT CAG AAT TTT CCT ATA CGA TCC TAT GAG ATA GGG GCA GAT CGG
Phe Thr Gln Asn Phe Pro Ile Arg Ser Tyr Glu Ile Gly Ala Asp Arg>
```

FIG. 3A

ACG GCC TCT ATA GAG ACG TTA ATG AAT CAT TTA CAG GAA ACT GCA CTT
Thr Ala Ser Ile Glu Thr Leu Met Asn His Leu Gln Glu Thr Ala Leu>

AAT CAT GTG AAG ATG GCT GGG TTG TTA GGA GAT GGA TTT GGT GCG ACG
Asn His Val Lys Met Ala Gly Leu Leu Gly Asp Gly Phe Gly Ala Thr>

CCT GAA ATG AGT AAA AAG AAT CTA ATT TGG GTT GTT ACG AAG ATG CAG
Pro Glu Met Ser Lys Lys Asn Leu Ile Trp Val Val Thr Lys Met Gln>

GTC CTT GTA GAA CAC TAT CCT AAA TGG GGA GAT GTG GTT GAA GTC GAT
Val Leu Val Glu His Tyr Pro Lys Trp Gly Asp Val Val Glu Val Asp>

ACA TGG GTT AGT GCA TCA GGA AAA AAT GGC ATG CGC CGT GAT TGG CAT
Thr Trp Val Ser Ala Ser Gly Lys Asn Gly Met Arg Arg Asp Trp His>

GTT CAT AAC ATC CGA ACT GGC CAA ACT GTC ATG CGA GCC ACA AGC GTT
Val His Asn Ile Arg Thr Gly Gln Thr Val Met Arg Ala Thr Ser Val>

TGG GTG ATG AAC AAA GTT ACT AGA AGG CTG TCT AAA ATG CCC GAA
Trp Val Met Met Asn Lys Val Thr Arg Arg Leu Ser Lys Met Pro Glu>

FIG. 3B

```
GAA GTT AGA GCA GAG ATA GGA CCT TTT TTT GTT GAC CGT GGT CCG ATC
Glu Val Arg Ala Glu Ile Gly Pro Phe Phe Val Asp Arg Gly Pro Ile>

ATA GAT GAA GAT AGC AGG AAA CTT CCT AAG CTA GAC GAG GAG TCA GCA
Ile Asp Glu Asp Ser Arg Lys Leu Pro Lys Leu Asp Glu Glu Ser Ala>

AAC CAT GTC AAA AAT GGA TTA ACT CCT CGA TGG AGC GAT TTG GAT GTC
Asn His Val Lys Asn Gly Leu Thr Pro Arg Trp Ser Asp Leu Asp Val>

AAC CAG CAT GTT AAC AAT GTT AAG TAC ATT GGA TGG ATT CTT GAG AGT
Asn Gln His Val Asn Asn Val Lys Tyr Ile Gly Trp Ile Leu Glu Ser>

GCA CCT ATA TCT CTT CTA GAG AGC CAT GAA CTT GCT AGC ATG ACT CTA
Ala Pro Ile Ser Leu Leu Glu Ser His Glu Leu Ala Ser Met Thr Leu>

GAA TAC AGG AGA GAG TGT GGA AGG GAC AGT GTG CTT CAG TCT CTT ACT
Glu Tyr Arg Arg Glu Cys Gly Arg Asp Ser Val Leu Gln Ser Leu Thr>

GCT GTA ACT TCT GAC TGT ACC ACG GAC ACT TCA CAT GAA AAA ACG TTC
Ala Val Thr Ser Asp Cys Thr Thr Asp Thr Ser His Glu Lys Thr Phe>
```

FIG. 3C

ACG GAG TGC AAT CAT CTA CTG CGG CTT GAT TGT GGG GCT GAG ATT GTA
Thr Glu Cys Asn His Leu Leu Arg Leu Asp Cys Gly Ala Glu Ile Val>

AGG GGA CAC ACG GAA TGG AGG CCC AAG AAT GCC CAG GAC CTC GCC AAC
Arg Gly His Thr Glu Trp Arg Pro Lys Asn Ala Gln Asp Leu Ala Asn>

ATG GGC CCA CCA AGC ATC AAC TGAT GATGATCCAG TATGAAAACT TCACCTTATA
Met Gly Pro Pro Ser Ile Asn>

TAAGCATTTT TACATGTGTA AATAATCGGT TTCAATTGTA GCGTGCCCAA AAAAAGTAA

CTTGAACTTG GGTTTGTGCT ATTGTTTGCT TTTTTATTCA GAAAGTTTAG CCTCGTGCCG

CTCGTGCCGA ATTC

FIG. 3D

AACAGCTGTC ATCACAAAAC TCCGATTTAA ATTAGTTAAA CTACTATTAT ATGCGGTCAA

AATTGGATTT TGCCTCGATC AAATTATTT TTACTATAGA GTTAGAAAAC ATGCATAAAT

AGATCCGGCC ACAGCAATTT GTCCATTAGT TTATCTTCAC ATACACTCTC TTTCTGGATT

CTGCTTCCAT CCCCGAAATA CATGCGGATT TACGATTCAA CCTAAATTGT TATCTCTCTA

GATTGTCCCC AAGTGTGGCC GCAGCTGAAC TTCTCGCGAT TTGGTTTGAA AAATTCTGAA

GAAGCTGCTA CTATAAGAAA TATAGTATC ATG GCT GCA TTT GCT TCC TCG GCC
                                Met Ala Ala Phe Ala Ser Ser Ala>

TTC TTC CCT ACT CCA TCC GGA CCA AAC TCG TCC TTA AAA TCC TCA AAA
Phe Phe Pro Thr Pro Ser Gly Pro Asn Ser Ser Leu Lys Ser Ser Lys>

CCA GTA AAT GGT AAT CAA GAT TCT CTA CAA GTC AAT GGA TTA GTA TCT
Pro Val Asn Gly Asn Gln Asp Ser Leu Gln Val Asn Gly Leu Val Ser>

AAA AAG AGT TTA TCA TCC ATG GAT GCA AAA ACA CAT GCT CAA
Lys Lys Ser Leu Ser Ser Met Asp Ala Lys Thr His Ala Gln>

FIG. 4A

```
GCT GTT CCA AAA ATA AAT GGA ACA AAG GTC GAT ACA AGG AGA AAT GAT
Ala Val Pro Lys Ile Asn Gly Thr Lys Val Asp Thr Arg Arg Asn Asp>

TCT TCA AGA GGG GAG GAC GAG GCT ATA TAC ACT ACT TCT TCT GCC CCT
Ser Ser Arg Gly Glu Asp Glu Ala Ile Tyr Thr Thr Ser Ser Ala Pro>

AGG ACA TTC TAT AAC CAG TTG CCT GAT TGG AGC ATG TTG CTA GCT GCC
Arg Thr Phe Tyr Asn Gln Leu Pro Asp Trp Ser Met Leu Leu Ala Ala>

ATT ACT ACT ATA TTT TTG GCA GCT GAG AAG CAA TGG ACT CTT ATT GAT
Ile Thr Thr Ile Phe Leu Ala Ala Glu Lys Gln Trp Thr Leu Ile Asp>

TGG AAG CCT AGG CGA CCT GAT ATG CTT TCT GAT GCG TGT GGN CTT GGA
Trp Lys Pro Arg Arg Pro Asp Met Leu Ser Asp Ala Cys Gly Leu Gly>

AAG ATT GCA CAA GAT GGG CTC GTG TTT ACT CAG AAT TCT CCT ATA CGA
Lys Ile Ala Gln Asp Gly Leu Val Phe Thr Gln Asn Ser Pro Ile Arg>

TCC TAT GAG ATA GGG GCA GNT CGG ACG GCC TCT ATA GAG ACG TTA ATG
Ser Tyr Glu Ile Gly Ala Xxx Arg Thr Ala Ser Ile Glu Thr Leu Met>
```

FIG. 4B

```
ACT CAT TTA CAG GAA ACT GCA CTT ACT CAT GTG AAG ATG GCT GGG TTG
Thr His Leu Gln Glu Thr Ala Leu Thr His Val Lys Met Ala Gly Leu>

TTA GGA GAT GGC TTT GGN GCG ACG CCT GAA ATG AGT AAA AAG AAT CTA
Leu Gly Asp Gly Phe Gly Ala Thr Pro Glu Met Ser Lys Lys Asn Leu>

ATT TGG GTT GTT ACG AAG ATG CAG GTC CTT GTA GAA CAC TAT CCT AAA
Ile Trp Val Val Thr Lys Met Gln Val Leu Val Glu His Tyr Pro Lys>

TGG GGA GAT GTG GTT GAA GTC GAT ACA TGG GTT AGT GCA TCA GGA AAA
Trp Gly Asp Val Val Glu Val Asp Thr Trp Val Ser Ala Ser Gly Lys>

AAT GGC ATG CGC CGT GAT TGG CAT GTT CAT AAC ATC CGA ACT GGC CAA
Asn Gly Met Arg Arg Asp Trp His Val His Asn Ile Arg Thr Gly Gln>

ACT GTC ATG CGA GCC ACA AGC GTT TGG GTG ATG ATG AAC AAA GTT ACT
Thr Val Met Arg Ala Thr Ser Val Trp Val Met Met Asn Lys Val Thr>

AGA AGG CTG TCT AAA ATG CCC GAA GAA GTT AGA GCA GAG ATA GGA CCT
Arg Arg Leu Ser Lys Met Pro Glu Glu Val Arg Ala Glu Ile Gly Pro>
```

FIG. 4C

```
TTT TTT GTT GAC CGT GGT CCG ATC ATA GAT GAA GAT AGC AGG AAA CTT
Phe Phe Val Asp Arg Gly Pro Ile Ile Asp Glu Asp Ser Arg Lys Leu>

CCT AAG CTA GAC GAG GAG TCA GCA AAC CAT GTC AAA AAT GGA TTA ACT
Pro Lys Leu Asp Glu Glu Ser Ala Asn His Val Lys Asn Gly Leu Thr>

CCT CGA TGG AGC GAT TTG GAT GTC AAC CAG CAT GTT AAC AAT GTT AAG
Pro Arg Trp Ser Asp Leu Asp Val Asn Gln His Val Asn Asn Val Lys>

TAC ATT GGA TGG ATT CTT GAG AGT GCA CCT ATA TCT CTT CTA GAG AGC
Tyr Ile Gly Trp Ile Leu Glu Ser Ala Pro Ile Ser Leu Leu Glu Ser>

CAT GAA CTT GCT AGC ATG ACT CTA GAA TAC AGG AGA GAG TGT GGA AGG
His Glu Leu Ala Ser Met Thr Leu Glu Tyr Arg Arg Glu Cys Gly Arg>

GAC AGT GTG CTT CAG TCT CTT ACT GCT GTA ACT TCT GAC TGT ACC ACG
Asp Ser Val Leu Gln Ser Leu Thr Ala Val Thr Ser Asp Cys Thr Thr>

GAC ACT TCA CGT GAA AAA ACG TTC ACG GAG TGC AAT CAT CTT CTG CGG
Asp Thr Ser Arg Glu Lys Thr Phe Thr Glu Cys Asn His Leu Leu Arg>
```

FIG. 4D

```
CTT GAT TGT GGG GCT GAG ATT GTA AGG GGA CAC ACG GAA TGG AGG CCC
Leu Asp Cys Gly Ala Glu Ile Val Arg Gly His Thr Glu Trp Arg Pro>

AAG AAT GCC CAG GAC CTC GCC AAC ATG GGC CCA CCA AGC ATG AAC TG
Lys Asn Ala Gln Asp Leu Ala Asn Met Gly Pro Pro Ser Met Asn>

ATGATGATCC AGTATAAAAA CGTCACCTTA TACTACTGCG ATATCTTGTA TTGCGCTATA

TAAGCATTTT TACATGTGTA AATAATCGAT TTCGACGTAT TTGATGGATG TGGGAAAAC

TTGTAGCATG CCCAAAAAAA GTAACTTGAA CTTGGGTTTG TCCTCGTGCC GAATTC
```

FIG. 4E

```
AGAGAGAGAG AGAGAGAGAG AGCTAAATTA AAAAAAAAAC CCAGAAGTGG GAAATCTTCC        60
CCATGAAATA ACGGATCCTC TTGCTACTGC TACTACTACT ACTACAAACT GTAGCCATTT       120
ATATAATTCT ATATAATTTT CAAC ATG GCC ACC ACC TCT TTA GCT TCC GCT TTC     174
                           Met Ala Thr Thr Ser Leu Ala Ser Ala Phe
                            1               5                  10

TGC TCG ATG AAA GCT GTA ATG TTG GCT CGT GAT GGC CGG GGC ATG AAA       222
Cys Ser Met Lys Ala Val Met Leu Ala Arg Asp Gly Arg Gly Met Lys
             15                  20                  25

CCC AGG AGC AGT GAT TTG CAG CTG AGG CTG AAT GCG GGA AAT GCG CCA ACC TCT   270
Pro Arg Ser Ser Asp Leu Gln Leu Arg Leu Asn Ala Gly Asn Ala Pro Thr Ser
             30                  35                  40

TTG AAG ATG ATC AAT GGG ACC AAG TTC AGT TAC ACG GAG AGC TTG AAA       318
Leu Lys Met Ile Asn Gly Thr Lys Phe Ser Tyr Thr Glu Ser Leu Lys
             45                  50                  55

AGG TTG CCT GAC TGG AGC ATG CTC TTT GCA GTG ATC ACA ACC ATC TTT       366
Arg Leu Pro Asp Trp Ser Met Leu Phe Ala Val Ile Thr Thr Ile Phe
             60                  65                  70

FIG. 5A
```

```
TCG GCT GCT GAG AAG CAG TGG ACC AAT CTA GAG TGG AAG CCG AAG CCG      414
Ser Ala Ala Glu Lys Gln Trp Thr Asn Leu Glu Trp Lys Pro Lys Pro
75                      80                      85                      90

AAG CTA CCC CAG TTG CTT GAT GAC CAT TTT GGA CTG CAT GGG TTA GTT      462
Lys Leu Pro Gln Leu Leu Asp Asp His Phe Gly Leu His Gly Leu Val
            95                      100                     105

TTC AGG CGC ACC TTT GCC ATC AGA TCT TAT GAG GTG GGA CCT GAC CGC      510
Phe Arg Arg Thr Phe Ala Ile Arg Ser Tyr Glu Val Gly Pro Asp Arg
        110                     115                     120

TCC ACA TCT ATA CTG GCT GTT ATG AAT CAC ATG CAG GAG GCT ACA CTT      558
Ser Thr Ser Ile Leu Ala Val Met Asn His Met Gln Glu Ala Thr Leu
        125                     130                     135

AAT CAT GCG AAG AGT GTG GGA ATT CTA GGA GAT GGA TTC GGG ACG ACG      606
Asn His Ala Lys Ser Val Gly Ile Leu Gly Asp Gly Phe Gly Thr Thr
140                     145                     150

CTA GAG ATG AGT AAG AGA GAT CTG ATG TGG GTT GTG AGA CGC ACG CAT      654
Leu Glu Met Ser Lys Arg Asp Leu Met Trp Val Val Arg Arg Thr His
155                     160                     165                     170
```

FIG. 5B

```
GTT GCT GTG GAA CGG TAC CCT ACT TGG GGT GAT ACT GTA GAA GTA GAG    702
Val Ala Val Glu Arg Tyr Pro Thr Trp Gly Asp Thr Val Glu Val Glu
            175                     180                     185

TGC TGG ATT GGT GCA TCT GGA AAT AAT GGC ATG CGA CGT GAT TTC CTT    750
Cys Trp Ile Gly Ala Ser Gly Asn Asn Gly Met Arg Arg Asp Phe Leu
            190                     195                     200

GTC CGG GAC TGC AAA ACA GGC GAA ATT CTT ACA AGA TGT ACC AGC CTT    798
Val Arg Asp Cys Lys Thr Gly Glu Ile Leu Thr Arg Cys Thr Ser Leu
            205                     210                     215

TCG GTG CTG ATG AAT ACA AGG AGG TTG TCC ACA ATC CCT GAC            846
Ser Val Leu Met Asn Thr Arg Arg Leu Ser Thr Ile Pro Asp
            220                     225                     230

GAA GTT AGA GGG GAG ATA GGG CCT GCA TTC ATT GAT AAT GTG GCT GTC    894
Glu Val Arg Gly Glu Ile Gly Pro Ala Phe Ile Asp Asn Val Ala Val
            235                     240                     245                 250

AAG GAC GAT GAA ATT AAG AAA CTA CAG AAG CTC AAT GAC AGC ACT GCA    942
Lys Asp Asp Glu Ile Lys Lys Leu Gln Lys Leu Asn Asp Ser Thr Ala
            255                     260                     265
```

FIG. 5C

| | | | | | | | | | | | | | | | | |
|---|---|---|---|---|---|---|---|---|---|---|---|---|---|---|---|---|
| GAT | TAC | ATC | CAA | GGA | GGT | TTG | ACT | CCT | CGA | TGG | AAT | GAT | TTG | GAT | GTC | 990 |
| Asp | Tyr | Ile | Gln | Gly | Gly | Leu | Thr | Pro | Arg | Trp | Asn | Asp | Leu | Asp | Val | |
| | 270 | | | | | | | 275 | | | | | 280 | | | |
| AAT | CAG | CAT | GTG | AAC | AAC | CTC | AAA | TAC | GTT | GCC | TGG | GTT | TTT | GAG | ACC | 1038 |
| Asn | Gln | His | Val | Asn | Asn | Leu | Lys | Tyr | Val | Ala | Trp | Val | Phe | Glu | Thr | |
| | | 285 | | | | | 290 | | | | | 295 | | | | |
| GTC | CCA | GAC | TCC | ATC | TTT | GAG | AGT | CAT | CAT | ATT | TCC | AGC | TTC | ACT | CTT | 1086 |
| Val | Pro | Asp | Ser | Ile | Phe | Glu | Ser | His | His | Ile | Ser | Ser | Phe | Thr | Leu | |
| 300 | | | | | 305 | | | | | 310 | | | | | | |
| GAA | TAC | AGG | AGA | GAG | TGC | ACG | AGG | GAT | AGC | GTG | CTG | CGG | TCC | CTG | ACC | 1134 |
| Glu | Tyr | Arg | Arg | Glu | Cys | Thr | Arg | Asp | Ser | Val | Leu | Arg | Ser | Leu | Thr | |
| 315 | | | | | 320 | | | | | 325 | | | | | 330 | |
| ACT | GTC | TCT | GGT | GGC | TCG | TCG | GAG | GCT | GGG | TTA | GTG | TGC | GAT | CAC | TTG | 1182 |
| Thr | Val | Ser | Gly | Gly | Ser | Ser | Glu | Ala | Gly | Leu | Val | Cys | Asp | His | Leu | |
| | | | 335 | | | | | 340 | | | | | 345 | | | |
| CTC | CAG | CTT | GAA | GGT | GGG | TCT | GAG | GTA | TTG | AGG | GCA | AGA | ACA | GAG | TGG | 1230 |
| Leu | Gln | Leu | Glu | Gly | Gly | Ser | Glu | Val | Leu | Arg | Ala | Arg | Thr | Glu | Trp | |
| | 350 | | | | | | 355 | | | | | 360 | | | | |

FIG. 5D

```
AGG CCT AAG CTT ACC GAT AGT TTC AGA GGG ATT AGT GTG ATA CCC GCA   1278
Arg Pro Lys Leu Thr Asp Ser Phe Arg Gly Ile Ser Val Ile Pro Ala
365                     370                     375

GAA CCG AGG GTG TAACTAATGA AAGAAGCATC TGTTGAAGTT TCTCCCATGC        1330
Glu Pro Arg Val
        380

TGTTCGTGAG GATACTTTTT AGAAGCTGCA GTTTGCATTG CTTGTGCAGA ATCATGGTCT  1390

GTGGTTTTAG ATGTATATAA AAAATAGTCC TGTAGTCATG AAACTTAATA TCAGAAAAAT  1450

AACTCAATGG GTCAAGGTTA TCGAAGTAGT CATTTAAGCT TTGAAATATG TTTTGTATTC  1510

CTCGGCTTAA TCTGTAAGCT CTTTCTCTTG CAATAAAGTT CGCCTTTCAA T           1561
```

FIG. 5E

```
CTGGATACCA TTTCCCTGC GAAAAAAC ATG GTG GCT GCA GCT GCA AGT TCC                           52
                              Met Val Ala Ala Ala Ala Ser Ser
                               1                    5

GCA TTC TTC CCT GTT CCA GCC CCG GGA GCC TCC CCT AAA CCC GGG AAG                         100
Ala Phe Phe Pro Val Pro Ala Pro Gly Ala Ser Pro Lys Pro Gly Lys
             10                  15                  20

TTC GGA AAT TGG CCC TCG AGC TTG AGC CCT TCC TTC AAG CCC AAG TCA                         148
Phe Gly Asn Trp Pro Ser Ser Leu Ser Pro Ser Phe Lys Pro Lys Ser
 25                  30                  35                  40

ATC CCC AAT GGC GGA TTT CAG GTT AAG GCA AAT GAC AGC GCC CAT CCA                         196
Ile Pro Asn Gly Gly Phe Gln Val Lys Ala Asn Asp Ser Ala His Pro
                 45                  50                  55

AAG GCT AAC GGT TCT GCA GTT AGT CTA AAG TCT GGC AGC CTC AAC ACT                         244
Lys Ala Asn Gly Ser Ala Val Ser Leu Lys Ser Gly Ser Leu Asn Thr
 60                  65                  70

CAG GAG GAC ACT TCG TCC CCT CCT CCT CGG ACT TTC CTT CAC CAG                             292
Gln Glu Asp Thr Ser Ser Pro Pro Pro Arg Thr Phe Leu His Gln
 75                  80                  85
```

FIG. 6A

```
TTG CCT GAT TGG AGT AGG CTT CTG ACT GCA ATC ACG ACC GTG TTC GTG    340
Leu Pro Asp Trp Ser Arg Leu Leu Thr Ala Ile Thr Thr Val Phe Val
 90                  95                 100

AAA TCT AAG AGG CCT GAC ATG CAT GAT CGG AAA TCC AAG AGG CCT GAC    388
Lys Ser Lys Arg Pro Asp Met His Asp Arg Lys Ser Lys Arg Pro Asp
105                 110                 115                 120

ATG CTG GTG GAC TCG TTT GGG TTG GAG AGT ACT GTT CAG GAT GGG CTC    436
Met Leu Val Asp Ser Phe Gly Leu Glu Ser Thr Val Gln Asp Gly Leu
            125                 130                 135

GTG TTC CGA CAG AGT TTT TCG ATT AGG TCT TAT GAA ATA GGC ACT GAT    484
Val Phe Arg Gln Ser Phe Ser Ile Arg Ser Tyr Glu Ile Gly Thr Asp
        140                 145                 150

CGA ACG GCC TCT ATA GAG ACA CTT ATG AAC CAC TTG CAG GAA ACA TCT    532
Arg Thr Ala Ser Ile Glu Thr Leu Met Asn His Leu Gln Glu Thr Ser
            155                 160                 165

CTC AAT CAT TGT AAG AGT ACC GGT ATT CTC CTT GAC GGC TTC GGT CGT    580
Leu Asn His Cys Lys Ser Thr Gly Ile Leu Leu Asp Gly Phe Gly Arg
170                 175                 180
```

FIG. 6B

```
ACT CTT GAG ATG TGT AAA AGG GAC CTC ATT TGG GTG GTA ATA AAA ATG   628
Thr Leu Glu Met Cys Lys Arg Asp Leu Ile Trp Val Val Ile Lys Met
185                 190                 195                 200

CAG ATC AAG GTG AAT CGC TAT CCA GCT TGG GGC GAT ACT GTC GAG ATC   676
Gln Ile Lys Val Asn Arg Tyr Pro Ala Trp Gly Asp Thr Val Glu Ile
        205                 210                 215

AAT ACC CGG TTC TCC CGG TTG GGG AAA ATC GGT ATG GGT CGC GAT TGG   724
Asn Thr Arg Phe Ser Arg Leu Gly Lys Ile Gly Met Gly Arg Asp Trp
220                 225                 230

CTA ATA AGT GAT TGC AAC ACA GGA GAA ATT CTT GTA AGA GCT ACG AGC   772
Leu Ile Ser Asp Cys Asn Thr Gly Glu Ile Leu Val Arg Ala Thr Ser
        235                 240                 245

GCG TAT GCC ATG ATG AAT CAA AAG ACG AGA AGA CTC TCA AAA CTT CCA   820
Ala Tyr Ala Met Met Asn Gln Lys Thr Arg Arg Leu Ser Lys Leu Pro
250                 255                 260

TAC GAG GTT CAC CAG GAG ATA GTG CCT CTT TTT GTC GAC TCT CCT GTC   868
Tyr Glu Val His Gln Glu Ile Val Pro Leu Phe Val Asp Ser Pro Val
265                 270                 275                 280
```

FIG. 6C

```
ATT GAA GAC AGT GAT CTG AAA GTG CAT AAG TTT AAA GTG AAG ACT GGT    916
Ile Glu Asp Ser Asp Leu Lys Val His Lys Phe Lys Val Lys Thr Gly
            285                 290                 295

GAT TCC ATT CAA AAG GGT CTA ACT CCG GGG TGG AAT GAC TTG GAT GTC    964
Asp Ser Ile Gln Lys Gly Leu Thr Pro Gly Trp Asn Asp Leu Asp Val
            300                 305                 310

AAT CAG CAC GTA AGC AAC GTG AAG TAC ATT GGG TGG ATT CTC GAG AGT   1012
Asn Gln His Val Ser Asn Val Lys Tyr Ile Gly Trp Ile Leu Glu Ser
            315                 320                 325

ATG CCA ACA GAA GTT TTG GAG ACC CAG GAG CTA TGC TCT CTC GCC CTT   1060
Met Pro Thr Glu Val Leu Glu Thr Gln Glu Leu Cys Ser Leu Ala Leu
            330                 335                 340

GAA TAT AGG CGG GAA TGC GGA AGG GAC AGT GTG CTG GAG TCC GTG ACC   1108
Glu Tyr Arg Arg Glu Cys Gly Arg Asp Ser Val Leu Glu Ser Val Thr
            345                 350                 355                 360

GCT ATG GAT CCC TCA AAA GTT GGA GTC CGT TCT CAG TAC CAG CAC CTT   1156
Ala Met Asp Pro Ser Lys Val Gly Val Arg Ser Gln Tyr Gln His Leu
            365                 370                 375
```

FIG. 6D

```
CTG CGG CTT GAG GAT GGG ACT GCT ATC GTG AAC GGT GCA ACT GAG TGG   1204
Leu Arg Leu Glu Asp Gly Thr Ala Ile Val Asn Gly Ala Thr Glu Trp
            380                 385                 390

CGG CCG AAG AAT GCA GGA GCT AAC GGG GCG ATA TCA ACG GGA AAG ACT   1252
Arg Pro Lys Asn Ala Gly Ala Asn Gly Ala Ile Ser Thr Gly Lys Thr
            395                 400                 405

TCA AAT GGA AAC TCG GTC TCT TAGAAGTGTC TCGGAACCCT TCCGAGATGT      1303
Ser Asn Gly Asn Ser Val Ser
            410         415

GCATTTCTTT TCTCCTTTTC ATTTTGTGGT GAGCTGAAAG AAGAGCATGT CGTTGCAATC 1363

AGTAAATTGT GTAGTTCGTT TTTCGCTTTG CTTCGCTCCT TTGTATAATA ATATGGTCAG 1423

TCGTCTTTGT ATCATTTCAT GTTTTCAGTT TATTTACGCC ATATATAATTTT T        1474
```

FIG. 6E

```
CTTTGATCGG TCGATCCTTT CCTCTCGCTC ATAATTTACC CATTAGTCCC CTTTGCCTTC     60

TTTAAACCCT CCTTTCCTTT CTCTTCCCTT CTTCCTCTCT GGGAAGTTTA AAGCTTTTGC    120

CTTTCTCCCC CCCACAACCT CTTTCCCGCA TTTGTTGAGC TGTTTTTTTG TCGCCATTCG    180

TCCTCTCCTC TTCAGTTCAA CAGAA ATG GTG GCT ACC GCT GCA AGT TCT GCA      232
                            Met Val Ala Thr Ala Ala Ser Ser Ala
                            1                 5

TTC TTC CCC CTC CCA TCC GAC ACC TCA TCG AGA CCC GGA AAG CTC          280
Phe Phe Pro Leu Pro Ser Asp Thr Ser Ser Arg Pro Gly Lys Leu
10                  15                  20                  25

GGC AAT AAG CCA TCG AGC TTG AGC CCC CTC AAG CCC AAA TCG ACC CCC      328
Gly Asn Lys Pro Ser Ser Leu Ser Pro Leu Lys Pro Lys Ser Thr Pro
        30                  35                  40

AAT GGC GGT TTG CAG GTT AAG GCA AAT GCC AGT GCC CCT CCT AAG ATC      376
Asn Gly Gly Leu Gln Val Lys Ala Asn Ala Ser Ala Pro Pro Lys Ile
45                  50                  55
```

FIG. 7A

```
AAT GGT TCC CCG GTC GGT CTA AAG TCG GGC GGT CTC AAG ACT CAG GAA     424
Asn Gly Ser Pro Val Gly Leu Lys Ser Gly Gly Leu Lys Thr Gln Glu
         60                   65                   70

GAC GCT CAT TCG GCC CCT CCG CGA ACT TTT ATC AAC CAG TTG CCT         472
Asp Ala His Ser Ala Pro Pro Arg Thr Phe Ile Asn Gln Leu Pro
         75                   80                   85

GAT TGG AGT ATG CTT CTT GCT GCA ATC ACG ACT GTC TTC TTG GCT GCA     520
Asp Trp Ser Met Leu Leu Ala Ala Ile Thr Thr Val Phe Leu Ala Ala
         90                   95                  100         105

GAG AAG CAA TGG ATG ATG CTT GAT TGG AAA CCT AAG AGG CCT GAC ATG     568
Glu Lys Gln Trp Met Met Leu Asp Trp Lys Pro Lys Arg Pro Asp Met
        110                  115                  120

CTT GTG GAC CCG TTT GGA TTG CAG GAT GTT CAG GAT GGG CTT GTG         616
Leu Val Asp Pro Phe Gly Leu Gln Asp Val Gln Asp Gly Leu Val
        125                  130                  135

TTC AGG CAG AAT TTT TCG ATT AGG TCC TAT GAA ATA GGC GCC GAT CGC     664
Phe Arg Gln Asn Phe Ser Ile Arg Ser Tyr Glu Ile Gly Ala Asp Arg
        140                  145                  150
```

FIG. 7B

```
ACT GCG TCT ATA GAG ACG GTG ATG AAC CAT TTG CAG GAA ACA GCT CTC    712
Thr Ala Ser Ile Glu Thr Val Met Asn His Leu Gln Glu Thr Ala Leu
        155                 160                 165

AAT CAT GTT AAG ATT GCT GGG CTT TCT AAT GAC GGC TTT GGT CGT ACT    760
Asn His Val Lys Ile Ala Gly Leu Ser Asn Asp Gly Phe Gly Arg Thr
    170                 175                 180                 185

CCT GAG ATG TAT AAA AGG GAC CTT ATT TGG GTT GTT GCG AAA ATG CAA    808
Pro Glu Met Tyr Lys Arg Asp Leu Ile Trp Val Val Ala Lys Met Gln
        190                 195                 200

GTC ATG GTT AAC CGC TAT CCT ACT TGG GGT GAC ACG GTT GAA GTG AAT    856
Val Met Val Asn Arg Tyr Pro Thr Trp Gly Asp Thr Val Glu Val Asn
    205                 210                 215

ACT TGG GTT GCC AAG TCA GGG AAA AAT GGT ATG CGT CGT GAC TGG CTC    904
Thr Trp Val Ala Lys Ser Gly Lys Asn Gly Met Arg Arg Asp Trp Leu
        220                 225                 230

ATA AGT GAT TGC AAT ACT GGA GAG ATT CTT ACA AGA GCA TCA AGC GTG    952
Ile Ser Asp Cys Asn Thr Gly Glu Ile Leu Thr Arg Ala Ser Ser Val
    235                 240                 245
```

FIG. 7C

```
TGG GTC ATG ATG AAT CAA AAG ACA AGA AGA TTG TCA AAA ATT CCA GAT    1000
Trp Val Met Met Asn Gln Lys Thr Arg Arg Leu Ser Lys Ile Pro Asp
250                 255                 260                 265

GAG GTT CGA AAT GAG ATA GAG CCT CAT TTT GTG GAC TCT CCT CCC GTC    1048
Glu Val Arg Asn Glu Ile Glu Pro His Phe Val Asp Ser Pro Pro Val
        270                 275                 280

ATT GAA GAC GAT GAC CGG AAA CTT CCC AAG CTG GAT GAG AAG ACT GCT    1096
Ile Glu Asp Asp Asp Arg Lys Leu Pro Lys Leu Asp Glu Lys Thr Ala
            285                 290                 295

GAC TCC ATC CGC AAG GGT CTA ACT CCG AGG TGG AAT GAC TTG GAT GTC    1144
Asp Ser Ile Arg Lys Gly Leu Thr Pro Arg Trp Asn Asp Leu Asp Val
300                 305                 310

AAT CAA CAC GTC AAC AAC GTG AAG TAC ATC GGG TGG ATT CTT GAG AGT    1192
Asn Gln His Val Asn Asn Val Lys Tyr Ile Gly Trp Ile Leu Glu Ser
        315                 320                 325

ACT CCA CCA GAA GTT CTG GAG ACC CAG GAG TTA TGT TCC CTT ACT CTG    1240
Thr Pro Pro Glu Val Leu Glu Thr Gln Glu Leu Cys Ser Leu Thr Leu
330                 335                 340                 345
```

FIG. 7D

```
GAA TAC AGG CGG GAA TGT GGA AGG GAG AGC GTG CTG GAG TCC CTC ACT  1288
Glu Tyr Arg Arg Glu Cys Gly Arg Glu Ser Val Leu Glu Ser Leu Thr
            350                 355                 360

GCT ATG GAT CCC TCT GGA GGG GGT TAT GGG TCC CAG TTT CAG CAC CTT  1336
Ala Met Asp Pro Ser Gly Gly Gly Tyr Gly Ser Gln Phe Gln His Leu
        365                 370                 375

CTG CGG CTT GAG GAT GGA GGT GAG ATC GTG AAG GGG AGA ACT GAG TGG  1384
Leu Arg Leu Glu Asp Gly Gly Glu Ile Val Lys Gly Arg Thr Glu Trp
    380                 385                 390

CGG CCC AAG AAT GGT GTA ATC AAT GGG GTG GTA CCA ACC GGG GAG TCC  1432
Arg Pro Lys Asn Gly Val Ile Asn Gly Val Val Pro Thr Gly Glu Ser
395                 400                 405

TCA CCT GGA GAC TAC TCT TAGAAGGGAG CCCTGACCCC TTTGGAGTTG         1480
Ser Pro Gly Asp Tyr Ser
410                 415

TGATTTCTTT ATTGTCGGAC GAGCTAAGTG AAGGGCAGGT AAGATAGTAG CAATCGGTAG 1540
```

FIG. 7E

```
ATTGTGTAGT TTGTTTGCTG CTTTTTCACG ATGGCTCTCG TGTATAATAT CATGGTCTGT 1600
CTTCTTTGTA TCCTCTTCTT CGCATGTTCC GGGTTGATTC ATACATTATA TTCTTTCTAT 1660
TTGTTTGAAG GCCGAGTAGCG GGTTGTAATT ATTTATTTTG TCATTACAAT GTCGTTTAAC 1720
TTTTCAAATG AAACTACTTA TGTG 1744
```

FIG. 7F

```
GAA TTC GGC ACG AGG GGC TCC GGT GCT TTG CAG GTG AAG GCA AGT TCC    48
Glu Phe Gly Thr Arg Gly Ser Gly Ala Leu Gln Val Lys Ala Ser Ser
                 5                  10                  15

CAA GCT CCA CCA AAG CTC AAT GGT TCC AAT GTG GGT TTG GTT AAA TCT    96
Gln Ala Pro Pro Lys Leu Asn Gly Ser Asn Val Gly Leu Val Lys Ser
         20                  25                  30

AGC CAA ATT GTG AAG AAG GGT GAT GAC ACC ACA TCT CCT GCA AGA       144
Ser Gln Ile Val Lys Lys Gly Asp Asp Thr Thr Ser Pro Ala Arg
             35                  40                  45

ACT TTC ATC AAC CAA TTG CCT GAT TGG AGC ATG CTT CTT GCT GCT ATC   192
Thr Phe Ile Asn Gln Leu Pro Asp Trp Ser Met Leu Leu Ala Ala Ile
         50                  55                  60

ACA ACC CTG TTC TTG GCT GCA GAG AAG CAG TGG ATG CTT GAT TGG       240
Thr Thr Leu Phe Leu Ala Ala Glu Lys Gln Trp Met Leu Asp Trp
 65                  70                  75                  80

AAA CCC AAA AGG CCT GAC ATG CTT GTT GAT CCA TTT GGT CTT GGA AGG   288
Lys Pro Lys Arg Pro Asp Met Leu Val Asp Pro Phe Gly Leu Gly Arg
             85                  90                  95

TTT GTT CAG GAT GGT CTT GTT TTC CGC AAC AAC TTT TCA ATT CGA TCA   336
Phe Val Gln Asp Gly Leu Val Phe Arg Asn Asn Phe Ser Ile Arg Ser
 100                 105                 110
```

FIG. 8A

```
TAT GAA ATA GGG GCT GAT CGA ACG GCT TCT ATA GAA ACG TTA ATG AAT   384
Tyr Glu Ile Gly Ala Asp Arg Thr Ala Ser Ile Glu Thr Leu Met Asn
            115                 120                 125

CAT CTG CAG GAA ACA GCT CTT AAT CAT GTG AAG TCT GTT GGG CTT CTT   432
His Leu Gln Glu Thr Ala Leu Asn His Val Lys Ser Val Gly Leu Leu
            130                 135                 140

GAG GAT GGC CTA GGT TCG ACT CGA GAG ATG TCC TTG AGG AAC CTG ATA   480
Glu Asp Gly Leu Gly Ser Thr Arg Glu Met Ser Leu Arg Asn Leu Ile
145                 150                 155                 160

TGG GTT GTC ACT AAA ATG CAG GTT GCG GTT GAT CGC TAT CCA ACT TGG   528
Trp Val Val Thr Lys Met Gln Val Ala Val Asp Arg Tyr Pro Thr Trp
                165                 170                 175

GGA GAT GAA GTT CAG GTA TCC TCT TGG GCT ACT GCA ATT GGA AAG AAT   576
Gly Asp Glu Val Gln Val Ser Ser Trp Ala Thr Ala Ile Gly Lys Asn
                    180                 185                 190

GGA ATG CGT CGC GAA TGG ATA GTC ACT GAT TTT AGA ACT GGT GAA ACT   624
Gly Met Arg Arg Glu Trp Ile Val Thr Asp Phe Arg Thr Gly Glu Thr
                        195                 200                 205

CTA TTA AGA GCC ACC AGT GTT TGG GTG ATG ATG AAT AAA CTG ACG AGG   672
Leu Leu Arg Ala Thr Ser Val Trp Val Met Met Asn Lys Leu Thr Arg
210                 215                 220

FIG. 8B
```

```
AGG ATA TCC AAA ATC CCA GAA GAG GTT TGG CAC GAA ATA GGC CCC TCT   720
Arg Ile Ser Lys Ile Pro Glu Glu Val Trp His Glu Ile Gly Pro Ser
225                 230                 235                 240

TTC ATT GAT GCT CCT CCT CTT CCC ACC GTG GAA GAT GGT AGA AAG       768
Phe Ile Asp Ala Pro Pro Leu Pro Thr Val Glu Asp Gly Arg Lys
        245                 250                 255

CTG ACA AGG TTT GAT GAA AGT TCT GCA GAC TTT ATC CGC NCT GGT TTA   816
Leu Thr Arg Phe Asp Glu Ser Ser Ala Asp Phe Ile Arg Xxx Gly Leu
        260                 265                 270

ACT CCT AGG TGG AGT GAT TTG GAC AAC CAG CAT GTC AAC AAT GTG       864
Thr Pro Arg Trp Ser Asp Leu Asp Asn Gln His Val Asn Asn Val
275                 280                 285

AAG TAC ATT GGC TGG CTC CTT GAG AGT GCT CCG CCG GAG ATC CAC GAG   912
Lys Tyr Ile Gly Trp Leu Leu Glu Ser Ala Pro Pro Glu Ile His Glu
        290                 295                 300

AGT CAC GAG ATA GCG TCT CTG ACT CTG GAG TAC AGG AGG GAG TGT GGA   960
Ser His Glu Ile Ala Ser Leu Thr Leu Glu Tyr Arg Arg Glu Cys Gly
305                 310                 315                 320

AGG GAC AGC GTG CTG AAC TCC GCG ACC AAG GTC TCT GAC TCC TCT CAA  1008
Arg Asp Ser Val Leu Asn Ser Ala Thr Lys Val Ser Asp Ser Ser Gln
        325                 330                 335
```

FIG. 8C

```
CTG GGA AAG TCT GCT GTG GAG TGT AAC CAC TTG GTT CGT CTC CAG AAT    1056
Leu Gly Lys Ser Ala Val Glu Cys Asn His Leu Val Arg Leu Gln Asn
                340                 345                 350

GGT GGG GAG ATT CTC AAG GGA AGG ACT GTG TGG AGG CCC AAA CGT CCT    1104
Gly Gly Glu Ile Leu Lys Gly Arg Thr Val Trp Arg Pro Lys Arg Pro
                355                 360                 365

CTT TAC AAT GAT GGT GCT GTT GTG GAC GTG NAA GCT AAA ACC TCT        1149
Leu Tyr Asn Asp Gly Ala Val Val Asp Val Xxx Ala Lys Thr Ser
                370                 375                 380

TAAGTCTTAT AGTCCAAGTG AGGAGGAGTT CTATGTATCA GGAAGTTGCT AGGATTCTCA  1209

ATCGCATGTG TCCATTCTT GTGTGGAATA CTGCTCGTGT TTCTAGACTC GCTATATGTT   1269

TGTTCTTTTA TATATATATA TATATATATA TCTCTCTCTT CCCCCACCT CTCTCTCTCT   1329

CTCTATATAT ATATATGTTT TATGTAAGTT TTCCCCTTAG TTTCCTTTCC TAAGTAATGC  1389

CATTGTAAAT TACTTCAAAA AAAAAAAAAA AAAAAAACT CGAG                    1433
```

FIG. 8D

```
TCAAC ATG GCC ACC ACC TCT TTA GCT TCT GCT TTC TGC TCG ATG AAA GCT    50
      Met Ala Thr Thr Ser Leu Ala Ser Ala Phe Cys Ser Met Lys Ala
      1                   5                  10                  15

GTA ATG TTG GCT CGT GAT GGC AGG GGC ATG AAA CCC AGG AGC AGT GAT      98
Val Met Leu Ala Arg Asp Gly Arg Gly Met Lys Pro Arg Ser Ser Asp
                    20                  25                  30

TTG CAG CTG AGG GCG GGA AAT GCA CAA ACC TCT TTG AAG ATG ATC AAT     146
Leu Gln Leu Arg Ala Gly Asn Ala Gln Thr Ser Leu Lys Met Ile Asn
                35                  40                  45

GGG ACC AAG TTC AGT TAC ACA GAG TCG TTG AAA AAG TTG CCT GAC TGG     194
Gly Thr Lys Phe Ser Tyr Thr Glu Ser Leu Lys Lys Leu Pro Asp Trp
        50                  55                  60

AGC ATG CTC TTT GCA GTG ATC ACC ATC TTT TCG GCT GCT GAG AAG         242
Ser Met Leu Phe Ala Val Ile Thr Ile Phe Ser Ala Ala Glu Lys
65                  70                  75

CAG TGG ACC AAT CTA GAG TGG AAG CCG AAT CCA CCC CAG TTG             290
Gln Trp Thr Asn Leu Glu Trp Lys Pro Asn Pro Pro Gln Leu
80                  85                  90                  95
```

FIG. 9A

```
CTT GAT GAC CAT TTT GGG CCG CAT GGG TTA GTT TTC AGG CGC ACC TTT    338
Leu Asp Asp His Phe Gly Pro His Gly Leu Val Phe Arg Arg Thr Phe
100                     105                     110

GCC ATC AGA TCG TAT GAG GTG GGA CCT GAC CGC TCC ACA TCT ATA GTG    386
Ala Ile Arg Ser Tyr Glu Val Gly Pro Asp Arg Ser Thr Ser Ile Val
        115                     120                     125

GCT GTT ATG AAT CAC TTG CAG GAG GCT GCA CTT AAT CAT GCG AAG AGT    434
Ala Val Met Asn His Leu Gln Glu Ala Ala Leu Asn His Ala Lys Ser
130                     135                     140

GTG GGA ATT CTA GGA GAT GGA TTC GGT ACG ACG CTA GAG ATG AGT AAG    482
Val Gly Ile Leu Gly Asp Gly Phe Gly Thr Thr Leu Glu Met Ser Lys
        145                     150                     155

AGA GAT CTG ATA TGG GTT GTT GTG AAA CGC ACG CAT GTT GCT GTG GAA CGG    530
Arg Asp Leu Ile Trp Val Val Val Lys Arg Thr His Val Ala Val Glu Arg
160                     165                     170                 175
```

FIG. 9B

```
TAC CCT GCT TGG GGT GAT ACT GTT GAA GTA GAG TGC TGG GTT GGT GCA    578
Tyr Pro Ala Trp Gly Asp Thr Val Glu Val Glu Cys Trp Val Gly Ala
            180                 185                 190

TCG GGA AAT AAT GGC AGG CGC CAT GAT TTC CTT GTC CGG GAC TGC AAA    626
Ser Gly Asn Asn Gly Arg Arg His Asp Phe Leu Val Arg Asp Cys Lys
            195                 200                 205

ACA GGC GAA ATT CTT ACA AGA TGT ACC AGT CTT TCG GTG ATG ATG AAT    674
Thr Gly Glu Ile Leu Thr Arg Cys Thr Ser Leu Ser Val Met Met Asn
            210                 215                 220

ACA AGG ACA AGG AGG TTG TCC AAA ATC CCT GAA GAA GTT AGA GGG GAG    722
Thr Arg Thr Arg Arg Leu Ser Lys Ile Pro Glu Glu Val Arg Gly Glu
            225                 230                 235

ATA GGG CCT GCA TTC ATT GAT AAT GTG GCT GTC AAG GAC GAG GAA ATT    770
Ile Gly Pro Ala Phe Ile Asp Asn Val Ala Val Lys Asp Glu Glu Ile
            240                 245                 250         255
```

FIG. 9C

```
AAG AAA CCA CAG AAG CTC AAT GAC AGC ACT GCA GAT TAC ATC CAA GGA    818
Lys Lys Pro Gln Lys Leu Asn Asp Ser Thr Ala Asp Tyr Ile Gln Gly
             260                 265                 270

GGA TTG ACT CCT CGA TGG AAT GAT TTG GAT ATC AAT CAG CAC GTT AAC    866
Gly Leu Thr Pro Arg Trp Asn Asp Leu Asp Ile Asn Gln His Val Asn
             275                 280                 285

AAC ATC AAA TAC GTT GAC TGG ATT CTT GAG ACT GTC CCA GAC TCA ATC    914
Asn Ile Lys Tyr Val Asp Trp Ile Leu Glu Thr Val Pro Asp Ser Ile
             290                 295                 300

TTT GAG AGT CAT CAT ATT TCC AGC TTC ACT ATT GAA TAC AGG AGA GAG    962
Phe Glu Ser His His Ile Ser Ser Phe Thr Ile Glu Tyr Arg Arg Glu
             305                 310                 315

TGC ACG ATG GAT AGC GTG CTG CAG TCC CTG ACC ACT GTC TCC GGT GGC   1010
Cys Thr Met Asp Ser Val Leu Gln Ser Leu Thr Thr Val Ser Gly Gly
             320                 325                 330       335
```

FIG. 9D

```
TCG TCG GAA GCT GGG TTA GTG TGC GAG CAC TTG CTC CAG CTT GAA GGT    1058
Ser Ser Glu Ala Gly Leu Val Cys Glu His Leu Leu Gln Leu Glu Gly
                340                     345                 350

GGG TCT GAG GTA TTG AGG GCA AAA ACA GAG TGG AGG CCT AAG CTT ACC    1106
Gly Ser Glu Val Leu Arg Ala Lys Thr Glu Trp Arg Pro Lys Leu Thr
            355                     360                 365

GAT AGT TTC AGA GGG ATT AGT GTG ATA CCC GCA GAA TCG AGT GTC        1151
Asp Ser Phe Arg Gly Ile Ser Val Ile Pro Ala Glu Ser Ser Val
        370                     375                 380

TAACTAACGA AAGAAGCATC TGATGAAGTT TCTCCCTGTGC TGTTGTTCGT GAGGATGCTT   1211

TTTAGAAGCT GCAGTTGCA TTGCTTGTGC AGAATCATGG CCTGTGGTTT TAGATATATA    1271

TCCAAAATTG TCCTATAGTC AAGAAACTTA ATATCAGAAA AATAACTCAA TGAGTCAAGG   1331
```

FIG. 9E

```
TTATCGAAGT AGTCATGTAA GCTTTGAAAT ATGTTGTGTA TTCCTCGGCT TTATGTAATC   1391
TGTAAGCTCT TTCTCTTGCA ATAAATTTCG CCTTTCAATA ATAAAAAAAA AAAAAAAAGG   1451
TCGACTCGAG                                                         1461
```

FIG. 9F

```
AAAAAGTAC AAACTGTATG GTAGCCATTT ACATATAACT ACTCTATAAT TTTCAAC ATG    60
                                                            Met
                                                              1

GTC ACC ACC TCT TTA GCT TCC GCT TTC TTC TCG ATG AAA GCT GTA ATG   108
Val Thr Thr Ser Leu Ala Ser Ala Phe Phe Ser Met Lys Ala Val Met
              5                  10                  15

TTG GCT CCT GAT GGC AGT GGC ATA AAA CCC AGG AGC AGT GGT TTG CAG   156
Leu Ala Pro Asp Gly Ser Gly Ile Lys Pro Arg Ser Ser Gly Leu Gln
          20                  25                  30

GTG AGG GCG GGA AAG GAA CAA AAC TCT TGC AAG ATG ATC AAT GGG ACC   204
Val Arg Ala Gly Lys Glu Gln Asn Ser Cys Lys Met Ile Asn Gly Thr
      35                  40                  45

AAG GTC AAA GAC ACG GAG GGC TTG AAA CTG AAA GGG CGC AGC ACA TTG CAT GGC   252
Lys Val Lys Asp Thr Glu Gly Leu Lys Leu Lys Gly Arg Ser Thr Leu His Gly
  50                  55                  60                  65

TGG AGC ATG CCC CTT GAA TTG ATC ACA ACC ATC TTT TCG GCT GCT GAG   300
Trp Ser Met Pro Leu Glu Leu Ile Thr Thr Ile Phe Ser Ala Ala Glu
          70                  75                  80
```

FIG. 10A

```
AAG CAG TGG ACC AAT CTA GTT AGT AAG CCA CCG CAG TTG CTT GAT GAC    348
Lys Gln Trp Thr Asn Leu Val Ser Lys Pro Pro Gln Leu Leu Asp Asp
         85                  90                  95

CAT TTA GGT CTG CAT GGG CTA GTT TTC AGG CGC ACC TTT GCA ATC AGA    396
His Leu Gly Leu His Gly Leu Val Phe Arg Arg Thr Phe Ala Ile Arg
        100                 105                 110

TGC AGT GAG GTT GGA CCT GAC CGC TCC ACA TCC ATA GTG GCT GTT ATG    444
Cys Ser Glu Val Gly Pro Asp Arg Ser Thr Ser Ile Val Ala Val Met
        115                 120                 125

AAT TAC TTG CAG GAA GCT GCA TGT AAT CAT GCG GAG AGT CTG GGA CTT    492
Asn Tyr Leu Gln Glu Ala Ala Cys Asn His Ala Glu Ser Leu Gly Leu
        130                 135                 140                 145

CTA GGA GAT GGA TTC GGT GAG ACA CTA GAG ATG AGT AGG AGA GAT CTG    540
Leu Gly Asp Gly Phe Gly Glu Thr Leu Glu Met Ser Arg Arg Asp Leu
        150                 155                 160

ATA TGG GTT GTG AGA CGC ACG CAT GTT GTT GGA ACG TAC CCT GCT        588
Ile Trp Val Val Arg Arg Thr His Val Val Gly Thr Tyr Pro Ala
        165                 170                 175
```

FIG. 10B

TGG GGC GAT ACT GTT GAA GTC GAG GCC TGG ATC GGT GCA GCT GGA AAC 636
Trp Gly Asp Thr Val Glu Val Glu Ala Trp Ile Gly Ala Ala Gly Asn
           180                 185                 190

ATT GGC ATG CGC CGC CAT TTT CTT GTC CGC GAC TGC AAA ACT GGC CAC 684
Ile Gly Met Arg Arg His Phe Leu Val Arg Asp Cys Lys Thr Gly His
           195                 200                 205

ATT CTT GCA AGA TGT ACC AGT GTT TCA GTG ATG ATG AAT ATG AGG ACA 732
Ile Leu Ala Arg Cys Thr Ser Val Ser Val Met Met Asn Met Arg Thr
           210                 215                 220                 225

AGG AGA TTG TCC AAA ATT CCC CAA GAA GTT AGA GGG GAG ATT GAC CCT 780
Arg Arg Leu Ser Lys Ile Pro Gln Glu Val Arg Gly Glu Ile Asp Pro
           230                 235                 240

CTT TTC ATC GAA AAG TTT GCT GTC AAG GAA GGG GAA ATT AAG AAA TTA 828
Leu Phe Ile Glu Lys Phe Ala Val Lys Glu Gly Glu Ile Lys Lys Leu
           245                 250                 255

CAG AAG TTC AAT GAT AGC ACT GCA GAT TAC ATT CAA GGG GGT TGG ACT 876
Gln Lys Phe Asn Asp Ser Thr Ala Asp Tyr Ile Gln Gly Gly Trp Thr
           260                 265                 270

FIG. 10C

| | | | | | | | | | | | | | | | | |
|---|---|---|---|---|---|---|---|---|---|---|---|---|---|---|---|---|
|CCG|CGA|TGG|AAT|GAT|TTG|GAT|GTC|AAT|CAG|CAC|GTG|AAC|AAT|ATC|AAA|924|
|Pro|Arg|Trp|Asn|Asp|Leu|Asp|Val|Asn|Gln|His|Val|Asn|Asn|Ile|Lys| |
|275| | | |280| | | | |285| | | | | | | |

|TAC|GTT|GGC|TGG|ATT|TTT|AAG|AGC|GTC|CCA|GAC|TCT|ATC|TAT|GAG|AAT|972|
|Tyr|Val|Gly|Trp|Ile|Phe|Lys|Ser|Val|Pro|Asp|Ser|Ile|Tyr|Glu|Asn| |
|290| | | |295| | | |300| | | | |305| | | |

|CAT|CAT|CTT|TCT|AGC|ATC|ACT|CTC|GAA|TAC|AGG|AGA|GAG|TGC|ACA|AGG|1020|
|His|His|Leu|Ser|Ser|Ile|Thr|Leu|Glu|Tyr|Arg|Arg|Glu|Cys|Thr|Arg| |
| | | |310| | | | |315| | | | |320| | | |

|GGC|AGA|GCA|CTG|CAG|TCC|CTG|ACC|ACT|GTT|TGT|GGT|GGC|TCG|TCC|GAA|1068|
|Gly|Arg|Ala|Leu|Gln|Ser|Leu|Thr|Thr|Val|Cys|Gly|Gly|Ser|Ser|Glu| |
|325| | | | |330| | | | |335| | | | | | |

|GCT|GGG|ATC|ATA|TGT|GAG|CAC|CTA|CTC|CAG|CTT|GAG|GAT|GGG|TCT|GAG|1116|
|Ala|Gly|Ile|Ile|Cys|Glu|His|Leu|Leu|Gln|Leu|Glu|Asp|Gly|Ser|Glu| |
|340| | | | |345| | | | |350| | | | | | |

|GTT|TTG|AGG|GGA|AGA|ACA|GAT|TGG|AGG|CCC|AAG|CGC|ACC|GAT|AGT|TTC|1164|
|Val|Leu|Arg|Gly|Arg|Thr|Asp|Trp|Arg|Pro|Lys|Arg|Thr|Asp|Ser|Phe| |
|355| | | | |360| | | | |365| | | | | | |

FIG. 10D

```
GAA GGC ATT AGT GAG AGA TTC CCG CAG CAA GAA CCG CAT AAT TAAT       1210
Glu Gly Ile Ser Glu Arg Phe Pro Gln Gln Glu Pro His Asn
370                 375                 380

GACAGAAGCA TCAGATATAG TTTCTCCTGT GCTGTTCCTG AGAATGCATC TTACAAGTCG  1270

TGGTTTGGAT TGCTTGTGCA GAATCATGGT TTGTGCTTTC AGAAGTATAT CTAAATTAGT  1330

CCAAGTTATA TGACTCCATA TTGGAAAATA ACTCAATGAG TCGTGCTCTT GAAATGGTCT  1390

TTTAAGCTTT GAAATAAAGT TCCACTTAAT CCATGTAAAA AAAAA                  1435
```

FIG. 10E

```
                                                                              55
GCTCGCCTCC CACATTTCT TCTTCGATCC CGAAAAG ATG TTG AAG CTC TCG TGT
                                          Met Leu Lys Leu Ser Cys
                                           1                   5

AAT GCG ACT GAT AAG TTA CAG ACC CTC TTC TCG CAT TCT CAT CAA CCG              103
Asn Ala Thr Asp Lys Leu Gln Thr Leu Phe Ser His Ser His Gln Pro
            10                      15                      20

GAT CCG GCA CAC CGG AGA ACC GTC TCC TCC GTG TCG TGC TCT CAT CTG              151
Asp Pro Ala His Arg Arg Thr Val Ser Ser Val Ser Cys Ser His Leu
            25                      30                      35

AGG AAA CCG GTT CTC GAT CCT TTG CGA GCG ATC GTA TCT GCT GAT CAA              199
Arg Lys Pro Val Leu Asp Pro Leu Arg Ala Ile Val Ser Ala Asp Gln
            40                      45                      50

GGA AGT GTG ATT CGA GCA GAA CAA GGT TTG GGC TCA CTC GCG GAT CAG              247
Gly Ser Val Ile Arg Ala Glu Gln Gly Leu Gly Ser Leu Ala Asp Gln
            55                      60                      65                70

CTC CGA TTG GGT AGC TTG ACG GAG GAT GGT TTG TCG TAT AAG GAG AAG              295
Leu Arg Leu Gly Ser Leu Thr Glu Asp Gly Leu Ser Tyr Lys Glu Lys
            75                      80                      85

TTC ATC GTC AGA TCC TAC GAA GTG GGG AGT AAC AAG ACC GCC ACT GTC              343
Phe Ile Val Arg Ser Tyr Glu Val Gly Ser Asn Lys Thr Ala Thr Val
            90                      95                     100
```

```
GAA ACC GTC GCT AAT CTT TTG CAG GAG GTG GGA TGT AAT CAT GCG CAG    391
Glu Thr Val Ala Asn Leu Leu Gln Glu Val Gly Cys Asn His Ala Gln
            105                 110                 115

AGC GTT GGA TTC TCG ACT GAT GGG TTT GCG ACA ACA CCG ACC ATG AGG    439
Ser Val Gly Phe Ser Thr Asp Gly Phe Ala Thr Thr Pro Thr Met Arg
        120                 125                 130

AAA CTG CAT CTC ATT TGG GTC ACT GCG AGA ATG CAT ATA GAG ATC TAC    487
Lys Leu His Leu Ile Trp Val Thr Ala Arg Met His Ile Glu Ile Tyr
135                 140                 145                 150

AAG TAC CCT GCT TGG GGT GAT GTG GTT GAG ATA GAG ACA TGG TGT CAG    535
Lys Tyr Pro Ala Trp Gly Asp Val Val Glu Ile Glu Thr Trp Cys Gln
            155                 160                 165

AGT GAA GGA AGG ATC GGG ACT AGG CGT GAT TGG ATT CTT AAG GAT GTT    583
Ser Glu Gly Arg Ile Gly Thr Arg Arg Asp Trp Ile Leu Lys Asp Val
        170                 175                 180

GCT ACG GGT GAA GTC ACT GGC CGT GCT ACA AGC AAG TGG GTG ATG ATG    631
Ala Thr Gly Glu Val Thr Gly Arg Ala Thr Ser Lys Trp Val Met Met
185                 190                 195

AAC CAA GAC ACA AGA CGG CTT CAG AAA GTT TCT GAT GAT GTT CGG GAC    679
Asn Gln Asp Thr Arg Arg Leu Gln Lys Val Ser Asp Asp Val Arg Asp
200                 205                 210
```

| | | | | | | | | | | | | | | | |
|---|---|---|---|---|---|---|---|---|---|---|---|---|---|---|---|
| GAG | TAC | TTG | GTC | TTC | TGT | CCT | AAA | GAA | CTC | AGA | TTA | GCA | TTT | CCT | GAG |
| Glu | Tyr | Leu | Val | Phe | Cys | Pro | Lys | Glu | Leu | Arg | Leu | Ala | Phe | Pro | Glu |
| 215 | | | | | 220 | | | | | 225 | | | | | 230 |

727

| | | | | | | | | | | | | | | | |
|---|---|---|---|---|---|---|---|---|---|---|---|---|---|---|---|
| GAG | AAT | AAC | AGA | AGC | TTG | AAG | AAA | ATT | CCG | AAA | CTC | GAA | GAT | CCA | GCT |
| Glu | Asn | Asn | Arg | Ser | Leu | Lys | Lys | Ile | Pro | Lys | Leu | Glu | Asp | Pro | Ala |
| | | 235 | | | | | 240 | | | | | 245 | | | |

775

| | | | | | | | | | | | | | | | |
|---|---|---|---|---|---|---|---|---|---|---|---|---|---|---|---|
| CAG | TAT | TCG | ATG | ATT | GGG | CTT | AAG | CCT | AGA | CGA | GCT | GAT | CTC | GAC | ATG |
| Gln | Tyr | Ser | Met | Ile | Gly | Leu | Lys | Pro | Arg | Arg | Ala | Asp | Leu | Asp | Met |
| | 250 | | | | | 255 | | | | | 260 | | | | |

823

| | | | | | | | | | | | | | | | |
|---|---|---|---|---|---|---|---|---|---|---|---|---|---|---|---|
| AAC | CAG | CAT | GTC | AAT | AAT | GTC | ACC | TAT | ATT | GGA | TGG | GTT | CTT | GAG | AGC |
| Asn | Gln | His | Val | Asn | Asn | Val | Thr | Tyr | Ile | Gly | Trp | Val | Leu | Glu | Ser |
| 265 | | | | | 270 | | | | | 275 | | | | | |

871

| | | | | | | | | | | | | | | | |
|---|---|---|---|---|---|---|---|---|---|---|---|---|---|---|---|
| ATA | CCT | CAA | GAG | ATT | GTA | GAC | ACG | CAC | GAA | CTT | CAG | GTC | ATA | ACT | CTG |
| Ile | Pro | Gln | Glu | Ile | Val | Asp | Thr | His | Glu | Leu | Gln | Val | Ile | Thr | Leu |
| | 280 | | | | | 285 | | | | | 290 | | | | |

919

| | | | | | | | | | | | | | | | |
|---|---|---|---|---|---|---|---|---|---|---|---|---|---|---|---|
| GAT | TAC | AGA | AGA | GAA | TGT | CAA | CAA | GAC | GAT | GTG | GTG | GAT | TCA | CTC | ACC |
| Asp | Tyr | Arg | Arg | Glu | Cys | Gln | Gln | Asp | Asp | Val | Val | Asp | Ser | Leu | Thr |
| 295 | | | | | 300 | | | | | 305 | | | | | 310 |

967

| | | | | | | | | | | | | | | | |
|---|---|---|---|---|---|---|---|---|---|---|---|---|---|---|---|
| ACT | ACC | TCA | GAG | ATT | GGT | GGG | ACC | AAT | GGC | TCT | GCA | TCA | TCA | GGC | |
| Thr | Thr | Ser | Glu | Ile | Gly | Gly | Thr | Asn | Gly | Ser | Ala | Ser | Ser | Gly | |
| | | 315 | | | | | 320 | | | | | 325 | | | |

```
ACA CAG GGG CAA AAC GAT AGC CAG TTC TTA CAT CTC TTA AGG CTG TCT   1063
Thr Gln Gly Gln Asn Asp Ser Gln Phe Leu His Leu Leu Arg Leu Ser
                330                 335                 340

GGA GAC GGT CAG GAG ATC AAC CGC GGG ACA ACC CTG TGG AGA AAG AAG   1111
Gly Asp Gly Gln Glu Ile Asn Arg Gly Thr Thr Leu Trp Arg Lys Lys
            345                 350                 355

CCC TCC AAT CTC TAAGCCATTT CGTTCTTAAG TTTCCTCTAT CTGTGTCGCT        1163
Pro Ser Asn Leu
        360

CGATGCTTCA CGAGTCTAGT CAGGTCTCAT TTTTTTCAAT CTAAATTTGG GTTAGACTAG  1223

AGAACTGGAA TTATTGGAAT TTATGAGTTT TCGTTCTTGT TTCTGTACAA ATCTTGAGGA  1283

TTGAAGCCAA ACCCATTTCA TCTT                                         1307
```

FIG. 11D

```
                    20              40              60
TTGGCAGATC CAAAATGAAG CAATGCCGTC TTCTTTGCTG AATATTTTA CGGCGTTTGG
                    80              100             120
                                        *
ATAATTTAT TCTTGTTTCT TTTCATCATT TATTTGTTTC TCGCTGGTTA AGTACACTAC
                    140             160
AGGTGGTTCC CTCTACATCT TCAAG ATG GCT TCT ACT GCT GCT ACT GCT GCT
                                  Met Ala Ser Thr Ala Ala Thr Ala Ala
           180                    200                   220
                                   *
TTT TTT CCA GTT TCT TCA TCA ACA GAC TCT GTT GCC AAA CCC AAA AAT
Phe Phe Pro Val Ser Ser Ser Thr Asp Ser Val Ala Lys Pro Lys Asn
                              240                   260
ATT GGA TCT GCT GGG TTG GGA GGT CTC AAA TCG AAA TCC TCT TCT GGG
Ile Gly Ser Ala Gly Leu Gly Gly Leu Lys Ser Lys Ser Ser Ser Gly
            280                   300
                                           *
CGT TTG CAG GTT AAG GCT ACT GCC CAA GCC CCT TCT AAA ATA AAT GGT
Arg Leu Gln Val Lys Ala Thr Ala Gln Ala Pro Ser Lys Ile Asn Gly
            320                   340                   360
ACT TCG GTT GGT TTG ACA AAA CCT GTG GAA GGC CTG AAG AAT GAG GAT
Thr Ser Val Gly Leu Thr Lys Pro Val Glu Gly Leu Lys Asn Glu Asp
```

FIG. 12A

```
                              380
GAT ATG CCT TCA CCT CCC CCA AGA ACT TTT ATT AAT CAA TTA CCA GAC
Asp Met Pro Ser Pro Pro Pro Arg Thr Phe Ile Asn Gln Leu Pro Asp
                    420                                    460
                                       440                  *
TGG AGC ATG CTT CTT GCT GCC ATA ACA ACC ATA TTC TTG GCG GCA GAA
Trp Ser Met Leu Leu Ala Ala Ile Thr Thr Ile Phe Leu Ala Ala Glu
                              480                 500
                                                   *
AAA CAG TGG ATG CTG ATG ATG GAT TGG AAA CCA AGA AGG TCT GAT ATG CTT
Lys Gln Trp Met Leu Met Met Asp Trp Lys Pro Arg Arg Ser Asp Met Leu
                    520                         540
ATT GAT CCA TTT GGA ATT GGG AGA ATT GTC CAA GAT GGT CTC ATA TTC
Ile Asp Pro Phe Gly Ile Gly Arg Ile Val Gln Asp Gly Leu Ile Phe
        560                         580                 600
                                                         *
AGA CAA AAT TTT TCG ATT AGA TCC TAT GAA ATA GGT GCT GAT CGT ACT
Arg Gln Asn Phe Ser Ile Arg Ser Tyr Glu Ile Gly Ala Asp Arg Thr
                620                         640
GCC TCT ATA GAG ACA TTG ATG AAT CAT TTA CAG GAA ACA GCT CTT AAT
Ala Ser Ile Glu Thr Leu Met Asn His Leu Gln Glu Thr Ala Leu Asn
```

FIG. 12B

```
                                                          700
                                                            *
CAT GTT AAG ACT GCC GGT CTT CTT GGC GAT GGC TTT GGT GCA ACC CCA
His Val Lys Thr Ala Gly Leu Leu Gly Asp Gly Phe Gly Ala Thr Pro

740
GAG ATG TGC AAA AAG AAC CTG ATA TGG GTG GTT ACC CGA ATG CAG GTT
Glu Met Cys Lys Lys Asn Leu Ile Trp Val Val Thr Arg Met Gln Val

GTT GTA GAT CGC TAT CCT ACC TGG GGT GAT GTT GAG GTA GAT ACT
Val Val Asp Arg Tyr Pro Thr Trp Gly Asp Val Val Glu Val Asp Thr
                                                          840
 800
  *
TGG GTT AGT GCA TCT GGA AAG AAT GGT AAG ATG CGC CGT GAT TGG CTT GTC
Trp Val Ser Ala Ser Gly Lys Asn Gly Met Arg Arg Asp Trp Leu Val
                                              880
CGT GAT GGT CAA ACA GGG GAA ACT TTA ACA AGA GCT TCC AGT GTG TGG
Arg Asp Gly Gln Thr Gly Glu Thr Leu Thr Arg Ala Ser Ser Val Trp
                                          920                 940
 900
  *
GTG ACG ATG AAT AAA CAG ACT AGG AGA TTA TCC AAA ATT CCA GAC GAA
Val Thr Met Asn Lys Gln Thr Arg Arg Leu Ser Lys Ile Pro Asp Glu
```

FIG. 12C

```
                                         980
GTC AGG GGG GAA ATT GAG CCT TAT TTT GTG AAC TCT GAT CCT GTT GTT
Val Arg Gly Glu Ile Glu Pro Tyr Phe Val Asn Ser Asp Pro Val Val
                                      1020
GAT GAG GAT AGT AGA AAA TTA CCA AAA CTT GAT GAC AAC ACA GCT GAT
Asp Glu Asp Ser Arg Lys Leu Pro Lys Leu Asp Asp Asn Thr Ala Asp
                                                        1080
TAT GTT TGC AGA GGT TTA ACT CCT CGA TGG AGT GAT TTA GAT GTC AAC
Tyr Val Cys Arg Gly Leu Thr Pro Arg Trp Ser Asp Leu Asp Val Asn
                                                  1120
CAG CAT GTT AAC AAC GTG AAG TAC ATT GGC TGG ATC CTC GAG AGT GCT
Gln His Val Asn Asn Val Lys Tyr Ile Gly Trp Ile Leu Glu Ser Ala
                                   1160                      1180
CCA CAG GCA ATC TTG GAG AGT CAT GAG CTT GCA TCC ATG ACT TTG GAG
Pro Gln Ala Ile Leu Glu Ser His Glu Leu Ala Ser Met Thr Leu Glu
                             1200                          1220
TAT CGG AGG GAG TGT GGG AAG GAC AGT GTG TTG CAG TCC CTT ACT GCT
Tyr Arg Arg Glu Cys Gly Lys Asp Ser Val Leu Gln Ser Leu Thr Ala
```

FIG. 12D

```
                                        1260
GTC TCC AGC TCT GAT AAC GGG AAT TTG GCC CTC TCT GGT GGT GCA GAG
Val Ser Ser Asp Asn Gly Asn Leu Ala Leu Ser Gly Gly Ala Glu
    1280                                                              1320
                                *
TGC CAG CAC ATG CTA CGA CAT GAG GAC GGG CCC GAA ATA GTG AGA GGA
Cys Gln His Met Leu Arg His Glu Asp Gly Pro Glu Ile Val Arg Gly
                              1340                1360
AGG ACT GAG TGG AGG CCT AAA TAT GCA AAC AAC TTG GGG AAT GTT GGT
Arg Thr Glu Trp Arg Pro Lys Tyr Ala Asn Asn Leu Gly Asn Val Gly
                        1380                            1400
                                                                              1420
GAG GTT CCG GTA GGA AGT GCA TAAAACT TGATCTTTGT GGCAACGAGG
Glu Val Pro Val Gly Ser Ala
                  1440                     1460                    1480
CAACAGTCAC ATTCCTTGTG TAGAATCCTG CTTTTGTTCC TGGATGATTT ATATGCTTCT
                        1500                       1520                      1540
                         *
TTATATATAA TGCCTTATTT GTCTCACTTG GTGTAAGTTG AATGTAATTA GCCCTGCTGA
                       1560                     1580                      1600
                                                                             *
AATCTCGTTA TTACTCTCAT CTCAACCCAA CCAATTCAAC TAGCTCTCTT CCCAGGATGC
```

FIG. 12E

```
                      1620                    1640                                    1660
AGTGCAAAGA TAAATGACTT GTATAGGGGG AAATTTAAGG GTCTCTTGTG TTTGTCCTTG
           1680                    1700                                    1720
                                     *
CCTAACCTGT TGACGGGTGT TAAAAGCTTG GTGTTACTCA AGATCTTTCG TTGAACATGA
           1740                    1760                                    1780
TAATGTATAC TTTAGTGGCT TTTCTTTTTT CTGGTTAGAT TGGGCAAAAA ATTATGCTGG
           1800                    1820                                    1840
             *
TGGGTTTGTG CTTCATATTT TTAGCTGTAG GGGAAGGCAA TAATGATCCT TATATATATA

TATATATATT TTTGT
```

FIG. 12F

| NO | SAMPLE | %8:0 | %10:0 | %12:0 | %14:0 | %16:0 | %16:1 | %18:0 | %18:1 | %18:2 | %18:3 | %20:0 | %20:1 | %20:2 | %22:0 |
|---|---|---|---|---|---|---|---|---|---|---|---|---|---|---|---|
| 1 | 4800-1 | 0.00 | 0.70 | 0.07 | 0.90 | 13.59 | 0.71 | 2.45 | 51.18 | 18.23 | 9.83 | 0.75 | 1.10 | 0.10 | 0.37 |
| 2 | 4800-2 | 0.00 | 1.08 | 0.03 | 0.93 | 26.51 | 0.81 | 2.19 | 35.56 | 20.59 | 10.37 | 0.70 | 0.80 | 0.07 | 0.36 |
| 3 | 4800-3 | 0.00 | 1.18 | 0.05 | 0.54 | 15.53 | 0.97 | 1.83 | 44.16 | 21.06 | 12.63 | 0.61 | 1.01 | 0.09 | 0.36 |
| 4 | 4800-4 | 0.00 | 0.79 | 0.04 | 1.08 | 26.74 | 0.61 | 2.36 | 37.85 | 18.05 | 10.49 | 0.76 | 0.81 | 0.07 | 0.36 |
| 5 | 4800-5 | 0.00 | 0.88 | 0.03 | 0.21 | 8.53 | 1.00 | 1.80 | 48.72 | 23.55 | 13.43 | 0.53 | 0.91 | 0.07 | 0.32 |
| 6 | 4800-7 | 0.00 | 0.78 | 0.03 | 0.69 | 21.30 | 0.72 | 2.16 | 42.53 | 19.28 | 10.65 | 0.63 | 0.86 | 0.07 | 0.31 |
| 7 | 4800-8 | 0.00 | 0.92 | 0.04 | 0.31 | 8.23 | 1.13 | 1.80 | 43.63 | 26.76 | 15.94 | 0.33 | 0.67 | 0.07 | 0.17 |
| 8 | 4800-9 | 0.00 | 1.22 | 0.02 | 0.68 | 23.22 | 0.95 | 1.93 | 34.34 | 23.90 | 11.91 | 0.64 | 0.73 | 0.08 | 0.35 |
| 9 | 4800-10 | 0.00 | 1.15 | 0.03 | 0.21 | 7.82 | 0.95 | 1.72 | 51.02 | 21.62 | 13.66 | 0.49 | 0.97 | 0.08 | 0.27 |
| 10 | 4800-12 | 0.00 | 0.71 | 0.03 | 0.21 | 7.66 | 0.87 | 1.65 | 50.34 | 22.79 | 13.90 | 0.50 | 1.00 | 0.08 | 0.28 |
| 11 | 4800-13 | 0.00 | 0.86 | 0.03 | 0.85 | 25.18 | 0.77 | 2.00 | 34.69 | 19.96 | 13.64 | 0.69 | 0.85 | 0.08 | 0.42 |
| 12 | 4800-14 | 0.00 | 0.74 | 0.03 | 0.39 | 13.91 | 0.77 | 1.64 | 46.23 | 20.83 | 13.53 | 0.57 | 0.96 | 0.09 | 0.31 |
| 13 | 4800-15 | 0.00 | 1.54 | 0.04 | 0.53 | 15.21 | 1.63 | 3.13 | 40.96 | 22.48 | 12.39 | 0.92 | 0.64 | 0.07 | 0.46 |
| 14 | 4800-16 | 0.00 | 0.67 | 0.02 | 0.45 | 15.91 | 0.78 | 1.97 | 47.15 | 20.06 | 11.02 | 0.64 | 0.94 | 0.06 | 0.34 |
| 15 | 4800-18 | 0.00 | 0.64 | 0.02 | 0.54 | 17.13 | 0.69 | 1.95 | 45.90 | 18.87 | 12.35 | 0.59 | 0.96 | 0.06 | 0.29 |
| 16 | 4800-19 | 0.00 | 0.68 | 0.05 | 1.07 | 23.35 | 1.86 | 2.72 | 37.63 | 20.22 | 10.51 | 0.89 | 0.55 | 0.05 | 0.42 |
| 17 | 4800-20 | 0.00 | 0.70 | 0.03 | 0.41 | 14.82 | 0.74 | 1.82 | 46.86 | 20.22 | 12.64 | 0.52 | 0.93 | 0.08 | 0.23 |
| 18 | 4800-21 | 0.00 | 0.75 | 0.09 | 0.41 | 13.90 | 0.67 | 1.82 | 49.84 | 17.96 | 12.49 | 0.57 | 1.10 | 0.09 | 0.30 |
| 19 | 4800-22 | 0.00 | 0.61 | 0.02 | 0.38 | 13.48 | 0.73 | 1.77 | 46.04 | 22.09 | 12.96 | 0.58 | 0.96 | 0.09 | 0.29 |
| 20 | 4800-23 | 0.00 | 0.69 | 0.02 | 0.41 | 13.58 | 0.73 | 1.79 | 45.32 | 21.54 | 13.72 | 0.64 | 1.07 | 0.10 | 0.38 |
| 21 | 4800-24 | 0.00 | 0.37 | 0.04 | 0.94 | 21.29 | 0.57 | 2.11 | 41.00 | 18.34 | 13.40 | 0.63 | 0.94 | 0.07 | 0.28 |
| 22 | 4800-25 | 0.00 | 1.29 | 0.03 | 0.34 | 11.77 | 1.09 | 1.65 | 43.25 | 25.82 | 13.01 | 0.53 | 0.86 | 0.08 | 0.29 |
| 23 | 4800-26 | 0.00 | 0.56 | 0.05 | 0.21 | 6.77 | 0.77 | 1.79 | 52.68 | 20.80 | 14.51 | 0.49 | 1.06 | 0.09 | 0.22 |
| 24 | 4800-27 | 0.00 | 1.11 | 0.04 | 0.87 | 20.01 | 0.82 | 1.93 | 40.85 | 20.10 | 12.43 | 0.60 | 0.86 | 0.08 | 0.31 |
| 25 | 4800-28 | 0.00 | 0.69 | 0.04 | 0.73 | 19.48 | 0.66 | 1.83 | 43.43 | 18.88 | 12.30 | 0.62 | 0.94 | 0.08 | 0.31 |
| 26 | 4800-29 | 0.00 | 1.29 | 0.04 | 0.42 | 14.53 | 0.82 | 2.00 | 45.68 | 21.45 | 11.75 | 0.62 | 0.99 | 0.08 | 0.35 |
| 27 | 4800-30 | 0.00 | 0.83 | 0.03 | 0.54 | 16.85 | 0.77 | 1.74 | 44.69 | 20.62 | 12.03 | 0.58 | 0.93 | 0.08 | 0.31 |
| 28 | 4800-11 | 0.00 | 1.18 | 0.03 | 0.48 | 16.16 | 0.87 | 1.94 | 43.37 | 22.03 | 11.99 | 0.62 | 0.88 | 0.08 | 0.35 |

FIG. 13

| NO | SAMPLE | %8:0 | %10:0 | %12:0 | %14:0 | %16:0 | %16:1 | %18:0 | %18:1 | %18:2 | %18:3 | %20:0 | %20:1 | %20:2 | %22:0 |
|----|--------|------|-------|-------|-------|-------|-------|-------|-------|-------|-------|-------|-------|-------|-------|
| 1  | 4803-8  | 0.00 | 1.60 | 0.43 | 5.13 | 24.31 | 0.97 | 3.89 | 34.00 | 19.33 | 7.75 | 1.18 | 0.87 | 0.07 | 0.47 |
| 2  | 4803-9  | 0.00 | 1.49 | 0.44 | 5.04 | 20.64 | 1.05 | 2.22 | 35.32 | 22.36 | 9.27 | 0.86 | 0.78 | 0.05 | 0.47 |
| 3  | 4803-10 | 0.00 | 3.05 | 1.19 | 10.87 | 28.97 | 0.58 | 2.52 | 25.91 | 15.19 | 9.92 | 0.75 | 0.73 | 0.07 | 0.25 |
| 4  | 4803-11 | 0.00 | 2.24 | 0.61 | 5.63 | 21.16 | 0.96 | 2.53 | 36.18 | 19.62 | 8.80 | 0.90 | 0.85 | 0.08 | 0.45 |
| 5  | 4803-12 | 0.00 | 4.06 | 1.53 | 13.44 | 32.24 | 0.67 | 3.01 | 20.80 | 14.85 | 7.21 | 1.05 | 0.61 | 0.07 | 0.45 |
| 6  | 4803-14 | 0.00 | 3.89 | 1.41 | 11.60 | 29.13 | 0.59 | 2.71 | 25.71 | 14.76 | 8.18 | 0.88 | 0.73 | 0.07 | 0.34 |
| 7  | 4803-15 | 0.00 | 2.92 | 0.85 | 7.82 | 26.29 | 0.90 | 2.98 | 27.69 | 19.99 | 8.00 | 1.17 | 0.70 | 0.10 | 0.59 |
| 8  | 4803-16 | 0.00 | 3.07 | 1.33 | 12.33 | 30.91 | 0.52 | 2.70 | 26.42 | 12.90 | 7.94 | 0.82 | 0.73 | 0.05 | 0.28 |
| 9  | 4803-17 | 0.00 | 1.63 | 0.42 | 5.51 | 24.62 | 0.77 | 2.31 | 36.23 | 16.50 | 9.79 | 0.80 | 0.94 | 0.08 | 0.38 |
| 10 | 4803-18 | 0.00 | 2.14 | 0.81 | 7.97 | 27.08 | 0.53 | 2.75 | 33.31 | 15.03 | 8.22 | 0.86 | 0.88 | 0.07 | 0.36 |
| 11 | 4803-19 | 0.00 | 2.76 | 0.63 | 4.99 | 18.58 | 0.92 | 2.61 | 39.61 | 15.55 | 11.83 | 0.93 | 1.04 | 0.08 | 0.48 |
| 12 | 4803-20 | 0.00 | 2.60 | 0.86 | 8.46 | 27.38 | 0.60 | 2.61 | 30.00 | 16.37 | 8.80 | 0.96 | 0.84 | 0.07 | 0.46 |
| 13 | 4803-21 | 0.00 | 1.27 | 0.40 | 4.95 | 20.51 | 0.55 | 2.10 | 39.72 | 16.98 | 11.38 | 0.72 | 1.01 | 0.08 | 0.32 |
| 14 | 4803-22 | 0.00 | 1.52 | 0.18 | 1.99 | 14.80 | 1.09 | 3.72 | 46.53 | 18.26 | 9.07 | 1.25 | 0.89 | 0.06 | 0.62 |
| 15 | 4803-23 | 0.00 | 2.65 | 0.45 | 3.65 | 18.78 | 0.88 | 3.17 | 41.45 | 17.37 | 8.99 | 1.14 | 0.87 | 0.06 | 0.56 |
| 16 | 4803-27 | 0.00 | 2.91 | 0.51 | 3.68 | 18.11 | 0.91 | 3.19 | 40.29 | 18.03 | 9.73 | 1.13 | 0.88 | 0.08 | 0.57 |

FIGURE 14

| SAMPLE | %8:0 | %10:0 | %12:0 | %14:0 | %16:0 | %16:1 | %18:0 | %18:1 | %18:2 | %18:3 | %20:0 | %20:1 | %20:2 | %22:0 | %22:1 | %22:2 | %TSAT |
|---|---|---|---|---|---|---|---|---|---|---|---|---|---|---|---|---|---|
| 212/86 | 0.00 | 0.65 | 0.05 | 0.14 | 6.81 | 0.85 | 1.44 | 53.42 | 21.68 | 13.98 | 0.12 | 0.75 | 0.04 | 0.06 | 0.03 | 0.00 | 9.26 |
| 5228-3 | 0.00 | 0.69 | 0.00 | 0.19 | 10.76 | 1.02 | 1.27 | 48.55 | 23.48 | 12.76 | 0.35 | 0.85 | 0.05 | 0.00 | 0.00 | 0.03 | 13.26 |
| 5228-5 | 0.00 | 0.99 | 0.00 | 0.31 | 10.69 | 0.78 | 1.83 | 47.31 | 23.12 | 14.38 | 0.37 | 0.18 | 0.00 | 0.00 | 0.05 | 0.00 | 14.19 |
| 5228-11 | 0.00 | 0.71 | 0.00 | 0.20 | 8.34 | 0.80 | 1.85 | 49.78 | 22.86 | 13.90 | 0.55 | 0.68 | 0.00 | 0.34 | 0.00 | 0.00 | 11.98 |
| 5228-12 | 0.00 | 0.25 | 0.00 | 0.56 | 16.29 | 0.55 | 2.13 | 43.00 | 23.67 | 12.12 | 0.63 | 0.65 | 0.02 | 0.13 | 0.00 | 0.00 | 19.99 |
| 5228-13 | 0.00 | 0.50 | 0.00 | 0.29 | 9.07 | 0.96 | 1.69 | 50.98 | 22.17 | 12.90 | 0.55 | 0.79 | 0.03 | 0.07 | 0.00 | 0.00 | 12.17 |
| 5228-14 | 0.00 | 0.14 | 0.00 | 0.28 | 15.52 | 0.86 | 1.80 | 44.49 | 21.09 | 14.31 | 0.66 | 0.72 | 0.00 | 0.14 | 0.00 | 0.00 | 18.53 |
| 5228-16 | 0.00 | 0.12 | 0.00 | 0.22 | 8.31 | 0.65 | 1.41 | 47.73 | 23.54 | 16.38 | 0.49 | 0.89 | 0.03 | 0.22 | 0.02 | 0.00 | 10.77 |
| 5228-17 | 0.00 | 0.55 | 0.00 | 0.22 | 9.35 | 1.00 | 1.53 | 51.79 | 20.83 | 13.57 | 0.38 | 0.67 | 0.03 | 0.02 | 0.04 | 0.00 | 12.06 |
| 5228-18 | 0.00 | 0.54 | 0.00 | 0.33 | 12.27 | 0.92 | 1.62 | 49.22 | 21.35 | 12.37 | 0.52 | 0.85 | 0.00 | 0.00 | 0.00 | 0.00 | 15.28 |
| 5228-24 | 0.00 | 1.25 | 0.00 | 0.00 | 7.57 | 0.46 | 1.14 | 51.65 | 21.85 | 14.66 | 0.15 | 1.08 | 0.00 | 0.11 | 0.06 | 0.00 | 10.22 |
| 5228-19 | 0.00 | 0.46 | 0.00 | 0.30 | 11.83 | 0.94 | 1.80 | 50.53 | 20.25 | 12.09 | 0.57 | 1.09 | 0.01 | 0.11 | 0.02 | 0.00 | 15.07 |
| 5228-25 | 0.00 | 0.97 | 0.00 | 0.31 | 11.25 | 0.92 | 1.74 | 46.48 | 23.42 | 13.80 | 0.44 | 0.58 | 0.00 | 0.03 | 0.06 | 0.00 | 14.74 |
| 5228-20 | 0.00 | 0.64 | 0.00 | 0.16 | 9.67 | 0.83 | 1.53 | 48.52 | 24.12 | 12.95 | 0.48 | 0.92 | 0.00 | 0.13 | 0.03 | 0.00 | 12.62 |
| 5228-23 | 0.00 | 0.63 | 0.00 | 0.24 | 10.06 | 0.81 | 1.65 | 45.37 | 26.76 | 12.84 | 0.49 | 0.87 | 0.09 | 0.12 | 0.00 | 0.08 | 13.18 |

FIGURE 15

SEQUENCE LISTING ( 1 ) GENERAL INFORMATION:

( i i i ) NUMBER OF SEQUENCES: 33

( 2 ) INFORMATION FOR SEQ ID NO: 1:

( i ) SEQUENCE CHARACTERISTICS:
( A ) LENGTH: 1745 base pairs
( B ) TYPE: nucleic acid
( C ) STRANDEDNESS: double
( D ) TOPOLOGY: linear ( i i ) MOLECULE TYPE: cDNA to mRNA ( x i ) SEQUENCE DESCRIPTION: SEQ ID NO: 1:

```
CCAACCCCAA CTCCAACTCC GAACTGATGT TGGACCATGG CAGCCTCGTA ATTTATGGCA        60

AAACCTAGTG TCATTTACTT TGTCACGGCA CAACCTCGGT CCCATCGACA AAATCAAACA       120

TACACTTTAA ATACTAAGGC AGTCGCACGG CTCCTCGTCT CTGTATCTCT CTCTCACGAT       180

TCTACAGAGA TAACTATATT GCTCCGGCGA GCCTTTGTTT TTGTTTCAGC TTTACATAGA       240

ACAACAGAAC ATG TCG CAG TTT ACA TGC AAT GTC ACG GAC CAA ATT CAC         289
            Met Ser Gln Phe Thr Cys Asn Val Thr Asp Gln Ile His
              1               5                  10

ATT CGA AAC CAG CCC CAA TGC AGA TTC ATG GGC CTT CCG AAG CCT GTA         337
Ile Arg Asn Gln Pro Gln Cys Arg Phe Met Gly Leu Pro Lys Pro Val
     15                  20                  25

TCC TCT TTT CGC CGA CGA AAC GAT GTC GTT TCT TCT TCC CTT CCG ATT         385
Ser Ser Phe Arg Arg Arg Asn Asp Val Val Ser Ser Ser Leu Pro Ile
 30                  35                  40                  45

CCT AAA CCT CGA AAT CCG GTC AAA ATT CAG GCT GTA GTA TCG GAA CAC         433
Pro Lys Pro Arg Asn Pro Val Lys Ile Gln Ala Val Val Ser Glu His
                  50                  55                  60

GGA GGT CCA GCT GTC ACC GAC ACT GGG TCT GGT ACG TTG GCG GAC AGA         481
Gly Gly Pro Ala Val Thr Asp Thr Gly Ser Gly Thr Leu Ala Asp Arg
             65                  70                  75

CTC CGT TTA GGG AGC TTA ACG GAA GAT GGA TTG TCC TAT AAG GAG AAG         529
Leu Arg Leu Gly Ser Leu Thr Glu Asp Gly Leu Ser Tyr Lys Glu Lys
         80                  85                  90

TTT ATA GTG AGA TGT TAT GAG GTT GGG ATT AAC AAA ACT GCC ACG GTT         577
Phe Ile Val Arg Cys Tyr Glu Val Gly Ile Asn Lys Thr Ala Thr Val
     95                 100                 105

GAA ACC ATT GCT AAT CTC CTG CAG GAG GTT GGA TGT AAC CAT GCT CAA         625
Glu Thr Ile Ala Asn Leu Leu Gln Glu Val Gly Cys Asn His Ala Gln
110                 115                 120                 125

AGT GTT GGA TTT TCA ACG GAT GGA TTT GCA ACA ACC CCC ACC ATG AGA         673
Ser Val Gly Phe Ser Thr Asp Gly Phe Ala Thr Thr Pro Thr Met Arg
                130                 135                 140

AAA TTC AAT CTT ATA TGG GTG ACG GCT CGG ATG CAT ATT GAA ATC TTA         721
Lys Phe Asn Leu Ile Trp Val Thr Ala Arg Met His Ile Glu Ile Leu
            145                 150                 155

AAA TAT CCA GCT TGG AGT GAT GTG GTT GAA ATC GAA ACA TGG TGT CAT         769
Lys Tyr Pro Ala Trp Ser Asp Val Val Glu Ile Glu Thr Trp Cys His
        160                 165                 170

AGT GAA GGC AGA ATT GGA ACT AGA CGT GAT TGG ATT ATA AAA GAC TAT         817
Ser Glu Gly Arg Ile Gly Thr Arg Arg Asp Trp Ile Ile Lys Asp Tyr
    175                 180                 185

GCC ACT GGT CAA GTT ATT GGA AGA GCA ACA AGC AAG TGG GTG ATG ATG         865
Ala Thr Gly Gln Val Ile Gly Arg Ala Thr Ser Lys Trp Val Met Met
190                 195                 200                 205
```

| | | | | | | | | | | | | | | | | |
|---|---|---|---|---|---|---|---|---|---|---|---|---|---|---|---|---|
| AAC | ACG | GTC | ACT | AGG | CGG | CTA | CAG | AAA | GCC | AGT | GAT | GAA | GTT | CGA | GAA | 913 |
| Asn | Thr | Val | Thr | Arg 210 | Arg | Leu | Gln | Lys | Ala 215 | Ser | Asp | Glu | Val | Arg 220 | Glu | |
| GAA | TAT | TTA | GTT | TTC | TGT | CCA | CGA | GAA | CCC | AGA | TAC | TCT | TTT | CCA | GAG | 961 |
| Glu | Tyr | Leu | Val 225 | Phe | Cys | Pro | Arg | Glu 230 | Pro | Arg | Tyr | Ser | Phe 235 | Pro | Glu | |
| AAG | GAC | AAT | GCC | AGC | CTG | AGG | AAA | ATT | TCT | AAA | CTC | GAA | GAT | CCT | GCT | 1009 |
| Lys | Asp | Asn 240 | Ala | Ser | Leu | Arg | Lys 245 | Ile | Ser | Lys | Leu | Glu 250 | Asp | Pro | Ala | |
| GAG | TAT | TCC | AGG | ACA | GGG | CTT | ATG | CCT | AGG | AGA | GCT | GAT | CTT | GAC | ATG | 1057 |
| Glu | Tyr | Ser 255 | Arg | Thr | Gly | Leu | Met 260 | Pro | Arg | Arg | Ala 265 | Asp | Leu | Asp | Met | |
| AAC | CAG | CAC | GTT | AAC | AAT | GTT | ACC | TAC | ATT | GGA | TGG | GTT | CTA | GAG | AGC | 1105 |
| Asn 270 | Gln | His | Val | Asn 275 | Asn | Val | Thr | Tyr | Ile 280 | Gly | Trp | Val | Leu | Glu 285 | Ser | |
| ATG | CCT | CAA | GAT | ATC | ATT | GAC | ACT | CAC | GAA | CTG | CAA | ACG | ATC | ACC | TTA | 1153 |
| Met | Pro | Gln | Asp 290 | Ile | Ile | Asp | Thr | His 295 | Glu | Leu | Gln | Thr | Ile 300 | Thr | Leu | |
| GAT | TAC | AGA | CGA | GAA | TGC | CAA | CGA | GAC | GAT | ATA | GTC | GAT | TCC | CTC | ACA | 1201 |
| Asp | Tyr | Arg | Arg 305 | Glu | Cys | Gln | Arg | Asp 310 | Asp | Ile | Val | Asp | Ser 315 | Leu | Thr | |
| AGT | CCT | GAA | CTG | ATC | GAG | GAT | TCT | GAT | GCA | ATT | TCA | AAT | CTT | AAA | GGA | 1249 |
| Ser | Pro | Glu 320 | Leu | Ile | Glu | Asp | Ser 325 | Asp | Ala | Ile | Ser | Asn 330 | Leu | Lys | Gly | |
| GCA | AAT | GGG | TCT | CCT | GCA | ACA | GGA | GAC | AAA | GAA | GAC | TAC | CGT | CAA | TTT | 1297 |
| Ala | Asn 335 | Gly | Ser | Pro | Ala | Thr 340 | Gly | Asp | Lys | Glu | Asp 345 | Tyr | Arg | Gln | Phe | |
| TTG | CAC | TTG | CTG | AGA | TTG | TCA | AGC | GAT | GGC | TCT | GAA | ATA | AAC | CGA | GGT | 1345 |
| Leu 350 | His | Leu | Leu | Arg | Leu 355 | Ser | Ser | Asp | Gly | Ser 360 | Glu | Ile | Asn | Arg | Gly 365 | |
| CGC | ACT | GAG | TGG | AGA | AGG | AAA | CCT | GGT | AGA | TAAGGAAATA | | GTGTAGTTTA | | | | 1395 |
| Arg | Thr | Glu | Trp 370 | Arg | Arg | Lys | Pro | Gly | Arg 375 | | | | | | | |

```
CCCCAGTCTC  CTCTCTTCAA  TGTGTTCGGA  AAAGTTGTTT  GTTTCTGTTT  CTTTTGCCTT  1455
TCATAAGGGG  GTTTGGCTCC  AAATCTGTGT  GTTGTTGGGA  ACTTTAGAAT  CATCAGTAGA  1515
TTACGAGGCA  AATGTGTAGT  TTTTTTTCCG  GTCGGTCATC  CATCAATTGT  TGTATCTTTA  1575
CTGTTTGTAA  TTTTGTCAGA  AGCTTTCGTG  TTTATATGTA  ATGTTTCTTG  TTTGAAAAGT  1635
CCATATGGAA  TTAGATTCCT  AGTTTTCAGG  CTCTGCATTT  GGTGTAAGGT  TTGGGACTCT  1695
GTTTCGCCAA  CATGAAATTT  AACATTTTGA  AAAAAAAAAA  AAAAAAAAA               1745
```

( 2 ) INFORMATION FOR SEQ ID NO: 2:

( i ) SEQUENCE CHARACTERISTICS:
        ( A ) LENGTH: 1717 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO: 2:

```
GCAGCATCAG  GATTAGCAGA  TCCAAAATGA  AGCAATGGTG  TCTTCTTGCC  TGACTATTTT   60
TACGACGTTC  GGATAATTTA  TTCTTGCTTT  CTTCGWCAT   TTCTCTGTTT  CTCGCCGGTT  120
AAGGTGGTTC  CCTCTACATT  TTCAAG                                          173
```

| | | | | | | | | | | | |
|---|---|---|---|---|---|---|---|---|---|---|---|
| | | | | | ATG | GCT | TCT | ACT | GCT | GCT ACT GCA TGT | 173 |
| | | | | | Met 1 | Ala | Ser | Thr | Ala 5 | Ala Thr Ala Cys | |
| TTT | TTT | CCA | GTT | TCT | TCT | CCA | TCC | TCA | GAT | TCT GTT GCA AAG ACC AAG | 221 |
| Phe | Phe 10 | Pro | Val | Ser | Ser 15 | Pro | Ser | Ser | Asp 20 | Ser Val Ala Lys Thr Lys 25 | |

```
AAT ATT GGA TCT GCT AGT TTG GGA GGT ATG AAA GCC AAA TCA TCT TCT      269
Asn Ile Gly Ser Ala Ser Leu Gly Gly Met Lys Ala Lys Ser Ser Ser
            30                  35                  40

GGG GGT TTG CAG GTT AAG GCC AGT GCC CAA GCG CCT TCC AAA ATA AAT      317
Gly Gly Leu Gln Val Lys Ala Ser Ala Gln Ala Pro Ser Lys Ile Asn
            45                  50                  55

GGT ACT TCA GTT GGT TTG ACA AAA CCA TCG GAA AGC CTG AAG AAT GAG      365
Gly Thr Ser Val Gly Leu Thr Lys Pro Ser Glu Ser Leu Lys Asn Glu
            60                  65                  70

GAT GAG ATG CCT TCA TCT CAC CCA AGG ACT TTT ATT AAC CAA TTA CCC      413
Asp Glu Met Pro Ser Ser His Pro Arg Thr Phe Ile Asn Gln Leu Pro
        75                  80                  85

GAC TGG AGC ATG CTT CTT GCT GCC ATA ACA ACC ATA TTC TTG GCA GCG      461
Asp Trp Ser Met Leu Leu Ala Ala Ile Thr Thr Ile Phe Leu Ala Ala
90                  95                  100                 105

GAG AAA CAG TGG ATG ATG CTT GAC TGG AAA CCA AGA AGG TCC GAC ATG      509
Glu Lys Gln Trp Met Met Leu Asp Trp Lys Pro Arg Arg Ser Asp Met
                    110                 115                 120

CTT ATT GAT CCA TTT GGT ATT GGG AGG ATT GTT CAG GAT GGT CTG ATA      557
Leu Ile Asp Pro Phe Gly Ile Gly Arg Ile Val Gln Asp Gly Leu Ile
                125                 130                 135

TTC CGA CAA AAT TTT TCA ATT AGA TCC TAT GAG ATA GGT GCT GAT CGT      605
Phe Arg Gln Asn Phe Ser Ile Arg Ser Tyr Glu Ile Gly Ala Asp Arg
            140                 145                 150

ACT GCA TCT ATA GAG ACA TTG ATG AAT CAT TTA CAG GAG ACA GCT CTT      653
Thr Ala Ser Ile Glu Thr Leu Met Asn His Leu Gln Glu Thr Ala Leu
        155                 160                 165

AAT CAT GTT AAG AGT GCT GGT CTT CTT GGT GAT GGC TTC GGT TCA ACC      701
Asn His Val Lys Ser Ala Gly Leu Leu Gly Asp Gly Phe Gly Ser Thr
170                 175                 180                 185

CCA GGG ATG TGC AAG AAG AAT CTG ATA TGG GTG GTT ACC CGA ATG CAG      749
Pro Gly Met Cys Lys Lys Asn Leu Ile Trp Val Val Thr Arg Met Gln
                190                 195                 200

GTT GTT GTA GAT CGT TAT CCT ACC TGG GGT GAT GTT GTT GAG GTA GAT      797
Val Val Val Asp Arg Tyr Pro Thr Trp Gly Asp Val Val Glu Val Asp
                205                 210                 215

TCT TGG GTT AGT GCA TCG GGA AAG AAT GGT ATG CGC CGT GAT TGG CTT      845
Ser Trp Val Ser Ala Ser Gly Lys Asn Gly Met Arg Arg Asp Trp Leu
            220                 225                 230

GCC CGC GAT AGT AAA ACA GGG GAA ACT TTA ACA AGG GCC TCC AGT GTG      893
Ala Arg Asp Ser Lys Thr Gly Glu Thr Leu Thr Arg Ala Ser Ser Val
        235                 240                 245

TGG GTG ATG ATG AAT AAA CAG ACT AGG AGA TTA TCC AAA ATT CCA GAC      941
Trp Val Met Met Asn Lys Gln Thr Arg Arg Leu Ser Lys Ile Pro Asp
250                 255                 260                 265

GAA GTC AGA GGG GAA ATT GAG CCT TAT TTT GTA AAC TCT GAT CCT GTT      989
Glu Val Arg Gly Glu Ile Glu Pro Tyr Phe Val Asn Ser Asp Pro Val
                270                 275                 280

GTG GAT GAG GAT GGT AGG AAA TTA CCA AAA CTT GAC GAC AAC ACA GCT     1037
Val Asp Glu Asp Gly Arg Lys Leu Pro Lys Leu Asp Asp Asn Thr Ala
                285                 290                 295

GAT TAT GTT CAC AGA GGT TTA ACT CCT AGA TGG AGT GAT TTA GAT GTC     1085
Asp Tyr Val His Arg Gly Leu Thr Pro Arg Trp Ser Asp Leu Asp Val
            300                 305                 310

AAC CAG CAT GTT AAC AAT GTG AAG TAC ATT GGC TGG ATC CTT GAG AGT     1133
Asn Gln His Val Asn Asn Val Lys Tyr Ile Gly Trp Ile Leu Glu Ser
        315                 320                 325

GCT CCG CAG GCA ATC CTG GAG AGT CAC GAG CTT GCA TCT ATG ACT TTG     1181
Ala Pro Gln Ala Ile Leu Glu Ser His Glu Leu Ala Ser Met Thr Leu
330                 335                 340                 345
```

```
GAG TAT CGG AGG GAG TGT GGG AAG GAC AGT GTG TTA AAG TCT CTT ACT    1229
Glu Tyr Arg Arg Glu Cys Gly Lys Asp Ser Val Leu Lys Ser Leu Thr
            350                 355                 360

GCT GTC TCT GGT TCT GAT GTT GGC AAT TTG AGC CAC CTT GGC CGT GTC    1277
Ala Val Ser Gly Ser Asp Val Gly Asn Leu Ser His Leu Gly Arg Val
            365                 370                 375

GAG TGC CAG CAC ATG CTA CAA CTC GAG GAT GGG GCT GAA ATA GTG AGA    1325
Glu Cys Gln His Met Leu Gln Leu Glu Asp Gly Ala Glu Ile Val Arg
            380                 385                 390

GGA AGG ACT GAA TGG AGG CCT AAA TAT GCA AAC AAC TTT GGG AAT GTG    1373
Gly Arg Thr Glu Trp Arg Pro Lys Tyr Ala Asn Asn Phe Gly Asn Val
            395                 400                 405

GGT GAG GTT CCG GCT GAA AGC GCA TAAAACTTGA TCATTGTGGC TAGGAGGCCA    1427
Gly Glu Val Pro Ala Glu Ser Ala
410                 415

TGGTCACATT GCTTGTGCAG AATCCAATCC TGCTTGTGTT GGATGATTTT TATGCTTCTT    1487

TATATGTATT TACTTGTTTG TCCTACTTTA AGAAAAGCTG AAGTTCAGT GTAATTAGCC    1547

TTGCTGCAGT CTCGAATTCC TCTCAACCCT ACCAATTCAA TTAGCCCTCT TCCCACGGAT    1607

GCAATGCAAA GATGGATGAA TTATATAGAG GGAAATTCTA TGGTTGCTTA ACCTGTTGAG    1667

TTGTTAATTG TTAAGCCCTT TTATTTTCAC CTAAAAAAAA AAAAAAAAA               1717
```

( 2 ) INFORMATION FOR SEQ ID NO: 3:

( i ) SEQUENCE CHARACTERISTICS:
        ( A ) LENGTH: 1294 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO: 3:

```
C ATG GAT GCA AAA ACA CAT GCT CAA GCT GTT CCA AAA ATA AAT GGA ACA    49
  Met Asp Ala Lys Thr His Ala Gln Ala Val Pro Lys Ile Asn Gly Thr
   1               5                  10                  15

AAG GTC GAT ACA AGG AGA AAT GAT TCT TCA AGA GGG GAG GAC GAG GCT     97
Lys Val Asp Thr Arg Arg Asn Asp Ser Ser Arg Gly Glu Asp Glu Ala
            20                  25                  30

ATA TAC ACT ACT TCT TCT GCC CCT AGG ACA TTC TAT AAC CAG TTG CCT    145
Ile Tyr Thr Thr Ser Ser Ala Pro Arg Thr Phe Tyr Asn Gln Leu Pro
            35                  40                  45

GAT TGG AGC ATG TTG CTA GCT GCC ATT ACT ACT ATA TTT TTG GCA GCT    193
Asp Trp Ser Met Leu Leu Ala Ala Ile Thr Thr Ile Phe Leu Ala Ala
    50                  55                  60

GAG AAG CAA TGG ACT CTT ATT GAT TGG AAG CCT AGG CGA CCT GAT ATG    241
Glu Lys Gln Trp Thr Leu Ile Asp Trp Lys Pro Arg Arg Pro Asp Met
65              70                  75                  80

CTT TCT GAT GCG TTT GGA CTT GGA AAG ATT GTT CAA GAT GGG CTC GTG    289
Leu Ser Asp Ala Phe Gly Leu Gly Lys Ile Val Gln Asp Gly Leu Val
                85                  90                  95

TTT ACT CAG AAT TTT CCT ATA CGA TCC TAT GAG ATA GGG GCA GAT CGG    337
Phe Thr Gln Asn Phe Pro Ile Arg Ser Tyr Glu Ile Gly Ala Asp Arg
            100                 105                 110

ACG GCC TCT ATA GAG ACG TTA ATG AAT CAT TTA CAG GAA ACT GCA CTT    385
Thr Ala Ser Ile Glu Thr Leu Met Asn His Leu Gln Glu Thr Ala Leu
            115                 120                 125

AAT CAT GTG AAG ATG GCT GGG TTG TTA GGA GAT GGA TTT GGT GCG ACG    433
Asn His Val Lys Met Ala Gly Leu Leu Gly Asp Gly Phe Gly Ala Thr
130                 135                 140
```

| | | | | | | | | | | | | | | | | |
|---|---|---|---|---|---|---|---|---|---|---|---|---|---|---|---|---|
| CCT | GAA | ATG | AGT | AAA | AAG | AAT | CTA | ATT | TGG | GTT | GTT | ACG | AAG | ATG | CAG | 481 |
| Pro | Glu | Met | Ser | Lys | Lys | Asn | Leu | Ile | Trp | Val | Val | Thr | Lys | Met | Gln | |
| 145 | | | | 150 | | | | | 155 | | | | | | 160 | |
| GTC | CTT | GTA | GAA | CAC | TAT | CCT | AAA | TGG | GGA | GAT | GTG | GTT | GAA | GTC | GAT | 529 |
| Val | Leu | Val | Glu | His | Tyr | Pro | Lys | Trp | Gly | Asp | Val | Val | Glu | Val | Asp | |
| | | | | 165 | | | | | 170 | | | | | 175 | | |
| ACA | TGG | GTT | AGT | GCA | TCA | GGA | AAA | AAT | GGC | ATG | CGC | CGT | GAT | TGG | CAT | 577 |
| Thr | Trp | Val | Ser | Ala | Ser | Gly | Lys | Asn | Gly | Met | Arg | Arg | Asp | Trp | His | |
| | | | 180 | | | | | 185 | | | | | 190 | | | |
| GTT | CAT | AAC | ATC | CGA | ACT | GGC | CAA | ACT | GTC | ATG | CGA | GCC | ACA | AGC | GTT | 625 |
| Val | His | Asn | Ile | Arg | Thr | Gly | Gln | Thr | Val | Met | Arg | Ala | Thr | Ser | Val | |
| | | 195 | | | | | 200 | | | | | 205 | | | | |
| TGG | GTG | ATG | ATG | AAC | AAA | GTT | ACT | AGA | AGG | CTG | TCT | AAA | ATG | CCC | GAA | 673 |
| Trp | Val | Met | Met | Asn | Lys | Val | Thr | Arg | Arg | Leu | Ser | Lys | Met | Pro | Glu | |
| 210 | | | | | 215 | | | | | 220 | | | | | | |
| GAA | GTT | AGA | GCA | GAG | ATA | GGA | CCT | TTT | TTT | GTT | GAC | CGT | GGT | CCG | ATC | 721 |
| Glu | Val | Arg | Ala | Glu | Ile | Gly | Pro | Phe | Phe | Val | Asp | Arg | Gly | Pro | Ile | |
| 225 | | | | 230 | | | | | 235 | | | | | 240 | | |
| ATA | GAT | GAA | GAT | AGC | AGG | AAA | CTT | CCT | AAG | CTA | GAC | GAG | GAG | TCA | GCA | 769 |
| Ile | Asp | Glu | Asp | Ser | Arg | Lys | Leu | Pro | Lys | Leu | Asp | Glu | Glu | Ser | Ala | |
| | | | | 245 | | | | | 250 | | | | | 255 | | |
| AAC | CAT | GTC | AAA | AAT | GGA | TTA | ACT | CCT | CGA | TGG | AGC | GAT | TTG | GAT | GTC | 817 |
| Asn | His | Val | Lys | Asn | Gly | Leu | Thr | Pro | Arg | Trp | Ser | Asp | Leu | Asp | Val | |
| | | | 260 | | | | | 265 | | | | | 270 | | | |
| AAC | CAG | CAT | GTT | AAC | AAT | GTT | AAG | TAC | ATT | GGA | TGG | ATT | CTT | GAG | AGT | 865 |
| Asn | Gln | His | Val | Asn | Asn | Val | Lys | Tyr | Ile | Gly | Trp | Ile | Leu | Glu | Ser | |
| | | 275 | | | | | 280 | | | | | 285 | | | | |
| GCA | CCT | ATA | TCT | CTT | CTA | GAG | AGC | CAT | GAA | CTT | GCT | AGC | ATG | ACT | CTA | 913 |
| Ala | Pro | Ile | Ser | Leu | Leu | Glu | Ser | His | Glu | Leu | Ala | Ser | Met | Thr | Leu | |
| | 290 | | | | | 295 | | | | | 300 | | | | | |
| GAA | TAC | AGG | AGA | GAG | TGT | GGA | AGG | GAC | AGT | GTG | CTT | CAG | TCT | CTT | ACT | 961 |
| Glu | Tyr | Arg | Arg | Glu | Cys | Gly | Arg | Asp | Ser | Val | Leu | Gln | Ser | Leu | Thr | |
| 305 | | | | 310 | | | | | 315 | | | | | 320 | | |
| GCT | GTA | ACT | TCT | GAC | TGT | ACC | ACG | GAC | ACT | TCA | CAT | GAA | AAA | ACG | TTC | 1009 |
| Ala | Val | Thr | Ser | Asp | Cys | Thr | Thr | Asp | Thr | Ser | His | Glu | Lys | Thr | Phe | |
| | | | | 325 | | | | | 330 | | | | | 335 | | |
| ACG | GAG | TGC | AAT | CAT | CTA | CTG | CGG | CTT | GAT | TGT | GGG | GCT | GAG | ATT | GTA | 1057 |
| Thr | Glu | Cys | Asn | His | Leu | Leu | Arg | Leu | Asp | Cys | Gly | Ala | Glu | Ile | Val | |
| | | | 340 | | | | | 345 | | | | | 350 | | | |
| AGG | GGA | CAC | ACG | GAA | TGG | AGG | CCC | AAG | AAT | GCC | CAG | GAC | CTC | GCC | AAC | 1105 |
| Arg | Gly | His | Thr | Glu | Trp | Arg | Pro | Lys | Asn | Ala | Gln | Asp | Leu | Ala | Asn | |
| | | 355 | | | | | 360 | | | | | 365 | | | | |
| ATG | GGC | CCA | CCA | AGC | ATC | AAC | TGATGATGAT | | CCAGTATGAA | | AACTTCACCT | | | | | 1156 |
| Met | Gly | Pro | Pro | Ser | Ile | Asn | | | | | | | | | | |
| | 370 | | | | | 375 | | | | | | | | | | |

TATATAAGCA TTTTTACATG TGTAAATAAT CGGTTTCAAT TGTAGCGTGC CCAAAAAAAG 1216

GTAACTTGAA CTTGGGTTTG TGCTATTGTT TGCTTTTTTA TTCAGAAAGT TTAGCCTCGT 1276

GCCGCTCGTG CCGAATTC 1294

( 2 ) INFORMATION FOR SEQ ID NO: 4 :

( i ) SEQUENCE CHARACTERISTICS:
        ( A ) LENGTH: 1776 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO: 4 :

```
AACAGCTGTC ATCACAAAAC TCCGATTTAA ATTAGTTAAA CTACTATTAT ATGCGGTCAA    60

AATTGGATTT TGCCTCGATC AAATTATTTT TTACTATAGA GTTAGAAAAC ATGCATAAAT   120

AGATCCGGCC ACAGCAATTT GTCCATTAGT TTATCTTCAC ATACACTCTC TTTCTGGATT   180

CTGCTTCCAT CCCCGAAATA CATCGCGATT TACGATTCAA CCTAAATTGT TATCTCTCTA   240

GATTGTTCCC AAGTGTGGCC GCAGCTGAAC TTCTCGCGAT TTGGTTTGAA AAATTCTGAA   300

GAAGCTGCTA CTATAAGAAA TATAGTATC ATG GCT GCA TTT GCT TCC TCG GCC    353
                                Met Ala Ala Phe Ala Ser Ser Ala
                                 1               5

TTC TTC CCT ACT CCA TCC GGA CCA AAC TCG TCC TTA AAA TCC TCA AAA    401
Phe Phe Pro Thr Pro Ser Gly Pro Asn Ser Ser Leu Lys Ser Ser Lys
    10              15                  20

CCA GTA AAT GGT AAT CAA GAT TCT CTA CAA GTC AAT GGA TTA GTA TCT    449
Pro Val Asn Gly Asn Gln Asp Ser Leu Gln Val Asn Gly Leu Val Ser
25              30                  35                  40

AAA AAG AGT TTA TCA TCC AAA TCC ATG GAT GCA AAA ACA CAT GCT CAA    497
Lys Lys Ser Leu Ser Ser Lys Ser Met Asp Ala Lys Thr His Ala Gln
                45                  50                  55

GCT GTT CCA AAA ATA AAT GGA ACA AAG GTC GAT ACA AGG AGA AAT GAT    545
Ala Val Pro Lys Ile Asn Gly Thr Lys Val Asp Thr Arg Arg Asn Asp
            60                  65                  70

TCT TCA AGA GGG GAG GAC GAG GCT ATA TAC ACT ACT TCT TCT GCC CCT    593
Ser Ser Arg Gly Glu Asp Glu Ala Ile Tyr Thr Thr Ser Ser Ala Pro
        75                  80                  85

AGG ACA TTC TAT AAC CAG TTG CCT GAT TGG AGC ATG TTG CTA GCT GCC    641
Arg Thr Phe Tyr Asn Gln Leu Pro Asp Trp Ser Met Leu Leu Ala Ala
    90                  95                 100

ATT ACT ACT ATA TTT TTG GCA GCT GAG AAG CAA TGG ACT CTT ATT GAT    689
Ile Thr Thr Ile Phe Leu Ala Ala Glu Lys Gln Trp Thr Leu Ile Asp
105             110                 115                 120

TGG AAG CCT AGG CGA CCT GAT ATG CTT TCT GAT GCG TGT GGN CTT GGA    737
Trp Lys Pro Arg Arg Pro Asp Met Leu Ser Asp Ala Cys Gly Leu Gly
                125                 130                 135

AAG ATT GCA CAA GAT GGG CTC GTG TTT ACT CAG AAT TCT CCT ATA CGA    785
Lys Ile Ala Gln Asp Gly Leu Val Phe Thr Gln Asn Ser Pro Ile Arg
            140                 145                 150

TCC TAT GAG ATA GGG GCA GNT CGG ACG GCC TCT ATA GAG ACG TTA ATG    833
Ser Tyr Glu Ile Gly Ala Xxx Arg Thr Ala Ser Ile Glu Thr Leu Met
        155                 160                 165

ACT CAT TTA CAG GAA ACT GCA CTT ACT CAT GTG AAG ATG GCT GGG TTG    881
Thr His Leu Gln Glu Thr Ala Leu Thr His Val Lys Met Ala Gly Leu
    170                 175                 180

TTA GGA GAT GGC TTT GGN GCG ACG CCT GAA ATG AGT AAA AAG AAT CTA    929
Leu Gly Asp Gly Phe Gly Ala Thr Pro Glu Met Ser Lys Lys Asn Leu
185             190                 195                 200

ATT TGG GTT GTT ACG AAG ATG CAG GTC CTT GTA GAA CAC TAT CCT AAA    977
Ile Trp Val Val Thr Lys Met Gln Val Leu Val Glu His Tyr Pro Lys
                205                 210                 215

TGG GGA GAT GTG GTT GAA GTC GAT ACA TGG GTT AGT GCA TCA GGA AAA   1025
Trp Gly Asp Val Val Glu Val Asp Thr Trp Val Ser Ala Ser Gly Lys
            220                 225                 230

AAT GGC ATG CGC CGT GAT TGG CAT GTT CAT AAC ATC CGA ACT GGC CAA   1073
Asn Gly Met Arg Arg Asp Trp His Val His Asn Ile Arg Thr Gly Gln
        235                 240                 245

ACT GTC ATG CGA GCC ACA AGC GTT TGG GTG ATG ATG AAC AAA GTT ACT   1121
Thr Val Met Arg Ala Thr Ser Val Trp Val Met Met Asn Lys Val Thr
    250                 255                 260

AGA AGG CTG TCT AAA ATG CCC GAA GAA GTT AGA GCA GAG ATA GGA CCT   1169
Arg Arg Leu Ser Lys Met Pro Glu Glu Val Arg Ala Glu Ile Gly Pro
```

```
           265                      270                      275                      280
TTT  TTT  GTT  GAC  CGT  GGT  CCG  ATC  ATA  GAT  GAA  GAT  AGC  AGG  AAA  CTT   1217
Phe  Phe  Val  Asp  Arg  Gly  Pro  Ile  Ile  Asp  Glu  Asp  Ser  Arg  Lys  Leu
                    285                      290                      295

CCT  AAG  CTA  GAC  GAG  GAG  TCA  GCA  AAC  CAT  GTC  AAA  AAT  GGA  TTA  ACT   1265
Pro  Lys  Leu  Asp  Glu  Glu  Ser  Ala  Asn  His  Val  Lys  Asn  Gly  Leu  Thr
                    300                      305                      310

CCT  CGA  TGG  AGC  GAT  TTG  GAT  GTC  AAC  CAG  CAT  GTT  AAC  AAT  GTT  AAG   1313
Pro  Arg  Trp  Ser  Asp  Leu  Asp  Val  Asn  Gln  His  Val  Asn  Asn  Val  Lys
               315                      320                      325

TAC  ATT  GGA  TGG  ATT  CTT  GAG  AGT  GCA  CCT  ATA  TCT  CTT  CTA  GAG  AGC   1361
Tyr  Ile  Gly  Trp  Ile  Leu  Glu  Ser  Ala  Pro  Ile  Ser  Leu  Leu  Glu  Ser
     330                      335                      340

CAT  GAA  CTT  GCT  AGC  ATG  ACT  CTA  GAA  TAC  AGG  AGA  GAG  TGT  GGA  AGG   1409
His  Glu  Leu  Ala  Ser  Met  Thr  Leu  Glu  Tyr  Arg  Arg  Glu  Cys  Gly  Arg
345                      350                      355                      360

GAC  AGT  GTG  CTT  CAG  TCT  CTT  ACT  GCT  GTA  ACT  TCT  GAC  TGT  ACC  ACG   1457
Asp  Ser  Val  Leu  Gln  Ser  Leu  Thr  Ala  Val  Thr  Ser  Asp  Cys  Thr  Thr
                    365                      370                      375

GAC  ACT  TCA  CGT  GAA  AAA  ACG  TTC  ACG  GAG  TGC  AAT  CAT  CTT  CTG  CGG   1505
Asp  Thr  Ser  Arg  Glu  Lys  Thr  Phe  Thr  Glu  Cys  Asn  His  Leu  Leu  Arg
               380                      385                      390

CTT  GAT  TGT  GGG  GCT  GAG  ATT  GTA  AGG  GGA  CAC  ACG  GAA  TGG  AGG  CCC   1553
Leu  Asp  Cys  Gly  Ala  Glu  Ile  Val  Arg  Gly  His  Thr  Glu  Trp  Arg  Pro
               395                      400                      405

AAG  AAT  GCC  CAG  GAC  CTC  GCC  AAC  ATG  GGC  CCA  CCA  AGC  ATG  AAC  TG    1600
Lys  Asn  Ala  Gln  Asp  Leu  Ala  Asn  Met  Gly  Pro  Pro  Ser  Met  Asn
          410                      415                      420       423

ATGATGATCC  AGTATAAAAA  CGTCACCTTA  TACTACTGCG  ATATCTTGTA  TTGCGCTATA       1660

TAAGCATTTT  TACATGTGTA  AATAATCGAT  TTCGACGTAT  TTGATGGATG  TGGGGAAAAC       1720

TTGTAGCATG  CCCAAAAAAA  GTAACTTGAA  CTTGGGTTTG  TCCTCGTGCC  GAATTC           1776
```

( 2 ) INFORMATION FOR SEQ ID NO: 5:

( i ) SEQUENCE CHARACTERISTICS:
        ( A ) LENGTH: 1561 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO: 5:

```
AGAGAGAGAG  AGAGAGAGAG  AGCTAAATTA  AAAAAAAAAC  CCAGAAGTGG  GAAATCTTCC        60

CCATGAAATA  ACGGATCCTC  TTGCTACTGC  TACTACTACT  ACTACAAACT  GTAGCCATTT       120

ATATAATTCT  ATATAATTTT  CAAC ATG  GCC  ACC  ACC  TCT  TTA  GCT  TCC  GCT  TTC  174
                              Met  Ala  Thr  Thr  Ser  Leu  Ala  Ser  Ala  Phe
                              1                  5                        10

TGC  TCG  ATG  AAA  GCT  GTA  ATG  TTG  GCT  CGT  GAT  GGC  CGG  GGC  ATG  AAA   222
Cys  Ser  Met  Lys  Ala  Val  Met  Leu  Ala  Arg  Asp  Gly  Arg  Gly  Met  Lys
               15                       20                       25

CCC  AGG  AGC  AGT  GAT  TTG  CAG  CTG  AGG  GCG  GGA  AAT  GCG  CCA  ACC  TCT   270
Pro  Arg  Ser  Ser  Asp  Leu  Gln  Leu  Arg  Ala  Gly  Asn  Ala  Pro  Thr  Ser
               30                       35                       40

TTG  AAG  ATG  ATC  AAT  GGG  ACC  AAG  TTC  AGT  TAC  ACG  GAG  AGC  TTG  AAA   318
Leu  Lys  Met  Ile  Asn  Gly  Thr  Lys  Phe  Ser  Tyr  Thr  Glu  Ser  Leu  Lys
          45                       50                       55

AGG  TTG  CCT  GAC  TGG  AGC  ATG  CTC  TTT  GCA  GTG  ATC  ACA  ACC  ATC  TTT   366
Arg  Leu  Pro  Asp  Trp  Ser  Met  Leu  Phe  Ala  Val  Ile  Thr  Thr  Ile  Phe
     60                       65                       70
```

```
TCG GCT GCT GAG AAG CAG TGG ACC AAT CTA GAG TGG AAG CCG AAG CCG     414
Ser Ala Ala Glu Lys Gln Trp Thr Asn Leu Glu Trp Lys Pro Lys Pro
75              80                  85                  90

AAG CTA CCC CAG TTG CTT GAT GAC CAT TTT GGA CTG CAT GGG TTA GTT     462
Lys Leu Pro Gln Leu Leu Asp Asp His Phe Gly Leu His Gly Leu Val
            95                  100                 105

TTC AGG CGC ACC TTT GCC ATC AGA TCT TAT GAG GTG GGA CCT GAC CGC     510
Phe Arg Arg Thr Phe Ala Ile Arg Ser Tyr Glu Val Gly Pro Asp Arg
                110                 115                 120

TCC ACA TCT ATA CTG GCT GTT ATG AAT CAC ATG CAG GAG GCT ACA CTT     558
Ser Thr Ser Ile Leu Ala Val Met Asn His Met Gln Glu Ala Thr Leu
            125                 130                 135

AAT CAT GCG AAG AGT GTG GGA ATT CTA GGA GAT GGA TTC GGG ACG ACG     606
Asn His Ala Lys Ser Val Gly Ile Leu Gly Asp Gly Phe Gly Thr Thr
    140                 145                 150

CTA GAG ATG AGT AAG AGA GAT CTG ATG TGG GTT GTG AGA CGC ACG CAT     654
Leu Glu Met Ser Lys Arg Asp Leu Met Trp Val Val Arg Arg Thr His
155                 160                 165                 170

GTT GCT GTG GAA CGG TAC CCT ACT TGG GGT GAT ACT GTA GAA GTA GAG     702
Val Ala Val Glu Arg Tyr Pro Thr Trp Gly Asp Thr Val Glu Val Glu
                175                 180                 185

TGC TGG ATT GGT GCA TCT GGA AAT AAT GGC ATG CGA CGT GAT TTC CTT     750
Cys Trp Ile Gly Ala Ser Gly Asn Asn Gly Met Arg Arg Asp Phe Leu
            190                 195                 200

GTC CGG GAC TGC AAA ACA GGC GAA ATT CTT ACA AGA TGT ACC AGC CTT     798
Val Arg Asp Cys Lys Thr Gly Glu Ile Leu Thr Arg Cys Thr Ser Leu
                205                 210                 215

TCG GTG CTG ATG AAT ACA AGG ACA AGG AGG TTG TCC ACA ATC CCT GAC     846
Ser Val Leu Met Asn Thr Arg Thr Arg Arg Leu Ser Thr Ile Pro Asp
        220                 225                 230

GAA GTT AGA GGG GAG ATA GGG CCT GCA TTC ATT GAT AAT GTG GCT GTC     894
Glu Val Arg Gly Glu Ile Gly Pro Ala Phe Ile Asp Asn Val Ala Val
235                 240                 245                 250

AAG GAC GAT GAA ATT AAG AAA CTA CAG AAG CTC AAT GAC AGC ACT GCA     942
Lys Asp Asp Glu Ile Lys Lys Leu Gln Lys Leu Asn Asp Ser Thr Ala
                255                 260                 265

GAT TAC ATC CAA GGA GGT TTG ACT CCT CGA TGG AAT GAT TTG GAT GTC     990
Asp Tyr Ile Gln Gly Gly Leu Thr Pro Arg Trp Asn Asp Leu Asp Val
            270                 275                 280

AAT CAG CAT GTG AAC AAC CTC AAA TAC GTT GCC TGG GTT TTT GAG ACC    1038
Asn Gln His Val Asn Asn Leu Lys Tyr Val Ala Trp Val Phe Glu Thr
        285                 290                 295

GTC CCA GAC TCC ATC TTT GAG AGT CAT CAT ATT TCC AGC TTC ACT CTT    1086
Val Pro Asp Ser Ile Phe Glu Ser His His Ile Ser Ser Phe Thr Leu
    300                 305                 310

GAA TAC AGG AGA GAG TGC ACG AGG GAT AGC GTG CTG CGG TCC CTG ACC    1134
Glu Tyr Arg Arg Glu Cys Thr Arg Asp Ser Val Leu Arg Ser Leu Thr
315                 320                 325                 330

ACT GTC TCT GGT GGC TCG TCG GAG GCT GGG TTA GTG TGC GAT CAC TTG    1182
Thr Val Ser Gly Gly Ser Ser Glu Ala Gly Leu Val Cys Asp His Leu
                335                 340                 345

CTC CAG CTT GAA GGT GGG TCT GAG GTA TTG AGG GCA AGA ACA GAG TGG    1230
Leu Gln Leu Glu Gly Gly Ser Glu Val Leu Arg Ala Arg Thr Glu Trp
            350                 355                 360

AGG CCT AAG CTT ACC GAT AGT TTC AGA GGG ATT AGT GTG ATA CCC GCA    1278
Arg Pro Lys Leu Thr Asp Ser Phe Arg Gly Ile Ser Val Ile Pro Ala
        365                 370                 375

GAA CCG AGG GTG TAACTAATGA AAGAAGCATC TGTTGAAGTT TCTCCCATGC        1330
Glu Pro Arg Val
        380
```

5,723,761

-continued

| | | | | |
|---|---|---|---|---|
| TGTTCGTGAG | GATACTTTTT | AGAAGCTGCA | GTTTGCATTG | CTTGTGCAGA ATCATGGTCT 1390 |
| GTGGTTTTAG | ATGTATATAA | AAAATAGTCC | TGTAGTCATG | AAACTTAATA TCAGAAAAAT 1450 |
| AACTCAATGG | GTCAAGGTTA | TCGAAGTAGT | CATTTAAGCT | TTGAAATATG TTTTGTATTC 1510 |
| CTCGGCTTAA | TCTGTAAGCT | CTTTCTCTTG | CAATAAAGTT | CGCCTTTCAA T 1561 |

( 2 ) INFORMATION FOR SEQ ID NO: 6:

( i ) SEQUENCE CHARACTERISTICS:
( A ) LENGTH: 1474 base pairs
( B ) TYPE: nucleic acid
( C ) STRANDEDNESS: double
( D ) TOPOLOGY: linear ( i i ) MOLECULE TYPE: cDNA to mRNA ( x i ) SEQUENCE DESCRIPTION: SEQ ID NO: 6:

```
CTGGATACCA TTTTCCCTGC GAAAAAAC ATG GTG GCT GCT GCA GCA AGT TCC        52
                                Met Val Ala Ala Ala Ala Ser Ser
                                  1               5

GCA TTC TTC CCT GTT CCA GCC CCG GGA GCC TCC CCT AAA CCC GGG AAG       100
Ala Phe Phe Pro Val Pro Ala Pro Gly Ala Ser Pro Lys Pro Gly Lys
     10              15                  20

TTC GGA AAT TGG CCC TCG AGC TTG AGC CCT TCC TTC AAG CCC AAG TCA       148
Phe Gly Asn Trp Pro Ser Ser Leu Ser Pro Ser Phe Lys Pro Lys Ser
 25              30                  35                  40

ATC CCC AAT GGC GGA TTT CAG GTT AAG GCA AAT GAC AGC GCC CAT CCA       196
Ile Pro Asn Gly Gly Phe Gln Val Lys Ala Asn Asp Ser Ala His Pro
                 45                  50                  55

AAG GCT AAC GGT TCT GCA GTT AGT CTA AAG TCT GGC AGC CTC AAC ACT       244
Lys Ala Asn Gly Ser Ala Val Ser Leu Lys Ser Gly Ser Leu Asn Thr
             60                  65                  70

CAG GAG GAC ACT TCG TCG TCC CCT CCT CCT CGG ACT TTC CTT CAC CAG       292
Gln Glu Asp Thr Ser Ser Ser Pro Pro Pro Arg Thr Phe Leu His Gln
         75                  80                  85

TTG CCT GAT TGG AGT AGG CTT CTG ACT GCA ATC ACG ACC GTG TTC GTG       340
Leu Pro Asp Trp Ser Arg Leu Leu Thr Ala Ile Thr Thr Val Phe Val
     90                  95                 100

AAA TCT AAG AGG CCT GAC ATG CAT GAT CGG AAA TCC AAG AGG CCT GAC       388
Lys Ser Lys Arg Pro Asp Met His Asp Arg Lys Ser Lys Arg Pro Asp
105                 110                 115                 120

ATG CTG GTG GAC TCG TTT GGG TTG GAG AGT ACT GTT CAG GAT GGG CTC       436
Met Leu Val Asp Ser Phe Gly Leu Glu Ser Thr Val Gln Asp Gly Leu
                125                 130                 135

GTG TTC CGA CAG AGT TTT TCG ATT AGG TCT TAT GAA ATA GGC ACT GAT       484
Val Phe Arg Gln Ser Phe Ser Ile Arg Ser Tyr Glu Ile Gly Thr Asp
            140                 145                 150

CGA ACG GCC TCT ATA GAG ACA CTT ATG AAC CAC TTG CAG GAA ACA TCT       532
Arg Thr Ala Ser Ile Glu Thr Leu Met Asn His Leu Gln Glu Thr Ser
        155                 160                 165

CTC AAT CAT TGT AAG AGT ACC GGT ATT CTC CTT GAC GGC TTC GGT CGT       580
Leu Asn His Cys Lys Ser Thr Gly Ile Leu Leu Asp Gly Phe Gly Arg
    170                 175                 180

ACT CTT GAG ATG TGT AAA AGG GAC CTC ATT TGG GTG GTA ATA AAA ATG       628
Thr Leu Glu Met Cys Lys Arg Asp Leu Ile Trp Val Val Ile Lys Met
185                 190                 195                 200

CAG ATC AAG GTG AAT CGC TAT CCA GCT TGG GGC GAT ACT GTC GAG ATC       676
Gln Ile Lys Val Asn Arg Tyr Pro Ala Trp Gly Asp Thr Val Glu Ile
                205                 210                 215

AAT ACC CGG TTC TCC CGG TTG GGG AAA ATC GGT ATG GGT CGC GAT TGG       724
Asn Thr Arg Phe Ser Arg Leu Gly Lys Ile Gly Met Gly Arg Asp Trp
```

|   |   |   |   |   |   |   |   |   |   |   |   |   |   |   |   |     |
|---|---|---|---|---|---|---|---|---|---|---|---|---|---|---|---|----:|
|   |   |   | 220 |   |   |   |   | 225 |   |   |   |   | 230 |   |   |     |
| CTA | ATA | AGT | GAT | TGC | AAC | ACA | GGA | GAA | ATT | CTT | GTA | AGA | GCT | ACG | AGC | 772 |
| Leu | Ile | Ser | Asp | Cys | Asn | Thr | Gly | Glu | Ile | Leu | Val | Arg | Ala | Thr | Ser |     |
|     |     | 235 |     |     |     |     | 240 |     |     |     |     | 245 |     |     |     |     |
| GCG | TAT | GCC | ATG | ATG | AAT | CAA | AAG | ACG | AGA | AGA | CTC | TCA | AAA | CTT | CCA | 820 |
| Ala | Tyr | Ala | Met | Met | Asn | Gln | Lys | Thr | Arg | Arg | Leu | Ser | Lys | Leu | Pro |     |
|     |     | 250 |     |     |     |     | 255 |     |     |     |     | 260 |     |     |     |     |
| TAC | GAG | GTT | CAC | CAG | GAG | ATA | GTG | CCT | CTT | TTT | GTC | GAC | TCT | CCT | GTC | 868 |
| Tyr | Glu | Val | His | Gln | Glu | Ile | Val | Pro | Leu | Phe | Val | Asp | Ser | Pro | Val |     |
| 265 |     |     |     |     | 270 |     |     |     |     | 275 |     |     |     |     | 280 |     |
| ATT | GAA | GAC | AGT | GAT | CTG | AAA | GTG | CAT | AAG | TTT | AAA | GTG | AAG | ACT | GGT | 916 |
| Ile | Glu | Asp | Ser | Asp | Leu | Lys | Val | His | Lys | Phe | Lys | Val | Lys | Thr | Gly |     |
|     |     |     |     | 285 |     |     |     |     | 290 |     |     |     |     | 295 |     |     |
| GAT | TCC | ATT | CAA | AAG | GGT | CTA | ACT | CCG | GGG | TGG | AAT | GAC | TTG | GAT | GTC | 964 |
| Asp | Ser | Ile | Gln | Lys | Gly | Leu | Thr | Pro | Gly | Trp | Asn | Asp | Leu | Asp | Val |     |
|     |     |     | 300 |     |     |     |     | 305 |     |     |     |     | 310 |     |     |     |
| AAT | CAG | CAC | GTA | AGC | AAC | GTG | AAG | TAC | ATT | GGG | TGG | ATT | CTC | GAG | AGT | 1012 |
| Asn | Gln | His | Val | Ser | Asn | Val | Lys | Tyr | Ile | Gly | Trp | Ile | Leu | Glu | Ser |     |
|     |     | 315 |     |     |     |     | 320 |     |     |     |     | 325 |     |     |     |     |
| ATG | CCA | ACA | GAA | GTT | TTG | GAG | ACC | CAG | GAG | CTA | TGC | TCT | CTC | GCC | CTT | 1060 |
| Met | Pro | Thr | Glu | Val | Leu | Glu | Thr | Gln | Glu | Leu | Cys | Ser | Leu | Ala | Leu |     |
|     |     | 330 |     |     |     |     | 335 |     |     |     |     | 340 |     |     |     |     |
| GAA | TAT | AGG | CGG | GAA | TGC | GGA | AGG | GAC | AGT | GTG | CTG | GAG | TCC | GTG | ACC | 1108 |
| Glu | Tyr | Arg | Arg | Glu | Cys | Gly | Arg | Asp | Ser | Val | Leu | Glu | Ser | Val | Thr |     |
| 345 |     |     |     |     | 350 |     |     |     |     | 355 |     |     |     |     | 360 |     |
| GCT | ATG | GAT | CCC | TCA | AAA | GTT | GGA | GTC | CGT | TCT | CAG | TAC | CAG | CAC | CTT | 1156 |
| Ala | Met | Asp | Pro | Ser | Lys | Val | Gly | Val | Arg | Ser | Gln | Tyr | Gln | His | Leu |     |
|     |     |     |     | 365 |     |     |     |     | 370 |     |     |     |     | 375 |     |     |
| CTG | CGG | CTT | GAG | GAT | GGG | ACT | GCT | ATC | GTG | AAC | GGT | GCA | ACT | GAG | TGG | 1204 |
| Leu | Arg | Leu | Glu | Asp | Gly | Thr | Ala | Ile | Val | Asn | Gly | Ala | Thr | Glu | Trp |     |
|     |     |     | 380 |     |     |     |     | 385 |     |     |     |     | 390 |     |     |     |
| CGG | CCG | AAG | AAT | GCA | GGA | GCT | AAC | GGG | GCG | ATA | TCA | ACG | GGA | AAG | ACT | 1252 |
| Arg | Pro | Lys | Asn | Ala | Gly | Ala | Asn | Gly | Ala | Ile | Ser | Thr | Gly | Lys | Thr |     |
|     |     | 395 |     |     |     |     | 400 |     |     |     |     | 405 |     |     |     |     |
| TCA | AAT | GGA | AAC | TCG | GTC | TCT | TAGAAGTGTC | TCGGACCCT | TCCGAGATGT |   |   |   |   |   |   | 1303 |
| Ser | Asn | Gly | Asn | Ser | Val | Ser |   |   |   |   |   |   |   |   |   |     |
|     | 410 |     |     |     | 415 |     |   |   |   |   |   |   |   |   |   |     |

GCATTTCTTT TCTCCTTTTC ATTTTGTGGT GAGCTGAAAG AAGAGCATGT CGTTGCAATC 1363

AGTAAATTGT GTAGTTCGTT TTTCGCTTTG CTTCGCTCCT TTGTATAATA ATATGGTCAG 1423

TCGTCTTTGT ATCATTTCAT GTTTTCAGTT TATTTACGCC ATATAATTTT T 1474

( 2 ) INFORMATION FOR SEQ ID NO: 7:

( i ) SEQUENCE CHARACTERISTICS:
        ( A ) LENGTH: 1744 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO: 7:

CTTTGATCGG TCGATCCTTT CCTCTCGCTC ATAATTTACC CATTAGTCCC CTTTGCCTTC 60

TTTAAACCCT CCTTTCCTTT CTCTTCCCTT CTTCCTCTCT GGGAAGTTTA AAGCTTTTGC 120

CTTTCTCCCC CCCACAACCT CTTTCCCGCA TTTGTTGAGC TGTTTTTTTG TCGCCATTCG 180

TCCTCTCCTC TTCAGTTCAA CAGAA ATG GTG GCT ACC GCT GCA AGT TCT GCA 232
                                Met Val Ala Thr Ala Ala Ser Ser Ala
                                 1             5

TTC TTC CCC CTC CCA TCC GCC GAC ACC TCA TCG AGA CCC GGA AAG CTC 280

|     |     |     |     |     |     |     |     |     |     |     |     |     |     |     |     |
| --- | --- | --- | --- | --- | --- | --- | --- | --- | --- | --- | --- | --- | --- | --- | --- |
| Phe | Phe | Pro | Leu | Pro | Ser | Ala | Asp | Thr | Ser | Ser | Arg | Pro | Gly | Lys | Leu |
| 10  |     |     |     |     | 15  |     |     |     |     | 20  |     |     |     |     | 25  |

| GGC | AAT | AAG | CCA | TCG | AGC | TTG | AGC | CCC | CTC | AAG | CCC | AAA | TCG | ACC | CCC | 328 |
| --- | --- | --- | --- | --- | --- | --- | --- | --- | --- | --- | --- | --- | --- | --- | --- | --- |
| Gly | Asn | Lys | Pro | Ser | Ser | Leu | Ser | Pro | Leu | Lys | Pro | Lys | Ser | Thr | Pro |  |
|     |     |     |     | 30  |     |     |     |     | 35  |     |     |     |     | 40  |     |  |

| AAT | GGC | GGT | TTG | CAG | GTT | AAG | GCA | AAT | GCC | AGT | GCC | CCT | CCT | AAG | ATC | 376 |
| --- | --- | --- | --- | --- | --- | --- | --- | --- | --- | --- | --- | --- | --- | --- | --- | --- |
| Asn | Gly | Gly | Leu | Gln | Val | Lys | Ala | Asn | Ala | Ser | Ala | Pro | Pro | Lys | Ile |  |
|     |     |     |     | 45  |     |     |     |     | 50  |     |     |     |     | 55  |     |  |

| AAT | GGT | TCC | CCG | GTC | GGT | CTA | AAG | TCG | GGC | GGT | CTC | AAG | ACT | CAG | GAA | 424 |
| --- | --- | --- | --- | --- | --- | --- | --- | --- | --- | --- | --- | --- | --- | --- | --- | --- |
| Asn | Gly | Ser | Pro | Val | Gly | Leu | Lys | Ser | Gly | Gly | Leu | Lys | Thr | Gln | Glu |  |
|     |     | 60  |     |     |     |     | 65  |     |     |     |     | 70  |     |     |     |  |

| GAC | GCT | CAT | TCG | GCC | CCT | CCT | CCG | CGA | ACT | TTT | ATC | AAC | CAG | TTG | CCT | 472 |
| --- | --- | --- | --- | --- | --- | --- | --- | --- | --- | --- | --- | --- | --- | --- | --- | --- |
| Asp | Ala | His | Ser | Ala | Pro | Pro | Pro | Arg | Thr | Phe | Ile | Asn | Gln | Leu | Pro |  |
|     |     | 75  |     |     |     |     | 80  |     |     |     |     | 85  |     |     |     |  |

| GAT | TGG | AGT | ATG | CTT | CTT | GCT | GCA | ATC | ACG | ACT | GTC | TTC | TTG | GCT | GCA | 520 |
| --- | --- | --- | --- | --- | --- | --- | --- | --- | --- | --- | --- | --- | --- | --- | --- | --- |
| Asp | Trp | Ser | Met | Leu | Leu | Ala | Ala | Ile | Thr | Thr | Val | Phe | Leu | Ala | Ala |  |
| 90  |     |     |     |     | 95  |     |     |     |     | 100 |     |     |     |     | 105 |  |

| GAG | AAG | CAA | TGG | ATG | ATG | CTT | GAT | TGG | AAA | CCT | AAG | AGG | CCT | GAC | ATG | 568 |
| --- | --- | --- | --- | --- | --- | --- | --- | --- | --- | --- | --- | --- | --- | --- | --- | --- |
| Glu | Lys | Gln | Trp | Met | Met | Leu | Asp | Trp | Lys | Pro | Lys | Arg | Pro | Asp | Met |  |
|     |     |     |     | 110 |     |     |     |     | 115 |     |     |     |     | 120 |     |  |

| CTT | GTG | GAC | CCG | TTT | GGA | TTG | GGA | AGT | ATT | GTT | CAG | GAT | GGG | CTT | GTG | 616 |
| --- | --- | --- | --- | --- | --- | --- | --- | --- | --- | --- | --- | --- | --- | --- | --- | --- |
| Leu | Val | Asp | Pro | Phe | Gly | Leu | Gly | Ser | Ile | Val | Gln | Asp | Gly | Leu | Val |  |
|     |     |     | 125 |     |     |     |     | 130 |     |     |     |     | 135 |     |     |  |

| TTC | AGG | CAG | AAT | TTT | TCG | ATT | AGG | TCC | TAT | GAA | ATA | GGC | GCC | GAT | CGC | 664 |
| --- | --- | --- | --- | --- | --- | --- | --- | --- | --- | --- | --- | --- | --- | --- | --- | --- |
| Phe | Arg | Gln | Asn | Phe | Ser | Ile | Arg | Ser | Tyr | Glu | Ile | Gly | Ala | Asp | Arg |  |
|     |     | 140 |     |     |     |     | 145 |     |     |     |     | 150 |     |     |     |  |

| ACT | GCG | TCT | ATA | GAG | ACG | GTG | ATG | AAC | CAT | TTG | CAG | GAA | ACA | GCT | CTC | 712 |
| --- | --- | --- | --- | --- | --- | --- | --- | --- | --- | --- | --- | --- | --- | --- | --- | --- |
| Thr | Ala | Ser | Ile | Glu | Thr | Val | Met | Asn | His | Leu | Gln | Glu | Thr | Ala | Leu |  |
|     | 155 |     |     |     |     | 160 |     |     |     |     | 165 |     |     |     |     |  |

| AAT | CAT | GTT | AAG | ATT | GCT | GGG | CTT | TCT | AAT | GAC | GGC | TTT | GGT | CGT | ACT | 760 |
| --- | --- | --- | --- | --- | --- | --- | --- | --- | --- | --- | --- | --- | --- | --- | --- | --- |
| Asn | His | Val | Lys | Ile | Ala | Gly | Leu | Ser | Asn | Asp | Gly | Phe | Gly | Arg | Thr |  |
| 170 |     |     |     |     | 175 |     |     |     |     | 180 |     |     |     |     | 185 |  |

| CCT | GAG | ATG | TAT | AAA | AGG | GAC | CTT | ATT | TGG | GTT | GTT | GCG | AAA | ATG | CAA | 808 |
| --- | --- | --- | --- | --- | --- | --- | --- | --- | --- | --- | --- | --- | --- | --- | --- | --- |
| Pro | Glu | Met | Tyr | Lys | Arg | Asp | Leu | Ile | Trp | Val | Val | Ala | Lys | Met | Gln |  |
|     |     |     |     | 190 |     |     |     |     | 195 |     |     |     |     | 200 |     |  |

| GTC | ATG | GTT | AAC | CGC | TAT | CCT | ACT | TGG | GGT | GAC | ACG | GTT | GAA | GTG | AAT | 856 |
| --- | --- | --- | --- | --- | --- | --- | --- | --- | --- | --- | --- | --- | --- | --- | --- | --- |
| Val | Met | Val | Asn | Arg | Tyr | Pro | Thr | Trp | Gly | Asp | Thr | Val | Glu | Val | Asn |  |
|     |     |     | 205 |     |     |     |     | 210 |     |     |     |     | 215 |     |     |  |

| ACT | TGG | GTT | GCC | AAG | TCA | GGG | AAA | AAT | GGT | ATG | CGT | CGT | GAC | TGG | CTC | 904 |
| --- | --- | --- | --- | --- | --- | --- | --- | --- | --- | --- | --- | --- | --- | --- | --- | --- |
| Thr | Trp | Val | Ala | Lys | Ser | Gly | Lys | Asn | Gly | Met | Arg | Arg | Asp | Trp | Leu |  |
|     |     | 220 |     |     |     |     | 225 |     |     |     |     | 230 |     |     |     |  |

| ATA | AGT | GAT | TGC | AAT | ACT | GGA | GAG | ATT | CTT | ACA | AGA | GCA | TCA | AGC | GTG | 952 |
| --- | --- | --- | --- | --- | --- | --- | --- | --- | --- | --- | --- | --- | --- | --- | --- | --- |
| Ile | Ser | Asp | Cys | Asn | Thr | Gly | Glu | Ile | Leu | Thr | Arg | Ala | Ser | Ser | Val |  |
|     | 235 |     |     |     |     | 240 |     |     |     |     | 245 |     |     |     |     |  |

| TGG | GTC | ATG | ATG | AAT | CAA | AAG | ACA | AGA | AGA | TTG | TCA | AAA | ATT | CCA | GAT | 1000 |
| --- | --- | --- | --- | --- | --- | --- | --- | --- | --- | --- | --- | --- | --- | --- | --- | --- |
| Trp | Val | Met | Met | Asn | Gln | Lys | Thr | Arg | Arg | Leu | Ser | Lys | Ile | Pro | Asp |  |
| 250 |     |     |     |     | 255 |     |     |     |     | 260 |     |     |     |     | 265 |  |

| GAG | GTT | CGA | AAT | GAG | ATA | GAG | CCT | CAT | TTT | GTG | GAC | TCT | CCT | CCC | GTC | 1048 |
| --- | --- | --- | --- | --- | --- | --- | --- | --- | --- | --- | --- | --- | --- | --- | --- | --- |
| Glu | Val | Arg | Asn | Glu | Ile | Glu | Pro | His | Phe | Val | Asp | Ser | Pro | Pro | Val |  |
|     |     |     |     | 270 |     |     |     |     | 275 |     |     |     |     | 280 |     |  |

| ATT | GAA | GAC | GAT | GAC | CGG | AAA | CTT | CCC | AAG | CTG | GAT | GAG | AAG | ACT | GCT | 1096 |
| --- | --- | --- | --- | --- | --- | --- | --- | --- | --- | --- | --- | --- | --- | --- | --- | --- |
| Ile | Glu | Asp | Asp | Asp | Arg | Lys | Leu | Pro | Lys | Leu | Asp | Glu | Lys | Thr | Ala |  |
|     |     |     | 285 |     |     |     |     | 290 |     |     |     |     | 295 |     |     |  |

| GAC | TCC | ATC | CGC | AAG | GGT | CTA | ACT | CCG | AGG | TGG | AAT | GAC | TTG | GAT | GTC | 1144 |
| --- | --- | --- | --- | --- | --- | --- | --- | --- | --- | --- | --- | --- | --- | --- | --- | --- |
| Asp | Ser | Ile | Arg | Lys | Gly | Leu | Thr | Pro | Arg | Trp | Asn | Asp | Leu | Asp | Val |  |
|     |     | 300 |     |     |     |     | 305 |     |     |     |     | 310 |     |     |     |  |

| AAT | CAA | CAC | GTC | AAC | AAC | GTG | AAG | TAC | ATC | GGG | TGG | ATT | CTT | GAG | AGT | 1192 |
| --- | --- | --- | --- | --- | --- | --- | --- | --- | --- | --- | --- | --- | --- | --- | --- | --- |
| Asn | Gln | His | Val | Asn | Asn | Val | Lys | Tyr | Ile | Gly | Trp | Ile | Leu | Glu | Ser |  |
|     | 315 |     |     |     |     | 320 |     |     |     |     | 325 |     |     |     |     |  |

| ACT | CCA | CCA | GAA | GTT | CTG | GAG | ACC | CAG | GAG | TTA | TGT | TCC | CTT | ACT | CTG | 1240 |
| --- | --- | --- | --- | --- | --- | --- | --- | --- | --- | --- | --- | --- | --- | --- | --- | --- |

```
Thr  Pro  Pro  Glu  Val  Leu  Glu  Thr  Gln  Glu  Leu  Cys  Ser  Leu  Thr  Leu
330            335                 340                 345

GAA  TAC  AGG  CGG  GAA  TGT  GGA  AGG  GAG  AGC  GTG  CTG  GAG  TCC  CTC  ACT    1288
Glu  Tyr  Arg  Arg  Glu  Cys  Gly  Arg  Glu  Ser  Val  Leu  Glu  Ser  Leu  Thr
               350                 355                 360

GCT  ATG  GAT  CCC  TCT  GGA  GGG  GGT  TAT  GGG  TCC  CAG  TTT  CAG  CAC  CTT    1336
Ala  Met  Asp  Pro  Ser  Gly  Gly  Gly  Tyr  Gly  Ser  Gln  Phe  Gln  His  Leu
               365                 370                 375

CTG  CGG  CTT  GAG  GAT  GGA  GGT  GAG  ATC  GTG  AAG  GGG  AGA  ACT  GAG  TGG    1384
Leu  Arg  Leu  Glu  Asp  Gly  Gly  Glu  Ile  Val  Lys  Gly  Arg  Thr  Glu  Trp
               380                 385                 390

CGG  CCC  AAG  AAT  GGT  GTA  ATC  AAT  GGG  GTG  GTA  CCA  ACC  GGG  GAG  TCC    1432
Arg  Pro  Lys  Asn  Gly  Val  Ile  Asn  Gly  Val  Val  Pro  Thr  Gly  Glu  Ser
               395                 400                 405

TCA  CCT  GGA  GAC  TAC  TCT  TAGAAGGGAG  CCCTGACCCC  TTTGGAGTTG                  1480
Ser  Pro  Gly  Asp  Tyr  Ser
410                 415

TGATTTCTTT ATTGTCGGAC GAGCTAAGTG AAGGGCAGGT AAGATAGTAG CAATCGGTAG                1540

ATTGTGTAGT TTGTTTGCTG CTTTTTCACG ATGGCTCTCG TGTATAATAT CATGGTCTGT                1600

CTTCTTTGTA TCCTCTTCTT CGCATGTTCC GGGTTGATTC ATACATTATA TTCTTTCTAT                1660

TTGTTTGAAG GCGAGTAGCG GGTTGTAATT ATTTATTTTG TCATTACAAT GTCGTTTAAC                1720

TTTTCAAATG AAACTACTTA TGTG                                                       1744
```

( 2 ) INFORMATION FOR SEQ ID NO: 8:

( i ) SEQUENCE CHARACTERISTICS:
        ( A ) LENGTH: 1433 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO: 8:

```
GAA  TTC  GGC  ACG  AGG  GGC  TCC  GGT  GCT  TTG  CAG  GTG  AAG  GCA  AGT  TCC     48
Glu  Phe  Gly  Thr  Arg  Gly  Ser  Gly  Ala  Leu  Gln  Val  Lys  Ala  Ser  Ser
               5                   10                  15

CAA  GCT  CCA  CCA  AAG  CTC  AAT  GGT  TCC  AAT  GTG  GGT  TTG  GTT  AAA  TCT     96
Gln  Ala  Pro  Pro  Lys  Leu  Asn  Gly  Ser  Asn  Val  Gly  Leu  Val  Lys  Ser
               20                  25                  30

AGC  CAA  ATT  GTG  AAG  AAG  GGT  GAT  GAC  ACC  ACA  TCT  CCT  CCT  GCA  AGA    144
Ser  Gln  Ile  Val  Lys  Lys  Gly  Asp  Asp  Thr  Thr  Ser  Pro  Pro  Ala  Arg
               35                  40                  45

ACT  TTC  ATC  AAC  CAA  TTG  CCT  GAT  TGG  AGC  ATG  CTT  CTT  GCT  GCT  ATC    192
Thr  Phe  Ile  Asn  Gln  Leu  Pro  Asp  Trp  Ser  Met  Leu  Leu  Ala  Ala  Ile
     50                  55                  60

ACA  ACC  CTG  TTC  TTG  GCT  GCA  GAG  AAG  CAG  TGG  ATG  ATG  CTT  GAT  TGG    240
Thr  Thr  Leu  Phe  Leu  Ala  Ala  Glu  Lys  Gln  Trp  Met  Met  Leu  Asp  Trp
65                  70                  75                  80

AAA  CCC  AAA  AGG  CCT  GAC  ATG  CTT  GTT  GAT  CCA  TTT  GGT  CTT  GGA  AGG    288
Lys  Pro  Lys  Arg  Pro  Asp  Met  Leu  Val  Asp  Pro  Phe  Gly  Leu  Gly  Arg
               85                  90                  95

TTT  GTT  CAG  GAT  GGT  CTT  GTT  TTC  CGC  AAC  AAC  TTT  TCA  ATT  CGA  TCA    336
Phe  Val  Gln  Asp  Gly  Leu  Val  Phe  Arg  Asn  Asn  Phe  Ser  Ile  Arg  Ser
               100                 105                 110

TAT  GAA  ATA  GGG  GCT  GAT  CGA  ACG  GCT  TCT  ATA  GAA  ACG  TTA  ATG  AAT    384
Tyr  Glu  Ile  Gly  Ala  Asp  Arg  Thr  Ala  Ser  Ile  Glu  Thr  Leu  Met  Asn
               115                 120                 125

CAT  CTG  CAG  GAA  ACA  GCT  CTT  AAT  CAT  GTG  AAG  TCT  GTT  GGG  CTT  CTT    432
His  Leu  Gln  Glu  Thr  Ala  Leu  Asn  His  Val  Lys  Ser  Val  Gly  Leu  Leu
```

```
                         130                        135                         140
GAG  GAT  GGC  CTA  GGT  TCG  ACT  CGA  GAG  ATG  TCC  TTG  AGG  AAC  CTG  ATA        480
Glu  Asp  Gly  Leu  Gly  Ser  Thr  Arg  Glu  Met  Ser  Leu  Arg  Asn  Leu  Ile
145                      150                       155                       160

TGG  GTT  GTC  ACT  AAA  ATG  CAG  GTT  GCG  GTT  GAT  CGC  TAT  CCA  ACT  TGG        528
Trp  Val  Val  Thr  Lys  Met  Gln  Val  Ala  Val  Asp  Arg  Tyr  Pro  Thr  Trp
                    165                      170                      175

GGA  GAT  GAA  GTT  CAG  GTA  TCC  TCT  TGG  GCT  ACT  GCA  ATT  GGA  AAG  AAT        576
Gly  Asp  Glu  Val  Gln  Val  Ser  Ser  Trp  Ala  Thr  Ala  Ile  Gly  Lys  Asn
               180                      185                      190

GGA  ATG  CGT  CGC  GAA  TGG  ATA  GTC  ACT  GAT  TTT  AGA  ACT  GGT  GAA  ACT        624
Gly  Met  Arg  Arg  Glu  Trp  Ile  Val  Thr  Asp  Phe  Arg  Thr  Gly  Glu  Thr
          195                      200                      205

CTA  TTA  AGA  GCC  ACC  AGT  GTT  TGG  GTG  ATG  ATG  AAT  AAA  CTG  ACG  AGG        672
Leu  Leu  Arg  Ala  Thr  Ser  Val  Trp  Val  Met  Met  Asn  Lys  Leu  Thr  Arg
     210                      215                      220

AGG  ATA  TCC  AAA  ATC  CCA  GAA  GAG  GTT  TGG  CAC  GAA  ATA  GGC  CCC  TCT        720
Arg  Ile  Ser  Lys  Ile  Pro  Glu  Glu  Val  Trp  His  Glu  Ile  Gly  Pro  Ser
225                      230                      235                      240

TTC  ATT  GAT  GCT  CCT  CCT  CTT  CCC  ACC  GTG  GAA  GAT  GAT  GGT  AGA  AAG        768
Phe  Ile  Asp  Ala  Pro  Pro  Leu  Pro  Thr  Val  Glu  Asp  Asp  Gly  Arg  Lys
                    245                      250                      255

CTG  ACA  AGG  TTT  GAT  GAA  AGT  TCT  GCA  GAC  TTT  ATC  CGC  NCT  GGT  TTA        816
Leu  Thr  Arg  Phe  Asp  Glu  Ser  Ser  Ala  Asp  Phe  Ile  Arg  Xxx  Gly  Leu
               260                      265                      270

ACT  CCT  AGG  TGG  AGT  GAT  TTG  GAC  ATC  AAC  CAG  CAT  GTC  AAC  AAT  GTG        864
Thr  Pro  Arg  Trp  Ser  Asp  Leu  Asp  Ile  Asn  Gln  His  Val  Asn  Asn  Val
          275                      280                      285

AAG  TAC  ATT  GGC  TGG  CTC  CTT  GAG  AGT  GCT  CCG  CCG  GAG  ATC  CAC  GAG        912
Lys  Tyr  Ile  Gly  Trp  Leu  Leu  Glu  Ser  Ala  Pro  Pro  Glu  Ile  His  Glu
     290                      295                      300

AGT  CAC  GAG  ATA  GCG  TCT  CTG  ACT  CTG  GAG  TAC  AGG  AGG  GAG  TGT  GGA        960
Ser  His  Glu  Ile  Ala  Ser  Leu  Thr  Leu  Glu  Tyr  Arg  Arg  Glu  Cys  Gly
305                      310                      315                      320

AGG  GAC  AGC  GTG  CTG  AAC  TCC  GCG  ACC  AAG  GTC  TCT  GAC  TCC  TCT  CAA       1008
Arg  Asp  Ser  Val  Leu  Asn  Ser  Ala  Thr  Lys  Val  Ser  Asp  Ser  Ser  Gln
                    325                      330                      335

CTG  GGA  AAG  TCT  GCT  GTG  GAG  TGT  AAC  CAC  TTG  GTT  CGT  CTC  CAG  AAT       1056
Leu  Gly  Lys  Ser  Ala  Val  Glu  Cys  Asn  His  Leu  Val  Arg  Leu  Gln  Asn
               340                      345                      350

GGT  GGG  GAG  ATT  GTG  AAG  GGA  AGG  ACT  GTG  TGG  AGG  CCC  AAA  CGT  CCT       1104
Gly  Gly  Glu  Ile  Val  Lys  Gly  Arg  Thr  Val  Trp  Arg  Pro  Lys  Arg  Pro
          355                      360                      365

CTT  TAC  AAT  GAT  GGT  GCT  GTT  GTG  GAC  GTG  NAA  GCT  AAA  ACC  TCT            1149
Leu  Tyr  Asn  Asp  Gly  Ala  Val  Val  Asp  Val  Xxx  Ala  Lys  Thr  Ser
     370                      375                      380

TAAGTCTTAT  AGTCCAAGTG  AGGAGGAGTT  CTATGTATCA  GGAAGTTGCT  AGGATTCTCA             1209

ATCGCATGTG  TCCATTTCTT  GTGTGGAATA  CTGCTCGTGT  TTCTAGACTC  GCTATATGTT             1269

TGTTCTTTTA  TATATATATA  TATATATATA  TCTCTCTCTT  CCCCCCACCT  CTCTCTCTCT             1329

CTCTATATAT  ATATATGTTT  TATGTAAGTT  TTCCCCTTAG  TTTCCTTTCC  TAAGTAATGC             1389

CATTGTAAAT  TACTTCAAAA  AAAAAAAAAA  AAAAAAAACT  CGAG                              1433
```

( 2 ) INFORMATION FOR SEQ ID NO: 9:

( i ) SEQUENCE CHARACTERISTICS:
        ( A ) LENGTH: 1461 base pairs
        ( B ) TYPE: nucleic acid
        ( C ) STRANDEDNESS: double
        ( D ) TOPOLOGY: linear ( i i ) MOLECULE TYPE: other nucleic acid
(A) DESCRIPTION:; PCR generated DNA from mRNA ( x i ) SEQUENCE DESCRIPTION: SEQ ID NO: 9:

```
TCAAC ATG GCC ACC ACC TCT TTA GCT TCT GCT TTC TGC TCG ATG AAA GCT      50
      Met Ala Thr Thr Ser Leu Ala Ser Ala Phe Cys Ser Met Lys Ala
       1           5                  10                 15

GTA ATG TTG GCT CGT GAT GGC AGG GGC ATG AAA CCC AGG AGC AGT GAT          98
Val Met Leu Ala Arg Asp Gly Arg Gly Met Lys Pro Arg Ser Ser Asp
             20                  25                  30

TTG CAG CTG AGG GCG GGA AAT GCA CAA ACC TCT TTG AAG ATG ATC AAT         146
Leu Gln Leu Arg Ala Gly Asn Ala Gln Thr Ser Leu Lys Met Ile Asn
 35                  40                  45

GGG ACC AAG TTC AGT TAC ACA GAG AGC TTG AAA AAG TTG CCT GAC TGG         194
Gly Thr Lys Phe Ser Tyr Thr Glu Ser Leu Lys Lys Leu Pro Asp Trp
 50                  55                  60

AGC ATG CTC TTT GCA GTG ATC ACG ACC ATC TTT TCG GCT GCT GAG AAG         242
Ser Met Leu Phe Ala Val Ile Thr Thr Ile Phe Ser Ala Ala Glu Lys
 65                  70                  75

CAG TGG ACC AAT CTA GAG TGG AAG CCG AAG CCG AAT CCA CCC CAG TTG         290
Gln Trp Thr Asn Leu Glu Trp Lys Pro Lys Pro Asn Pro Pro Gln Leu
     80                  85                  90              95

CTT GAT GAC CAT TTT GGG CCG CAT GGG TTA GTT TTC AGG CGC ACC TTT         338
Leu Asp Asp His Phe Gly Pro His Gly Leu Val Phe Arg Arg Thr Phe
                100                 105                 110

GCC ATC AGA TCG TAT GAG GTG GGA CCT GAC CGC TCC ACA TCT ATA GTG         386
Ala Ile Arg Ser Tyr Glu Val Gly Pro Asp Arg Ser Thr Ser Ile Val
             115                 120                 125

GCT GTT ATG AAT CAC TTG CAG GAG GCT GCA CTT AAT CAT GCG AAG AGT         434
Ala Val Met Asn His Leu Gln Glu Ala Ala Leu Asn His Ala Lys Ser
         130                 135                 140

GTG GGA ATT CTA GGA GAT GGA TTC GGT ACG ACG CTA GAG ATG AGT AAG         482
Val Gly Ile Leu Gly Asp Gly Phe Gly Thr Thr Leu Glu Met Ser Lys
     145                 150                 155

AGA GAT CTG ATA TGG GTT GTG AAA CGC ACG CAT GTT GCT GTG GAA CGG         530
Arg Asp Leu Ile Trp Val Val Lys Arg Thr His Val Ala Val Glu Arg
 160                 165                 170                 175

TAC CCT GCT TGG GGT GAT ACT GTT GAA GTA GAG TGC TGG GTT GGT GCA         578
Tyr Pro Ala Trp Gly Asp Thr Val Glu Val Glu Cys Trp Val Gly Ala
                 180                 185                 190

TCG GGA AAT AAT GGC AGG CGC CAT GAT TTC CTT GTC CGG GAC TGC AAA         626
Ser Gly Asn Asn Gly Arg Arg His Asp Phe Leu Val Arg Asp Cys Lys
             195                 200                 205

ACA GGC GAA ATT CTT ACA AGA TGT ACC AGT CTT TCG GTG ATG ATG AAT         674
Thr Gly Glu Ile Leu Thr Arg Cys Thr Ser Leu Ser Val Met Met Asn
         210                 215                 220

ACA AGG ACA AGG AGG TTG TCC AAA ATC CCT GAA GAA GTT AGA GGG GAG         722
Thr Arg Thr Arg Arg Leu Ser Lys Ile Pro Glu Glu Val Arg Gly Glu
     225                 230                 235

ATA GGG CCT GCA TTC ATT GAT AAT GTG GCT GTC AAG GAC GAG GAA ATT         770
Ile Gly Pro Ala Phe Ile Asp Asn Val Ala Val Lys Asp Glu Glu Ile
 240                 245                 250                 255

AAG AAA CCA CAG AAG CTC AAT GAC AGC ACT GCA GAT TAC ATC CAA GGA         818
Lys Lys Pro Gln Lys Leu Asn Asp Ser Thr Ala Asp Tyr Ile Gln Gly
                 260                 265                 270

GGA TTG ACT CCT CGA TGG AAT GAT TTG GAT ATC AAT CAG CAC GTT AAC         866
Gly Leu Thr Pro Arg Trp Asn Asp Leu Asp Ile Asn Gln His Val Asn
             275                 280                 285

AAC ATC AAA TAC GTT GAC TGG ATT CTT GAG ACT GTC CCA GAC TCA ATC         914
Asn Ile Lys Tyr Val Asp Trp Ile Leu Glu Thr Val Pro Asp Ser Ile
```

| | | | | | | | | | | | | | | | |
|---|---|---|---|---|---|---|---|---|---|---|---|---|---|---|---|
| | | | 290 | | | | | 295 | | | | | 300 | | |
| TTT | GAG | AGT | CAT | CAT | ATT | TCC | AGC | TTC | ACT | ATT | GAA | TAC | AGG | AGA | GAG | 962 |
| Phe | Glu | Ser | His | His | Ile | Ser | Ser | Phe | Thr | Ile | Glu | Tyr | Arg | Arg | Glu | |
| | 305 | | | | | 310 | | | | | 315 | | | | | |
| TGC | ACG | ATG | GAT | AGC | GTG | CTG | CAG | TCC | CTG | ACC | ACT | GTC | TCC | GGT | GGC | 1010 |
| Cys | Thr | Met | Asp | Ser | Val | Leu | Gln | Ser | Leu | Thr | Thr | Val | Ser | Gly | Gly | |
| 320 | | | | | 325 | | | | | 330 | | | | | 335 | |
| TCG | TCG | GAA | GCT | GGG | TTA | GTG | TGC | GAG | CAC | TTG | CTC | CAG | CTT | GAA | GGT | 1058 |
| Ser | Ser | Glu | Ala | Gly | Leu | Val | Cys | Glu | His | Leu | Leu | Gln | Leu | Glu | Gly | |
| | | | | 340 | | | | | 345 | | | | | 350 | | |
| GGG | TCT | GAG | GTA | TTG | AGG | GCA | AAA | ACA | GAG | TGG | AGG | CCT | AAG | CTT | ACC | 1106 |
| Gly | Ser | Glu | Val | Leu | Arg | Ala | Lys | Thr | Glu | Trp | Arg | Pro | Lys | Leu | Thr | |
| | | | | 355 | | | | | 360 | | | | | 365 | | |
| GAT | AGT | TTC | AGA | GGG | ATT | AGT | GTG | ATA | CCC | GCA | GAA | TCG | AGT | GTC | | 1151 |
| Asp | Ser | Phe | Arg | Gly | Ile | Ser | Val | Ile | Pro | Ala | Glu | Ser | Ser | Val | | |
| | | 370 | | | | | 375 | | | | | 380 | | | | |

TAACTAACGA AAGAAGCATC TGATGAAGTT TCTCCTGTGC TGTTGTTCGT GAGGATGCTT 1211

TTTAGAAGCT GCAGTTTGCA TTGCTTGTGC AGAATCATGG CCTGTGGTTT TAGATATATA 1271

TCCAAAATTG TCCTATAGTC AAGAAACTTA ATATCAGAAA AATAACTCAA TGAGTCAAGG 1331

TTATCGAAGT AGTCATGTAA GCTTGAAAT ATGTTGTGTA TTCCTCGGCT TTATGTAATC 1391

TGTAAGCTCT TTCTCTTGCA ATAAATTTCG CCTTTCAATA ATAAAAAAAA AAAAAAAGG 1451

TCGACTCGAG 1461

( 2 ) INFORMATION FOR SEQ ID NO: 10:

( i ) SEQUENCE CHARACTERISTICS:
        ( A ) LENGTH: 1435 base pairs
        ( B ) TYPE: nucleic acid
        ( C ) STRANDEDNESS: double
        ( D ) TOPOLOGY: linear ( i i ) MOLECULE TYPE: cDNA to mRNA ( x i ) SEQUENCE DESCRIPTION: SEQ ID NO: 10:

AAAAAAGTAC AAACTGTATG GTAGCCATTT ACATATAACT ACTCTATAAT TTTCAAC ATG 60
                                                                                                                                           Met
                                                                                                                                                             1

| | | | | | | | | | | | | | | | |
|---|---|---|---|---|---|---|---|---|---|---|---|---|---|---|---|
| GTC | ACC | ACC | TCT | TTA | GCT | TCC | GCT | TTC | TTC | TCG | ATG | AAA | GCT | GTA | ATG | 108 |
| Val | Thr | Thr | Ser | Leu | Ala | Ser | Ala | Phe | Phe | Ser | Met | Lys | Ala | Val | Met | |
| | | | 5 | | | | | 10 | | | | | 15 | | | |
| TTG | GCT | CCT | GAT | GGC | AGT | GGC | ATA | AAA | CCC | AGG | AGC | AGT | GGT | TTG | CAG | 156 |
| Leu | Ala | Pro | Asp | Gly | Ser | Gly | Ile | Lys | Pro | Arg | Ser | Ser | Gly | Leu | Gln | |
| | | 20 | | | | | 25 | | | | | 30 | | | | |
| GTG | AGG | GCG | GGA | AAG | GAA | CAA | AAC | TCT | TGC | AAG | ATG | ATC | AAT | GGG | ACC | 204 |
| Val | Arg | Ala | Gly | Lys | Glu | Gln | Asn | Ser | Cys | Lys | Met | Ile | Asn | Gly | Thr | |
| | 35 | | | | | 40 | | | | | 45 | | | | | |
| AAG | GTC | AAA | GAC | ACG | GAG | GGC | TTG | AAA | GGG | CGC | AGC | ACA | TTG | CAT | GGC | 252 |
| Lys | Val | Lys | Asp | Thr | Glu | Gly | Leu | Lys | Gly | Arg | Ser | Thr | Leu | His | Gly | |
| 50 | | | | | 55 | | | | | 60 | | | | | 65 | |
| TGG | AGC | ATG | CCC | CTT | GAA | TTG | ATC | ACA | ACC | ATC | TTT | TCG | GCT | GCT | GAG | 300 |
| Trp | Ser | Met | Pro | Leu | Glu | Leu | Ile | Thr | Thr | Ile | Phe | Ser | Ala | Ala | Glu | |
| | | | | 70 | | | | | 75 | | | | | 80 | | |
| AAG | CAG | TGG | ACC | AAT | CTA | GTT | AGT | AAG | CCA | CCG | CAG | TTG | CTT | GAT | GAC | 348 |
| Lys | Gln | Trp | Thr | Asn | Leu | Val | Ser | Lys | Pro | Pro | Gln | Leu | Leu | Asp | Asp | |
| | | | 85 | | | | | 90 | | | | | 95 | | | |
| CAT | TTA | GGT | CTG | CAT | GGG | CTA | GTT | TTC | AGG | CGC | ACC | TTT | GCA | ATC | AGA | 396 |
| His | Leu | Gly | Leu | His | Gly | Leu | Val | Phe | Arg | Arg | Thr | Phe | Ala | Ile | Arg | |
| | | | 100 | | | | | 105 | | | | | 110 | | | |
| TGC | AGT | GAG | GTT | GGA | CCT | GAC | CGC | TCC | ACA | TCC | ATA | GTG | GCT | GTT | ATG | 444 |

```
            Cys  Ser  Glu  Val  Gly  Pro  Asp  Arg  Ser  Thr  Ser  Ile  Val  Ala  Val  Met
                 115                 120                           125

AAT  TAC  TTG  CAG  GAA  GCT  GCA  TGT  AAT  CAT  GCG  GAG  AGT  CTG  GGA  CTT               492
Asn  Tyr  Leu  Gln  Glu  Ala  Ala  Cys  Asn  His  Ala  Glu  Ser  Leu  Gly  Leu
130                      135                      140                      145

CTA  GGA  GAT  GGA  TTC  GGT  GAG  ACA  CTA  GAG  ATG  AGT  AGG  AGA  GAT  CTG               540
Leu  Gly  Asp  Gly  Phe  Gly  Glu  Thr  Leu  Glu  Met  Ser  Arg  Arg  Asp  Leu
                         150                      155                      160

ATA  TGG  GTT  GTG  AGA  CGC  ACG  CAT  GTT  GTT  GTG  GGA  ACG  TAC  CCT  GCT               588
Ile  Trp  Val  Val  Arg  Arg  Thr  His  Val  Val  Val  Gly  Thr  Tyr  Pro  Ala
                    165                      170                      175

TGG  GGC  GAT  ACT  GTT  GAA  GTC  GAG  GCC  TGG  ATC  GGT  GCA  GCT  GGA  AAC               636
Trp  Gly  Asp  Thr  Val  Glu  Val  Glu  Ala  Trp  Ile  Gly  Ala  Ala  Gly  Asn
          180                      185                      190

ATT  GGC  ATG  CGC  CGC  CAT  TTT  CTT  GTC  CGC  GAC  TGC  AAA  ACT  GGC  CAC               684
Ile  Gly  Met  Arg  Arg  His  Phe  Leu  Val  Arg  Asp  Cys  Lys  Thr  Gly  His
     195                      200                      205

ATT  CTT  GCA  AGA  TGT  ACC  AGT  GTT  TCA  GTG  ATG  ATG  AAT  ATG  AGG  ACA               732
Ile  Leu  Ala  Arg  Cys  Thr  Ser  Val  Ser  Val  Met  Met  Asn  Met  Arg  Thr
210                      215                      220                      225

AGG  AGA  TTG  TCC  AAA  ATT  CCC  CAA  GAA  GTT  AGA  GGG  GAG  ATT  GAC  CCT               780
Arg  Arg  Leu  Ser  Lys  Ile  Pro  Gln  Glu  Val  Arg  Gly  Glu  Ile  Asp  Pro
                    230                      235                      240

CTT  TTC  ATC  GAA  AAG  TTT  GCT  GTC  AAG  GAA  GGG  GAA  ATT  AAG  AAA  TTA               828
Leu  Phe  Ile  Glu  Lys  Phe  Ala  Val  Lys  Glu  Gly  Glu  Ile  Lys  Lys  Leu
               245                      250                      255

CAG  AAG  TTC  AAT  GAT  AGC  ACT  GCA  GAT  TAC  ATT  CAA  GGG  GGT  TGG  ACT               876
Gln  Lys  Phe  Asn  Asp  Ser  Thr  Ala  Asp  Tyr  Ile  Gln  Gly  Gly  Trp  Thr
          260                      265                      270

CCG  CGA  TGG  AAT  GAT  TTG  GAT  GTC  AAT  CAG  CAC  GTG  AAC  AAT  ATC  AAA               924
Pro  Arg  Trp  Asn  Asp  Leu  Asp  Val  Asn  Gln  His  Val  Asn  Asn  Ile  Lys
     275                      280                      285

TAC  GTT  GGC  TGG  ATT  TTT  AAG  AGC  GTC  CCA  GAC  TCT  ATC  TAT  GAG  AAT               972
Tyr  Val  Gly  Trp  Ile  Phe  Lys  Ser  Val  Pro  Asp  Ser  Ile  Tyr  Glu  Asn
290                      295                      300                      305

CAT  CAT  CTT  TCT  AGC  ATC  ACT  CTC  GAA  TAC  AGG  AGA  GAG  TGC  ACA  AGG              1020
His  His  Leu  Ser  Ser  Ile  Thr  Leu  Glu  Tyr  Arg  Arg  Glu  Cys  Thr  Arg
                    310                      315                      320

GGC  AGA  GCA  CTG  CAG  TCC  CTG  ACC  ACT  GTT  TGT  GGT  GGC  TCG  TCC  GAA              1068
Gly  Arg  Ala  Leu  Gln  Ser  Leu  Thr  Thr  Val  Cys  Gly  Gly  Ser  Ser  Glu
               325                      330                      335

GCT  GGG  ATC  ATA  TGT  GAG  CAC  CTA  CTC  CAG  CTT  GAG  GAT  GGG  TCT  GAG              1116
Ala  Gly  Ile  Ile  Cys  Glu  His  Leu  Leu  Gln  Leu  Glu  Asp  Gly  Ser  Glu
          340                      345                      350

GTT  TTG  AGG  GGA  AGA  ACA  GAT  TGG  AGG  CCC  AAG  CGC  ACC  GAT  AGT  TTC              1164
Val  Leu  Arg  Gly  Arg  Thr  Asp  Trp  Arg  Pro  Lys  Arg  Thr  Asp  Ser  Phe
     355                      360                      365

GAA  GGC  ATT  AGT  GAG  AGA  TTC  CCG  CAG  CAA  GAA  CCG  CAT  AAT  TAAT                   1210
Glu  Gly  Ile  Ser  Glu  Arg  Phe  Pro  Gln  Gln  Glu  Pro  His  Asn
370                      375                      380

GACAGAAGCA   TCAGATATAG   TTTCTCCTGT   GCTGTTCCTG   AGAATGCATC   TTACAAGTCG   1270
TGGTTTGGAT   TGCTTGTGCA   GAATCATGGT   TTGTGCTTTC   AGAAGTATAT   CTAAATTAGT   1330
CCAAGTTATA   TGACTCCATA   TTGGAAAATA   ACTCAATGAG   TCGTGCTCTT   GAAATGGTCT   1390
TTTAAGCTTT   GAAATAAAGT   TCCACTTAAT   CCATGTAAAA   AAAAA                     1435
```

( 2 ) INFORMATION FOR SEQ ID NO: 11:

( i ) SEQUENCE CHARACTERISTICS:

( A ) LENGTH: 1307 base pairs ( B ) TYPE: nucleic acid
( C ) STRANDEDNESS: double
( D ) TOPOLOGY: linear ( i i ) MOLECULE TYPE: cDNA to mRNA ( x i ) SEQUENCE DESCRIPTION: SEQ ID NO: 11:

```
GCTCGCCTCC  CACATTTTCT  TCTTCGATCC  CGAAAAG ATG TTG AAG CTC TCG TGT        55
                                            Met Leu Lys Leu Ser Cys
                                             1               5

AAT GCG ACT GAT AAG TTA CAG ACC CTC TTC TCG CAT TCT CAT CAA CCG            103
Asn Ala Thr Asp Lys Leu Gln Thr Leu Phe Ser His Ser His Gln Pro
                 10              15              20

GAT CCG GCA CAC CGG AGA ACC GTC TCC TCC GTG TCG TGC TCT CAT CTG            151
Asp Pro Ala His Arg Arg Thr Val Ser Ser Val Ser Cys Ser His Leu
             25              30              35

AGG AAA CCG GTT CTC GAT CCT TTG CGA GCG ATC GTA TCT GCT GAT CAA            199
Arg Lys Pro Val Leu Asp Pro Leu Arg Ala Ile Val Ser Ala Asp Gln
         40              45              50

GGA AGT GTG ATT CGA GCA GAA CAA GGT TTG GGC TCA CTC GCG GAT CAG            247
Gly Ser Val Ile Arg Ala Glu Gln Gly Leu Gly Ser Leu Ala Asp Gln
 55              60              65              70

CTC CGA TTG GGT AGC TTG ACG GAG GAT GGT TTG TCG TAT AAG GAG AAG            295
Leu Arg Leu Gly Ser Leu Thr Glu Asp Gly Leu Ser Tyr Lys Glu Lys
                 75              80              85

TTC ATC GTC AGA TCC TAC GAA GTG GGG AGT AAC AAG ACC GCC ACT GTC            343
Phe Ile Val Arg Ser Tyr Glu Val Gly Ser Asn Lys Thr Ala Thr Val
             90              95             100

GAA ACC GTC GCT AAT CTT TTG CAG GAG GTG GGA TGT AAT CAT GCG CAG            391
Glu Thr Val Ala Asn Leu Leu Gln Glu Val Gly Cys Asn His Ala Gln
        105             110             115

AGC GTT GGA TTC TCG ACT GAT GGG TTT GCG ACA ACA CCG ACC ATG AGG            439
Ser Val Gly Phe Ser Thr Asp Gly Phe Ala Thr Thr Pro Thr Met Arg
        120             125             130

AAA CTG CAT CTC ATT TGG GTC ACT GCG AGA ATG CAT ATA GAG ATC TAC            487
Lys Leu His Leu Ile Trp Val Thr Ala Arg Met His Ile Glu Ile Tyr
135             140             145             150

AAG TAC CCT GCT TGG GGT GAT GTG GTT GAG ATA GAG ACA TGG TGT CAG            535
Lys Tyr Pro Ala Trp Gly Asp Val Val Glu Ile Glu Thr Trp Cys Gln
                155             160             165

AGT GAA GGA AGG ATC GGG ACT AGG CGT GAT TGG ATT CTT AAG GAT GTT            583
Ser Glu Gly Arg Ile Gly Thr Arg Arg Asp Trp Ile Leu Lys Asp Val
            170             175             180

GCT ACG GGT GAA GTC ACT GGC CGT GCT ACA AGC AAG TGG GTG ATG ATG            631
Ala Thr Gly Glu Val Thr Gly Arg Ala Thr Ser Lys Trp Val Met Met
        185             190             195

AAC CAA GAC ACA AGA CGG CTT CAG AAA GTT TCT GAT GAT GTT CGG GAC            679
Asn Gln Asp Thr Arg Arg Leu Gln Lys Val Ser Asp Asp Val Arg Asp
        200             205             210

GAG TAC TTG GTC TTC TGT CCT AAA GAA CTC AGA TTA GCA TTT CCT GAG            727
Glu Tyr Leu Val Phe Cys Pro Lys Glu Leu Arg Leu Ala Phe Pro Glu
215             220             225             230

GAG AAT AAC AGA AGC TTG AAG AAA ATT CCG AAA CTC GAA GAT CCA GCT            775
Glu Asn Asn Arg Ser Leu Lys Lys Ile Pro Lys Leu Glu Asp Pro Ala
                235             240             245

CAG TAT TCG ATG ATT GGG CTT AAG CCT AGA CGA GCT GAT CTC GAC ATG            823
Gln Tyr Ser Met Ile Gly Leu Lys Pro Arg Arg Ala Asp Leu Asp Met
            250             255             260

AAC CAG CAT GTC AAT AAT GTC ACC TAT ATT GGA TGG GTT CTT GAG AGC            871
Asn Gln His Val Asn Asn Val Thr Tyr Ile Gly Trp Val Leu Glu Ser
        265             270             275
```

| | | | | | | | | | | | | | | | | |
|---|---|---|---|---|---|---|---|---|---|---|---|---|---|---|---|---|
| ATA | CCT | CAA | GAG | ATT | GTA | GAC | ACG | CAC | GAA | CTT | CAG | GTC | ATA | ACT | CTG | 919 |
| Ile | Pro | Gln | Glu | Ile | Val | Asp | Thr | His | Glu | Leu | Gln | Val | Ile | Thr | Leu | |
| | 280 | | | | 285 | | | | | | 290 | | | | | |
| GAT | TAC | AGA | AGA | GAA | TGT | CAA | CAA | GAC | GAT | GTG | GTG | GAT | TCA | CTC | ACC | 967 |
| Asp | Tyr | Arg | Arg | Glu | Cys | Gln | Gln | Asp | Asp | Val | Val | Asp | Ser | Leu | Thr | |
| 295 | | | | | 300 | | | | | 305 | | | | | 310 | |
| ACT | ACC | ACC | TCA | GAG | ATT | GGT | GGG | ACC | AAT | GGC | TCT | GCA | TCA | TCA | GGC | 1015 |
| Thr | Thr | Thr | Ser | Glu | Ile | Gly | Gly | Thr | Asn | Gly | Ser | Ala | Ser | Ser | Gly | |
| | | | | | 315 | | | | 320 | | | | | 325 | | |
| ACA | CAG | GGG | CAA | AAC | GAT | AGC | CAG | TTC | TTA | CAT | CTC | TTA | AGG | CTG | TCT | 1063 |
| Thr | Gln | Gly | Gln | Asn | Asp | Ser | Gln | Phe | Leu | His | Leu | Leu | Arg | Leu | Ser | |
| | | | 330 | | | | | 335 | | | | | 340 | | | |
| GGA | GAC | GGT | CAG | GAG | ATC | AAC | CGC | GGG | ACA | ACC | CTG | TGG | AGA | AAG | AAG | 1111 |
| Gly | Asp | Gly | Gln | Glu | Ile | Asn | Arg | Gly | Thr | Thr | Leu | Trp | Arg | Lys | Lys | |
| | | 345 | | | | | | 350 | | | | | 355 | | | |
| CCC | TCC | AAT | CTC | TAAGCCATTT | CGTTCTTAAG | TTTCCTCTAT | CTGTGTCGCT | | | | | | | | | 1163 |
| Pro | Ser | Asn | Leu | | | | | | | | | | | | | |
| | 360 | | | | | | | | | | | | | | | |

CGATGCTTCA CGAGTCTAGT CAGGTCTCAT TTTTTCAAT CTAAATTTGG GTTAGACTAG 1223

AGAACTGGAA TTATTGGAAT TTATGAGTTT TCGTTCTTGT TTCTGTACAA ATCTTGAGGA 1283

TTGAAGCCAA ACCCATTTCA TCTT 1307

( 2 ) INFORMATION FOR SEQ ID NO: 12:

( i ) SEQUENCE CHARACTERISTICS:
      ( A ) LENGTH: 1856 base pairs
      ( B ) TYPE: nucleic acid
      ( C ) STRANDEDNESS: double
      ( D ) TOPOLOGY: linear ( i i ) MOLECULE TYPE: cDNA to mRNA ( x i ) SEQUENCE DESCRIPTION: SEQ ID NO: 12:

TTGGCAGATC CAAAATGAAG CAATGCCGTC TTCTTTGCTG AATATTTTTA CGGCGTTTGG 60

ATAATTTTAT TCTTGTTTCT TTTCATCATT TATTTGTTTC TCGCTGGTTA AGTACACTAC 120

| | | | | | | | | | | | | |
|---|---|---|---|---|---|---|---|---|---|---|---|---|
| AGGTGGTTCC CTCTACATCT TCAAG | ATG | GCT | TCT | ACT | GCT | GCT | ACT | GCT | GCT | | | 172 |
| | Met | Ala | Ser | Thr | Ala | Ala | Thr | Ala | Ala | | | |
| | 1 | | | | 5 | | | | | | | |

| | | | | | | | | | | | | | | | | |
|---|---|---|---|---|---|---|---|---|---|---|---|---|---|---|---|---|
| TTT | TTT | CCA | GTT | TCT | TCA | TCA | ACA | GAC | TCT | GTT | GCC | AAA | CCC | AAA | AAT | 220 |
| Phe | Phe | Pro | Val | Ser | Ser | Ser | Thr | Asp | Ser | Val | Ala | Lys | Pro | Lys | Asn | |
| 10 | | | | | 15 | | | | | 20 | | | | | 25 | |
| ATT | GGA | TCT | GCT | GGG | TTG | GGA | GGT | CTC | AAA | TCG | AAA | TCC | TCT | TCT | GGG | 268 |
| Ile | Gly | Ser | Ala | Gly | Leu | Gly | Gly | Leu | Lys | Ser | Lys | Ser | Ser | Ser | Gly | |
| | | | | 30 | | | | | 35 | | | | | 40 | | |
| CGT | TTG | CAG | GTT | AAG | GCT | ACT | GCC | CAA | GCC | CCT | TCT | AAA | ATA | AAT | GGT | 316 |
| Arg | Leu | Gln | Val | Lys | Ala | Thr | Ala | Gln | Ala | Pro | Ser | Lys | Ile | Asn | Gly | |
| | | | 45 | | | | | 50 | | | | | 55 | | | |
| ACT | TCG | GTT | GGT | TTG | ACA | AAA | CCT | GTG | GAA | GGC | CTG | AAG | AAT | GAG | GAT | 364 |
| Thr | Ser | Val | Gly | Leu | Thr | Lys | Pro | Val | Glu | Gly | Leu | Lys | Asn | Glu | Asp | |
| | | | 60 | | | | 65 | | | | | 70 | | | | |
| GAT | ATG | CCT | TCA | CCT | CCC | CCA | AGA | ACT | TTT | ATT | AAT | CAA | TTA | CCA | GAC | 412 |
| Asp | Met | Pro | Ser | Pro | Pro | Pro | Arg | Thr | Phe | Ile | Asn | Gln | Leu | Pro | Asp | |
| | | 75 | | | | | 80 | | | | | 85 | | | | |
| TGG | AGC | ATG | CTT | CTT | GCT | GCC | ATA | ACA | ACC | ATA | TTC | TTG | GCG | GCA | GAA | 460 |
| Trp | Ser | Met | Leu | Leu | Ala | Ala | Ile | Thr | Thr | Ile | Phe | Leu | Ala | Ala | Glu | |
| 90 | | | | | 95 | | | | | 100 | | | | | 105 | |
| AAA | CAG | TGG | ATG | ATG | CTG | GAT | TGG | AAA | CCA | AGA | AGG | TCT | GAT | ATG | CTT | 508 |
| Lys | Gln | Trp | Met | Met | Leu | Asp | Trp | Lys | Pro | Arg | Arg | Ser | Asp | Met | Leu | |
| | | | | 110 | | | | | 115 | | | | | 120 | | |
| ATT | GAT | CCA | TTT | GGA | ATT | GGG | AGA | ATT | GTC | CAA | GAT | GGT | CTC | ATA | TTC | 556 |

```
Ile Asp Pro Phe Gly Ile Gly Arg Ile Val Gln Asp Gly Leu Ile Phe
            125                 130                 135

AGA CAA AAT TTT TCG ATT AGA TCC TAT GAA ATA GGT GCT GAT CGT ACT          604
Arg Gln Asn Phe Ser Ile Arg Ser Tyr Glu Ile Gly Ala Asp Arg Thr
        140                 145                 150

GCC TCT ATA GAG ACA TTG ATG AAT CAT TTA CAG GAA ACA GCT CTT AAT          652
Ala Ser Ile Glu Thr Leu Met Asn His Leu Gln Glu Thr Ala Leu Asn
        155                 160                 165

CAT GTT AAG ACT GCC GGT CTT CTT GGC GAT GGC TTT GGT GCA ACC CCA          700
His Val Lys Thr Ala Gly Leu Leu Gly Asp Gly Phe Gly Ala Thr Pro
170                 175                 180                 185

GAG ATG TGC AAA AAG AAC CTG ATA TGG GTG GTT ACC CGA ATG CAG GTT          748
Glu Met Cys Lys Lys Asn Leu Ile Trp Val Val Thr Arg Met Gln Val
                190                 195                 200

GTT GTA GAT CGC TAT CCT ACC TGG GGT GAT GTT GTT GAG GTA GAT ACT          796
Val Val Asp Arg Tyr Pro Thr Trp Gly Asp Val Val Glu Val Asp Thr
            205                 210                 215

TGG GTT AGT GCA TCT GGA AAG AAT GGT ATG CGC CGT GAT TGG CTT GTC          844
Trp Val Ser Ala Ser Gly Lys Asn Gly Met Arg Arg Asp Trp Leu Val
            220                 225                 230

CGT GAT GGT CAA ACA GGG GAA ACT TTA ACA AGA GCT TCC AGT GTG TGG          892
Arg Asp Gly Gln Thr Gly Glu Thr Leu Thr Arg Ala Ser Ser Val Trp
235                 240                 245

GTG ACG ATG AAT AAA CAG ACT AGG AGA TTA TCC AAA ATT CCA GAC GAA          940
Val Thr Met Asn Lys Gln Thr Arg Arg Leu Ser Lys Ile Pro Asp Glu
250                 255                 260                 265

GTC AGG GGG GAA ATT GAG CCT TAT TTT GTG AAC TCT GAT CCT GTT GTT          988
Val Arg Gly Glu Ile Glu Pro Tyr Phe Val Asn Ser Asp Pro Val Val
                270                 275                 280

GAT GAG GAT AGT AGA AAA TTA CCA AAA CTT GAT GAC AAC ACA GCT GAT         1036
Asp Glu Asp Ser Arg Lys Leu Pro Lys Leu Asp Asp Asn Thr Ala Asp
            285                 290                 295

TAT GTT TGC AGA GGT TTA ACT CCT CGA TGG AGT GAT TTA GAT GTC AAC         1084
Tyr Val Cys Arg Gly Leu Thr Pro Arg Trp Ser Asp Leu Asp Val Asn
            300                 305                 310

CAG CAT GTT AAC AAC GTG AAG TAC ATT GGC TGG ATC CTC GAG AGT GCT         1132
Gln His Val Asn Asn Val Lys Tyr Ile Gly Trp Ile Leu Glu Ser Ala
315                 320                 325

CCA CAG GCA ATC TTG GAG AGT CAT GAG CTT GCA TCC ATG ACT TTG GAG         1180
Pro Gln Ala Ile Leu Glu Ser His Glu Leu Ala Ser Met Thr Leu Glu
330                 335                 340                 345

TAT CGG AGG GAG TGT GGG AAG GAC AGT GTG TTG CAG TCC CTT ACT GCT         1228
Tyr Arg Arg Glu Cys Gly Lys Asp Ser Val Leu Gln Ser Leu Thr Ala
                350                 355                 360

GTC TCC AGC TCT GAT AAC GGG AAT TTG GCC CTC TCT GGT GGT GCA GAG         1276
Val Ser Ser Ser Asp Asn Gly Asn Leu Ala Leu Ser Gly Gly Ala Glu
            365                 370                 375

TGC CAG CAC ATG CTA CGA CAT GAG GAC GGG CCC GAA ATA GTG AGA GGA         1324
Cys Gln His Met Leu Arg His Glu Asp Gly Pro Glu Ile Val Arg Gly
            380                 385                 390

AGG ACT GAG TGG AGG CCT AAA TAT GCA AAC AAC TTG GGG AAT GTT GGT         1372
Arg Thr Glu Trp Arg Pro Lys Tyr Ala Asn Asn Leu Gly Asn Val Gly
395                 400                 405

GAG GTT CCG GTA GGA AGT GCA TAAAACT TGATCTTTGT GGCAACGAGG              1420
Glu Val Pro Val Gly Ser Ala
410                 415

CAACAGTCAC ATTCCTTGTG TAGAATCCTG CTTTTGTTCC TGGATGATTT ATATGCTTCT       1480

TTATATATAA TGCCTTATTT GTCTCACTTG GTGTAAGTTG AATGTAATTA GCCCTGCTGA       1540

AATCTCGTTA TTACTCTCAT CTCAACCCAA CCAATTCAAC TAGCTCTCTT CCCAGGATGC       1600
```

```
AGTGCAAAGA  TAAATGACTT  GTATAGGGGG  AAATTTAAGG  GTCTCTTGTG  TTTGTCCTTG    1660

CCTAACCTGT  TGACGGGTGT  TAAAAGCTTG  GTGTTACTCA  AGATCTTTCG  TTGAACATGA    1720

TAATGTATAC  TTTAGTGGCT  TTTCTTTTTT  CTGGTTAGAT  TGGGCAAAAA  ATTATGCTGG    1780

TGGGTTTGTG  CTTCATATTT  TTAGCTGTAG  GGGAAGGCAA  TAATGATCCT  TATATATATA    1840

TATATATATT  TTTTGT                                                       1856
```

( 2 ) INFORMATION FOR SEQ ID NO: 13:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: synthetic oligonucleotide ( x i ) SEQUENCE DESCRIPTION: SEQ ID NO: 13:

```
CGTCTAGACA  TATGCCAAGG  ACTTTTATTA  AC                                     32
```

( 2 ) INFORMATION FOR SEQ ID NO: 14:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: synthetic oligonucleotide ( x i ) SEQUENCE DESCRIPTION: SEQ ID NO: 14:

```
CGGAATTCCG  AGACTGCAGT  AAGGCTAATC                                         30
```

( 2 ) INFORMATION FOR SEQ ID NO: 15:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: synthetic oligonucleotide ( x i ) SEQUENCE DESCRIPTION: SEQ ID NO: 15:

```
CGTCTAGACA  TATGCTTGAC  TGGAAACC                                           28
```

( 2 ) INFORMATION FOR SEQ ID NO: 16:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: synthetic oligonucleotide ( x i ) SEQUENCE DESCRIPTION: SEQ ID NO: 16:

```
CUACUACUAC  UAGCTCTAGA  GCTTGACTGG  AAACC                                  35
```

( 2 ) INFORMATION FOR SEQ ID NO: 17:

( i ) SEQUENCE CHARACTERISTICS:
        ( A ) LENGTH: 35 base pairs (B) TYPE: nucleic acid
        (C) STRANDEDNESS: single
        (D) TOPOLOGY: linear (ii) MOLECULE TYPE: other nucleic acid
        (A) DESCRIPTION: synthetic oligonucleotide (xi) SEQUENCE DESCRIPTION: SEQ ID NO: 17:

CAUCAUCAUC AUCCGAATTC GCAGTAAGGC TAATC                    35

(2) INFORMATION FOR SEQ ID NO: 18:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION: synthetic oligonucleotide (xi) SEQUENCE DESCRIPTION: SEQ ID NO: 18:

CUACUACUAC UAGCTCTAGA GCCAAGGACT TTTAT                    35

(2) INFORMATION FOR SEQ ID NO: 19:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: other nucleic acid
        (A) DESCRIPTION:; synthetic oligonucleotide (xi) SEQUENCE DESCRIPTION: SEQ ID NO: 19:

CUACUACUAC UAGCGCATAT GCCAAGGACT TTTAT                    35

(2) INFORMATION FOR SEQ ID NO: 20:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: synthetic oligonucleotide (xi) SEQUENCE DESCRIPTION: SEQ ID NO: 20:

GCTTGTCGAC AAGATGGCTT CTACTG                              26

(2) INFORMATION FOR SEQ ID NO: 21:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: synthetic oligonucleotide (xi) SEQUENCE DESCRIPTION: SEQ ID NO: 21:

GCGTAAGCTT GCATGCTGGT CA                                  22

(2) INFORMATION FOR SEQ ID NO: 22:

(i) SEQUENCE CHARACTERISTICS:
        (A) LENGTH: 375 amino acids (B) TYPE: amino acid
(D) TOPOLOGY: linear (ii) MOLECULE TYPE: protein (xi) SEQUENCE DESCRIPTION: SEQ ID NO: 22:

```
Met Ser Gln Phe Thr Cys Asn Val Thr Asp Gln Ile His Ile Arg Asn
 1               5                  10                  15
Gln Pro Gln Cys Arg Phe Met Gly Leu Pro Lys Pro Val Ser Ser Phe
            20                  25                  30
Arg Arg Arg Asn Asp Val Val Ser Ser Leu Pro Ile Pro Lys Pro
         35                  40              45
Arg Asn Pro Val Lys Ile Gln Ala Val Val Ser Glu His Gly Gly Pro
     50                  55                  60
Ala Val Thr Asp Thr Gly Ser Gly Thr Leu Ala Asp Arg Leu Arg Leu
 65                  70                  75                  80
Gly Ser Leu Thr Glu Asp Gly Leu Ser Tyr Lys Glu Lys Phe Ile Val
                 85                  90                  95
Arg Cys Tyr Glu Val Gly Ile Asn Lys Thr Ala Thr Val Glu Thr Ile
                100                 105                 110
Ala Asn Leu Leu Gln Glu Val Gly Cys Asn His Ala Gln Ser Val Gly
             115                 120                 125
Phe Ser Thr Asp Gly Phe Ala Thr Thr Pro Thr Met Arg Lys Phe Asn
     130                 135                 140
Leu Ile Trp Val Thr Ala Arg Met His Ile Glu Ile Leu Lys Tyr Pro
145                 150                 155                 160
Ala Trp Ser Asp Val Val Glu Ile Glu Thr Trp Cys His Ser Glu Gly
                 165                 170                 175
Arg Ile Gly Thr Arg Arg Asp Trp Ile Ile Lys Asp Tyr Ala Thr Gly
             180                 185                 190
Gln Val Ile Gly Arg Ala Thr Ser Lys Trp Val Met Met Asn Thr Val
         195                 200                 205
Thr Arg Arg Leu Gln Lys Ala Ser Asp Glu Val Arg Glu Glu Tyr Leu
210                 215                 220
Val Phe Cys Pro Arg Glu Pro Arg Tyr Ser Phe Pro Glu Lys Asp Asn
225                 230                 235                 240
Ala Ser Leu Arg Lys Ile Ser Lys Leu Glu Asp Pro Ala Glu Tyr Ser
             245                 250                 255
Arg Thr Gly Leu Met Pro Arg Arg Ala Asp Leu Asp Met Asn Gln His
             260                 265                 270
Val Asn Asn Val Thr Tyr Ile Gly Trp Val Leu Glu Ser Met Pro Gln
         275                 280                 285
Asp Ile Ile Asp Thr His Glu Leu Gln Thr Ile Thr Leu Asp Tyr Arg
     290                 295                 300
Arg Glu Cys Gln Arg Asp Asp Ile Val Asp Ser Leu Thr Ser Pro Glu
305                 310                 315                 320
Leu Ile Glu Asp Ser Asp Ala Ile Ser Asn Leu Lys Gly Ala Asn Gly
             325                 330                 335
Ser Pro Ala Thr Gly Asp Lys Glu Asp Tyr Arg Gln Phe Leu His Leu
             340                 345                 350
Leu Arg Leu Ser Ser Asp Gly Ser Glu Ile Asn Arg Gly Arg Thr Glu
         355                 360                 365
Trp Arg Arg Lys Pro Gly Arg
370                 375
```

( 2 ) INFORMATION FOR SEQ ID NO: 23:

( i ) SEQUENCE CHARACTERISTICS:
        ( A ) LENGTH: 417 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 23:

```
Met Ala Ser Thr Ala Ala Thr Ala Cys Phe Phe Pro Val Ser Ser Pro
 1               5                  10                  15
Ser Ser Asp Ser Val Ala Lys Thr Lys Asn Ile Gly Ser Ala Ser Leu
            20                  25                  30
Gly Gly Met Lys Ala Lys Ser Ser Ser Gly Gly Leu Gln Val Lys Ala
        35                  40                  45
Ser Ala Gln Ala Pro Ser Lys Ile Asn Gly Thr Ser Val Gly Leu Thr
    50                  55                  60
Lys Pro Ser Glu Ser Leu Lys Asn Glu Asp Met Pro Ser Ser His
65                  70                  75                  80
Pro Arg Thr Phe Ile Asn Gln Leu Pro Asp Trp Ser Met Leu Leu Ala
                85                  90                  95
Ala Ile Thr Thr Ile Phe Leu Ala Ala Glu Lys Gln Trp Met Met Leu
            100                 105                 110
Asp Trp Lys Pro Arg Arg Ser Asp Met Leu Ile Asp Pro Phe Gly Ile
        115                 120                 125
Gly Arg Ile Val Gln Asp Gly Leu Ile Phe Arg Gln Asn Phe Ser Ile
    130                 135                 140
Arg Ser Tyr Glu Ile Gly Ala Asp Arg Thr Ala Ser Ile Glu Thr Leu
145                 150                 155                 160
Met Asn His Leu Gln Glu Thr Ala Leu Asn His Val Lys Ser Ala Gly
                165                 170                 175
Leu Leu Gly Asp Gly Phe Gly Ser Thr Pro Gly Met Cys Lys Lys Asn
            180                 185                 190
Leu Ile Trp Val Val Thr Arg Met Gln Val Val Val Asp Arg Tyr Pro
        195                 200                 205
Thr Trp Gly Asp Val Val Glu Val Asp Ser Trp Val Ser Ala Ser Gly
    210                 215                 220
Lys Asn Gly Met Arg Arg Asp Trp Leu Ala Arg Asp Ser Lys Thr Gly
225                 230                 235                 240
Glu Thr Leu Thr Arg Ala Ser Ser Val Trp Val Met Met Asn Lys Gln
                245                 250                 255
Thr Arg Arg Leu Ser Lys Ile Pro Asp Glu Val Arg Gly Glu Ile Glu
            260                 265                 270
Pro Tyr Phe Val Asn Ser Asp Pro Val Val Asp Glu Asp Gly Arg Lys
        275                 280                 285
Leu Pro Lys Leu Asp Asp Asn Thr Ala Asp Tyr Val His Arg Gly Leu
    290                 295                 300
Thr Pro Arg Trp Ser Asp Leu Asp Val Asn Gln His Val Asn Asn Val
305                 310                 315                 320
Lys Tyr Ile Gly Trp Ile Leu Glu Ser Ala Pro Gln Ala Ile Leu Glu
                325                 330                 335
Ser His Glu Leu Ala Ser Met Thr Leu Glu Tyr Arg Arg Glu Cys Gly
            340                 345                 350
Lys Asp Ser Val Leu Lys Ser Leu Thr Ala Val Ser Gly Ser Asp Val
        355                 360                 365
```

-continued

| | | | | | | | | | | | | | | |
|---|---|---|---|---|---|---|---|---|---|---|---|---|---|---|
| Gly | Asn | Leu | Ser | His | Leu | Gly | Arg | Val | Glu | Cys | Gln | His | Met | Leu | Gln |
| | 370 | | | | | 375 | | | | | 380 | | | | |
| Leu | Glu | Asp | Gly | Ala | Glu | Ile | Val | Arg | Gly | Arg | Thr | Glu | Trp | Arg | Pro |
| 385 | | | | | 390 | | | | | 395 | | | | | 400 |
| Lys | Tyr | Ala | Asn | Asn | Phe | Gly | Asn | Val | Gly | Glu | Val | Pro | Ala | Glu | Ser |
| | | | | 405 | | | | | 410 | | | | | 415 | |
| Ala | | | | | | | | | | | | | | | |

( 2 ) INFORMATION FOR SEQ ID NO: 24:

( i ) SEQUENCE CHARACTERISTICS:
        ( A ) LENGTH: 375 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 24:

| | | | | | | | | | | | | | | |
|---|---|---|---|---|---|---|---|---|---|---|---|---|---|---|
| Met | Asp | Ala | Lys | Thr | His | Ala | Gln | Ala | Val | Pro | Lys | Ile | Asn | Gly | Thr |
| 1 | | | | 5 | | | | | 10 | | | | | 15 | |
| Lys | Val | Asp | Thr | Arg | Arg | Asn | Asp | Ser | Ser | Arg | Gly | Glu | Asp | Glu | Ala |
| | | | 20 | | | | | 25 | | | | | 30 | | |
| Ile | Tyr | Thr | Thr | Ser | Ser | Ala | Pro | Arg | Thr | Phe | Tyr | Asn | Gln | Leu | Pro |
| | | 35 | | | | | 40 | | | | | 45 | | | |
| Asp | Trp | Ser | Met | Leu | Leu | Ala | Ala | Ile | Thr | Thr | Ile | Phe | Leu | Ala | Ala |
| | 50 | | | | | 55 | | | | | 60 | | | | |
| Glu | Lys | Gln | Trp | Thr | Leu | Ile | Asp | Trp | Lys | Pro | Arg | Arg | Pro | Asp | Met |
| 65 | | | | | 70 | | | | | 75 | | | | | 80 |
| Leu | Ser | Asp | Ala | Phe | Gly | Leu | Gly | Lys | Ile | Val | Gln | Asp | Gly | Leu | Val |
| | | | | 85 | | | | | 90 | | | | | 95 | |
| Phe | Thr | Gln | Asn | Phe | Pro | Ile | Arg | Ser | Tyr | Glu | Ile | Gly | Ala | Asp | Arg |
| | | | 100 | | | | | 105 | | | | | 110 | | |
| Thr | Ala | Ser | Ile | Glu | Thr | Leu | Met | Asn | His | Leu | Gln | Glu | Thr | Ala | Leu |
| | | | 115 | | | | 120 | | | | | 125 | | | |
| Asn | His | Val | Lys | Met | Ala | Gly | Leu | Leu | Gly | Asp | Gly | Phe | Gly | Ala | Thr |
| | 130 | | | | | 135 | | | | | 140 | | | | |
| Pro | Glu | Met | Ser | Lys | Lys | Asn | Leu | Ile | Trp | Val | Val | Thr | Lys | Met | Gln |
| 145 | | | | | 150 | | | | | 155 | | | | | 160 |
| Val | Leu | Val | Glu | His | Tyr | Pro | Lys | Trp | Gly | Asp | Val | Val | Glu | Val | Asp |
| | | | | 165 | | | | | 170 | | | | | 175 | |
| Thr | Trp | Val | Ser | Ala | Ser | Gly | Lys | Asn | Gly | Met | Arg | Arg | Asp | Trp | His |
| | | | 180 | | | | | 185 | | | | | 190 | | |
| Val | His | Asn | Ile | Arg | Thr | Gly | Gln | Thr | Val | Met | Arg | Ala | Thr | Ser | Val |
| | | 195 | | | | | 200 | | | | | 205 | | | |
| Trp | Val | Met | Met | Asn | Lys | Val | Thr | Arg | Arg | Leu | Ser | Lys | Met | Pro | Glu |
| | 210 | | | | | 215 | | | | | 220 | | | | |
| Glu | Val | Arg | Ala | Glu | Ile | Gly | Pro | Phe | Phe | Val | Asp | Arg | Gly | Pro | Ile |
| 225 | | | | | 230 | | | | | 235 | | | | | 240 |
| Ile | Asp | Glu | Asp | Ser | Arg | Lys | Leu | Pro | Lys | Leu | Asp | Glu | Glu | Ser | Ala |
| | | | | 245 | | | | | 250 | | | | | 255 | |
| Asn | His | Val | Lys | Asn | Gly | Leu | Thr | Pro | Arg | Trp | Ser | Asp | Leu | Asp | Val |
| | | | 260 | | | | | 265 | | | | | 270 | | |
| Asn | Gln | His | Val | Asn | Asn | Val | Lys | Tyr | Ile | Gly | Trp | Ile | Leu | Glu | Ser |
| | | 275 | | | | | 280 | | | | | 285 | | | |
| Ala | Pro | Ile | Ser | Leu | Leu | Glu | Ser | His | Glu | Leu | Ala | Ser | Met | Thr | Leu |
| | 290 | | | | | 295 | | | | | 300 | | | | |

| Glu 305 | Tyr | Arg | Arg | Glu | Cys 310 | Gly | Arg | Asp | Ser | Val 315 | Leu | Gln | Ser | Leu | Thr 320 |
|---|---|---|---|---|---|---|---|---|---|---|---|---|---|---|---|
| Ala | Val | Thr | Ser | Asp 325 | Cys | Thr | Thr | Asp | Ser 330 | His | Glu | Lys | Thr 335 | | Phe |
| Thr | Glu | Cys | Asn 340 | His | Leu | Leu | Arg | Leu 345 | Asp | Cys | Gly | Ala | Glu 350 | Ile | Val |
| Arg | Gly | His 355 | Thr | Glu | Trp | Arg | Pro 360 | Lys | Asn | Ala | Gln | Asp 365 | Leu | Ala | Asn |
| Met | Gly 370 | Pro | Pro | Ser | Ile | Asn 375 | | | | | | | | | |

( 2 ) INFORMATION FOR SEQ ID NO: 25:

( i ) SEQUENCE CHARACTERISTICS:
        ( A ) LENGTH: 423 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 25:

| Met 1 | Ala | Ala | Phe | Ala 5 | Ser | Ser | Ala | Phe | Phe 10 | Pro | Thr | Pro | Ser | Gly 15 | Pro |
|---|---|---|---|---|---|---|---|---|---|---|---|---|---|---|---|
| Asn | Ser | Ser | Leu 20 | Lys | Ser | Ser | Lys | Pro 25 | Val | Asn | Gly | Asn | Gln 30 | Asp | Ser |
| Leu | Gln | Val 35 | Asn | Gly | Leu | Val | Ser 40 | Lys | Lys | Ser | Leu | Ser 45 | Ser | Lys | Ser |
| Met | Asp 50 | Ala | Lys | Thr | His | Ala 55 | Gln | Ala | Val | Pro | Lys 60 | Ile | Asn | Gly | Thr |
| Lys 65 | Val | Asp | Thr | Arg | Arg 70 | Asn | Asp | Ser | Ser | Arg 75 | Gly | Glu | Asp | Glu | Ala 80 |
| Ile | Tyr | Thr | Thr | Ser 85 | Ser | Ala | Pro | Arg | Thr 90 | Phe | Tyr | Asn | Gln | Leu 95 | Pro |
| Asp | Trp | Ser | Met 100 | Leu | Leu | Ala | Ala | Ile 105 | Thr | Thr | Ile | Phe 110 | Leu | Ala | Ala |
| Glu | Lys | Gln 115 | Trp | Thr | Leu | Ile | Asp 120 | Trp | Lys | Pro | Arg | Arg 125 | Pro | Asp | Met |
| Leu | Ser 130 | Asp | Ala | Cys | Gly | Leu 135 | Gly | Lys | Ile | Ala | Gln 140 | Asp | Gly | Leu | Val |
| Phe 145 | Thr | Gln | Asn | Ser | Pro 150 | Ile | Arg | Ser | Tyr | Glu 155 | Ile | Gly | Ala | Xaa | Arg 160 |
| Thr | Ala | Ser | Ile | Glu 165 | Thr | Leu | Met | Thr | His 170 | Leu | Gln | Glu | Thr | Ala 175 | Leu |
| Thr | His | Val | Lys 180 | Met | Ala | Gly | Leu | Leu 185 | Gly | Asp | Gly | Phe | Gly 190 | Ala | Thr |
| Pro | Glu | Met 195 | Ser | Lys | Lys | Asn | Leu 200 | Ile | Trp | Val | Val | Thr 205 | Lys | Met | Gln |
| Val | Leu 210 | Val | Glu | His | Tyr | Pro 215 | Lys | Trp | Gly | Asp | Val 220 | Val | Glu | Val | Asp |
| Thr 225 | Trp | Val | Ser | Ala | Ser 230 | Gly | Lys | Asn | Gly | Met 235 | Arg | Arg | Asp | Trp | His 240 |
| Val | His | Asn | Ile | Arg 245 | Thr | Gly | Gln | Thr | Val 250 | Met | Arg | Ala | Thr | Ser 255 | Val |
| Trp | Val | Met | Met 260 | Asn | Lys | Val | Thr | Arg 265 | Arg | Leu | Ser | Lys 270 | Met | Pro | Glu |
| Glu | Val | Arg 275 | Ala | Glu | Ile | Gly | Pro 280 | Phe | Phe | Val | Asp | Arg 285 | Gly | Pro | Ile |

```
Ile  Asp  Glu  Asp  Ser  Arg  Lys  Leu  Pro  Lys  Leu  Asp  Glu  Glu  Ser  Ala
     290                 295                 300

Asn  His  Val  Lys  Asn  Gly  Leu  Thr  Pro  Arg  Trp  Ser  Asp  Leu  Asp  Val
305                      310                 315                      320

Asn  Gln  His  Val  Asn  Asn  Val  Lys  Tyr  Ile  Gly  Trp  Ile  Leu  Glu  Ser
                    325                 330                      335

Ala  Pro  Ile  Ser  Leu  Leu  Glu  Ser  His  Glu  Leu  Ala  Ser  Met  Thr  Leu
                    340                 345                      350

Glu  Tyr  Arg  Arg  Glu  Cys  Gly  Arg  Asp  Ser  Val  Leu  Gln  Ser  Leu  Thr
               355                 360                      365

Ala  Val  Thr  Ser  Asp  Cys  Thr  Thr  Asp  Thr  Ser  Arg  Glu  Lys  Thr  Phe
     370                      375                      380

Thr  Glu  Cys  Asn  His  Leu  Leu  Arg  Leu  Asp  Cys  Gly  Ala  Glu  Ile  Val
385                      390                 395                           400

Arg  Gly  His  Thr  Glu  Trp  Arg  Pro  Lys  Asn  Ala  Gln  Asp  Leu  Ala  Asn
                    405                 410                      415

Met  Gly  Pro  Pro  Ser  Met  Asn
               420
```

( 2 ) INFORMATION FOR SEQ ID NO: 26:

( i ) SEQUENCE CHARACTERISTICS:
        ( A ) LENGTH: 382 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 26:

```
Met  Ala  Thr  Thr  Ser  Leu  Ala  Ser  Ala  Phe  Cys  Ser  Met  Lys  Ala  Val
1                        5                   10                      15

Met  Leu  Ala  Arg  Asp  Gly  Arg  Gly  Met  Lys  Pro  Arg  Ser  Ser  Asp  Leu
               20                  25                      30

Gln  Leu  Arg  Ala  Gly  Asn  Ala  Pro  Thr  Ser  Leu  Lys  Met  Ile  Asn  Gly
               35                  40                      45

Thr  Lys  Phe  Ser  Tyr  Thr  Glu  Ser  Leu  Lys  Arg  Leu  Pro  Asp  Trp  Ser
     50                       55                      60

Met  Leu  Phe  Ala  Val  Ile  Thr  Thr  Ile  Phe  Ser  Ala  Ala  Glu  Lys  Gln
65                       70                  75                           80

Trp  Thr  Asn  Leu  Glu  Trp  Lys  Pro  Lys  Pro  Lys  Leu  Pro  Gln  Leu  Leu
                    85                  90                      95

Asp  Asp  His  Phe  Gly  Leu  His  Gly  Leu  Val  Phe  Arg  Arg  Thr  Phe  Ala
               100                 105                      110

Ile  Arg  Ser  Tyr  Glu  Val  Gly  Pro  Asp  Arg  Ser  Thr  Ser  Ile  Leu  Ala
          115                      120                 125

Val  Met  Asn  His  Met  Gln  Glu  Ala  Thr  Leu  Asn  His  Ala  Lys  Ser  Val
     130                      135                 140

Gly  Ile  Leu  Gly  Asp  Gly  Phe  Gly  Thr  Thr  Leu  Glu  Met  Ser  Lys  Arg
145                      150                 155                           160

Asp  Leu  Met  Trp  Val  Val  Arg  Arg  Thr  His  Val  Ala  Val  Glu  Arg  Tyr
               165                      170                      175

Pro  Thr  Trp  Gly  Asp  Thr  Val  Glu  Val  Glu  Cys  Trp  Ile  Gly  Ala  Ser
               180                 185                      190

Gly  Asn  Asn  Gly  Met  Arg  Arg  Asp  Phe  Leu  Val  Arg  Asp  Cys  Lys  Thr
          195                      200                 205

Gly  Glu  Ile  Leu  Thr  Arg  Cys  Thr  Ser  Leu  Ser  Val  Leu  Met  Asn  Thr
```

```
            210                     215                      220
Arg Thr Arg Arg Leu Ser Thr Ile Pro Asp Glu Val Arg Gly Glu Ile
225                     230                 235                 240

Gly Pro Ala Phe Ile Asp Asn Val Ala Val Lys Asp Asp Glu Ile Lys
                245                 250                 255

Lys Leu Gln Lys Leu Asn Asp Ser Thr Ala Asp Tyr Ile Gln Gly Gly
                260                 265                 270

Leu Thr Pro Arg Trp Asn Asp Leu Asp Val Asn Gln His Val Asn Asn
            275                 280                 285

Leu Lys Tyr Val Ala Trp Val Phe Glu Thr Val Pro Asp Ser Ile Phe
        290                 295                 300

Glu Ser His His Ile Ser Ser Phe Thr Leu Glu Tyr Arg Arg Glu Cys
305                 310                 315                 320

Thr Arg Asp Ser Val Leu Arg Ser Leu Thr Thr Val Ser Gly Gly Ser
                325                 330                 335

Ser Glu Ala Gly Leu Val Cys Asp His Leu Leu Gln Leu Glu Gly Gly
                340                 345                 350

Ser Glu Val Leu Arg Ala Arg Thr Glu Trp Arg Pro Lys Leu Thr Asp
            355                 360                 365

Ser Phe Arg Gly Ile Ser Val Ile Pro Ala Glu Pro Arg Val
        370                 375                 380
```

(2) INFORMATION FOR SEQ ID NO: 27:

(i) SEQUENCE CHARACTERISTICS:
      (A) LENGTH: 415 amino acids
      (B) TYPE: amino acid
      (D) TOPOLOGY: linear (ii) MOLECULE TYPE: protein (xi) SEQUENCE DESCRIPTION: SEQ ID NO: 27:

```
Met Val Ala Ala Ala Ser Ser Ala Phe Phe Pro Val Pro Ala Pro
1               5                   10                  15

Gly Ala Ser Pro Lys Pro Gly Lys Phe Gly Asn Trp Pro Ser Ser Leu
                20                  25                  30

Ser Pro Ser Phe Lys Pro Lys Ser Ile Pro Asn Gly Gly Phe Gln Val
            35                  40                  45

Lys Ala Asn Asp Ser Ala His Pro Lys Ala Asn Gly Ser Ala Val Ser
        50                  55                  60

Leu Lys Ser Gly Ser Leu Asn Thr Gln Glu Asp Thr Ser Ser Ser Pro
65                  70                  75                  80

Pro Pro Arg Thr Phe Leu His Gln Leu Pro Asp Trp Ser Arg Leu Leu
            85                  90                  95

Thr Ala Ile Thr Thr Val Phe Val Lys Ser Lys Arg Pro Asp Met His
                100                 105                 110

Asp Arg Lys Ser Lys Arg Pro Asp Met Leu Val Asp Ser Phe Gly Leu
            115                 120                 125

Glu Ser Thr Val Gln Asp Gly Leu Val Phe Arg Gln Ser Phe Ser Ile
    130                 135                 140

Arg Ser Tyr Glu Ile Gly Thr Asp Arg Thr Ala Ser Ile Glu Thr Leu
145                 150                 155                 160

Met Asn His Leu Gln Glu Thr Ser Leu Asn His Cys Lys Ser Thr Gly
                165                 170                 175

Ile Leu Leu Asp Gly Phe Gly Arg Thr Leu Glu Met Cys Lys Arg Asp
            180                 185                 190
```

-continued

| | | | | | | | | | | | | | | |
|---|---|---|---|---|---|---|---|---|---|---|---|---|---|---|
| Leu | Ile | Trp 195 | Val | Val | Ile | Lys | Met 200 | Gln | Ile | Lys | Val | Asn 205 | Arg | Tyr | Pro |
| Ala | Trp 210 | Gly | Asp | Thr | Val | Glu 215 | Ile | Asn | Thr | Arg | Phe 220 | Ser | Arg | Leu | Gly |
| Lys 225 | Ile | Gly | Met | Gly | Arg 230 | Asp | Trp | Leu | Ile | Ser 235 | Asp | Cys | Asn | Thr | Gly 240 |
| Glu | Ile | Leu | Val | Arg 245 | Ala | Thr | Ser | Ala | Tyr 250 | Ala | Met | Met | Asn | Gln 255 | Lys |
| Thr | Arg | Arg | Leu 260 | Ser | Lys | Leu | Pro | Tyr 265 | Glu | Val | His | Gln 270 | Glu | Ile | Val |
| Pro | Leu | Phe 275 | Val | Asp | Ser | Pro | Val 280 | Ile | Glu | Asp | Ser | Asp 285 | Leu | Lys | Val |
| His | Lys 290 | Phe | Lys | Val | Lys | Thr 295 | Gly | Asp | Ser | Ile | Gln 300 | Lys | Gly | Leu | Thr |
| Pro 305 | Gly | Trp | Asn | Asp | Leu 310 | Asp | Val | Asn | Gln | His 315 | Val | Ser | Asn | Val | Lys 320 |
| Tyr | Ile | Gly | Trp | Ile 325 | Leu | Glu | Ser | Met | Pro 330 | Thr | Glu | Val | Leu | Glu 335 | Thr |
| Gln | Glu | Leu | Cys 340 | Ser | Leu | Ala | Leu | Glu 345 | Tyr | Arg | Arg | Glu 350 | Cys | Gly | Arg |
| Asp | Ser | Val 355 | Leu | Glu | Ser | Val | Thr 360 | Ala | Met | Asp | Pro | Ser 365 | Lys | Val | Gly |
| Val | Arg 370 | Ser | Gln | Tyr | Gln | His 375 | Leu | Leu | Arg | Leu | Glu 380 | Asp | Gly | Thr | Ala |
| Ile 385 | Val | Asn | Gly | Ala | Thr 390 | Glu | Trp | Arg | Pro | Lys 395 | Asn | Ala | Gly | Ala | Asn 400 |
| Gly | Ala | Ile | Ser | Thr 405 | Gly | Lys | Thr | Ser | Asn 410 | Gly | Asn | Ser | Val | Ser 415 | |

( 2 ) INFORMATION FOR SEQ ID NO: 28:

( i ) SEQUENCE CHARACTERISTICS:
        ( A ) LENGTH: 415 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 28:

| | | | | | | | | | | | | | | |
|---|---|---|---|---|---|---|---|---|---|---|---|---|---|---|
| Met 1 | Val | Ala | Thr | Ala 5 | Ala | Ser | Ser | Ala | Phe 10 | Phe | Pro | Leu | Pro | Ser 15 | Ala |
| Asp | Thr | Ser | Ser 20 | Arg | Pro | Gly | Lys | Leu 25 | Gly | Asn | Lys | Pro | Ser 30 | Ser | Leu |
| Ser | Pro | Leu 35 | Lys | Pro | Lys | Ser | Thr 40 | Pro | Asn | Gly | Gly | Leu 45 | Gln | Val | Lys |
| Ala | Asn 50 | Ala | Ser | Ala | Pro | Pro 55 | Lys | Ile | Asn | Gly | Ser 60 | Pro | Val | Gly | Leu |
| Lys 65 | Ser | Gly | Gly | Leu | Lys 70 | Thr | Gln | Glu | Asp | Ala 75 | His | Ser | Ala | Pro | Pro 80 |
| Pro | Arg | Thr | Phe | Ile 85 | Asn | Gln | Leu | Pro | Asp 90 | Trp | Ser | Met | Leu | Leu 95 | Ala |
| Ala | Ile | Thr | Thr 100 | Val | Phe | Leu | Ala | Ala 105 | Glu | Lys | Gln | Trp | Met 110 | Met | Leu |
| Asp | Trp | Lys 115 | Pro | Lys | Arg | Pro | Asp 120 | Met | Leu | Val | Asp | Pro 125 | Phe | Gly | Leu |
| Gly | Ser 130 | Ile | Val | Gln | Asp | Gly 135 | Leu | Val | Phe | Arg | Gln 140 | Asn | Phe | Ser | Ile |

| | | | | | | | | | | | | | | | |
|---|---|---|---|---|---|---|---|---|---|---|---|---|---|---|---|
| Arg | Ser | Tyr | Glu | Ile | Gly | Ala | Asp | Arg | Thr | Ala | Ser | Ile | Glu | Thr | Val |
| 145 | | | | 150 | | | | | 155 | | | | | | 160 |
| Met | Asn | His | Leu | Gln | Glu | Thr | Ala | Leu | Asn | His | Val | Lys | Ile | Ala | Gly |
| | | | | 165 | | | | | 170 | | | | | 175 | |
| Leu | Ser | Asn | Asp | Gly | Phe | Gly | Arg | Thr | Pro | Glu | Met | Tyr | Lys | Arg | Asp |
| | | | 180 | | | | | 185 | | | | | 190 | | |
| Leu | Ile | Trp | Val | Val | Ala | Lys | Met | Gln | Val | Met | Val | Asn | Arg | Tyr | Pro |
| | | 195 | | | | | 200 | | | | | 205 | | | |
| Thr | Trp | Gly | Asp | Thr | Val | Glu | Val | Asn | Thr | Trp | Val | Ala | Lys | Ser | Gly |
| | 210 | | | | | 215 | | | | | 220 | | | | |
| Lys | Asn | Gly | Met | Arg | Arg | Asp | Trp | Leu | Ile | Ser | Asp | Cys | Asn | Thr | Gly |
| 225 | | | | | 230 | | | | | 235 | | | | | 240 |
| Glu | Ile | Leu | Thr | Arg | Ala | Ser | Ser | Val | Trp | Val | Met | Met | Asn | Gln | Lys |
| | | | | 245 | | | | | 250 | | | | | 255 | |
| Thr | Arg | Arg | Leu | Ser | Lys | Ile | Pro | Asp | Glu | Val | Arg | Asn | Glu | Ile | Glu |
| | | | 260 | | | | | 265 | | | | | 270 | | |
| Pro | His | Phe | Val | Asp | Ser | Pro | Val | Ile | Glu | Asp | Asp | Asp | Arg | Lys | |
| | | 275 | | | | 280 | | | | | 285 | | | | |
| Leu | Pro | Lys | Leu | Asp | Glu | Lys | Thr | Ala | Asp | Ser | Ile | Arg | Lys | Gly | Leu |
| | 290 | | | | | 295 | | | | | 300 | | | | |
| Thr | Pro | Arg | Trp | Asn | Asp | Leu | Asp | Val | Asn | Gln | His | Val | Asn | Asn | Val |
| 305 | | | | | 310 | | | | | 315 | | | | | 320 |
| Lys | Tyr | Ile | Gly | Trp | Ile | Leu | Glu | Ser | Thr | Pro | Pro | Glu | Val | Leu | Glu |
| | | | | 325 | | | | | 330 | | | | | 335 | |
| Thr | Gln | Glu | Leu | Cys | Ser | Leu | Thr | Leu | Glu | Tyr | Arg | Arg | Glu | Cys | Gly |
| | | | 340 | | | | | 345 | | | | | 350 | | |
| Arg | Glu | Ser | Val | Leu | Glu | Ser | Leu | Thr | Ala | Met | Asp | Pro | Ser | Gly | Gly |
| | | 355 | | | | | 360 | | | | | 365 | | | |
| Gly | Tyr | Gly | Ser | Gln | Phe | Gln | His | Leu | Leu | Arg | Leu | Glu | Asp | Gly | Gly |
| | | 370 | | | | 375 | | | | | 380 | | | | |
| Glu | Ile | Val | Lys | Gly | Arg | Thr | Glu | Trp | Arg | Pro | Lys | Asn | Gly | Val | Ile |
| 385 | | | | | 390 | | | | | 395 | | | | | 400 |
| Asn | Gly | Val | Val | Pro | Thr | Gly | Glu | Ser | Ser | Pro | Gly | Asp | Tyr | Ser | |
| | | | | 405 | | | | | 410 | | | | | 415 | |

( 2 ) INFORMATION FOR SEQ ID NO: 29:

( i ) SEQUENCE CHARACTERISTICS:
        ( A ) LENGTH: 383 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 29:

| | | | | | | | | | | | | | | | |
|---|---|---|---|---|---|---|---|---|---|---|---|---|---|---|---|
| Glu | Phe | Gly | Thr | Arg | Gly | Ser | Gly | Ala | Leu | Gln | Val | Lys | Ala | Ser | Ser |
| 1 | | | | 5 | | | | | 10 | | | | | 15 | |
| Gln | Ala | Pro | Pro | Lys | Leu | Asn | Gly | Ser | Asn | Val | Gly | Leu | Val | Lys | Ser |
| | | | 20 | | | | | 25 | | | | | 30 | | |
| Ser | Gln | Ile | Val | Lys | Lys | Gly | Asp | Asp | Thr | Thr | Ser | Pro | Pro | Ala | Arg |
| | | | 35 | | | | | 40 | | | | | 45 | | |
| Thr | Phe | Ile | Asn | Gln | Leu | Pro | Asp | Trp | Ser | Met | Leu | Leu | Ala | Ala | Ile |
| | | | 50 | | | | | 55 | | | | | 60 | | |
| Thr | Thr | Leu | Phe | Leu | Ala | Ala | Glu | Lys | Gln | Trp | Met | Met | Leu | Asp | Trp |
| 65 | | | | | 70 | | | | | 75 | | | | | 80 |
| Lys | Pro | Lys | Arg | Pro | Asp | Met | Leu | Val | Asp | Pro | Phe | Gly | Leu | Gly | Arg |

```
                          85                        90                           95
Phe  Val  Gln  Asp  Gly  Leu  Val  Phe  Arg  Asn  Asn  Phe  Ser  Ile  Arg  Ser
              100                       105                      110

Tyr  Glu  Ile  Gly  Ala  Asp  Arg  Thr  Ala  Ser  Ile  Glu  Thr  Leu  Met  Asn
              115                       120                      125

His  Leu  Gln  Glu  Thr  Ala  Leu  Asn  His  Val  Lys  Ser  Val  Gly  Leu  Leu
     130                            135                     140

Glu  Asp  Gly  Leu  Gly  Ser  Thr  Arg  Glu  Met  Ser  Leu  Arg  Asn  Leu  Ile
145                            150                      155                      160

Trp  Val  Val  Thr  Lys  Met  Gln  Val  Ala  Val  Asp  Arg  Tyr  Pro  Thr  Trp
               165                      170                      175

Gly  Asp  Glu  Val  Gln  Val  Ser  Ser  Trp  Ala  Thr  Ala  Ile  Gly  Lys  Asn
               180                           185                     190

Gly  Met  Arg  Arg  Glu  Trp  Ile  Val  Thr  Asp  Phe  Arg  Thr  Gly  Glu  Thr
          195                           200                      205

Leu  Leu  Arg  Ala  Thr  Ser  Val  Trp  Val  Met  Met  Asn  Lys  Leu  Thr  Arg
     210                           215                      220

Arg  Ile  Ser  Lys  Ile  Pro  Glu  Glu  Val  Trp  His  Glu  Ile  Gly  Pro  Ser
225                            230                      235                      240

Phe  Ile  Asp  Ala  Pro  Pro  Leu  Pro  Thr  Val  Glu  Asp  Asp  Gly  Arg  Lys
                    245                      250                      255

Leu  Thr  Arg  Phe  Asp  Glu  Ser  Ser  Ala  Asp  Phe  Ile  Arg  Xaa  Gly  Leu
               260                           265                      270

Thr  Pro  Arg  Trp  Ser  Asp  Leu  Asp  Ile  Asn  Gln  His  Val  Asn  Asn  Val
          275                           280                      285

Lys  Tyr  Ile  Gly  Trp  Leu  Leu  Glu  Ser  Ala  Pro  Pro  Glu  Ile  His  Glu
     290                           295                      300

Ser  His  Glu  Ile  Ala  Ser  Leu  Thr  Leu  Glu  Tyr  Arg  Arg  Glu  Cys  Gly
305                            310                      315                      320

Arg  Asp  Ser  Val  Leu  Asn  Ser  Ala  Thr  Lys  Val  Ser  Asp  Ser  Ser  Gln
                    325                      330                      335

Leu  Gly  Lys  Ser  Ala  Val  Glu  Cys  Asn  His  Leu  Val  Arg  Leu  Gln  Asn
               340                           345                      350

Gly  Gly  Glu  Ile  Val  Lys  Gly  Arg  Thr  Val  Trp  Arg  Pro  Lys  Arg  Pro
          355                           360                      365

Leu  Tyr  Asn  Asp  Gly  Ala  Val  Val  Asp  Val  Xaa  Ala  Lys  Thr  Ser
     370                           375                      380
```

( 2 ) INFORMATION FOR SEQ ID NO: 30:

( i ) SEQUENCE CHARACTERISTICS:
        ( A ) LENGTH: 382 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 30:

```
Met  Ala  Thr  Thr  Ser  Leu  Ala  Ser  Ala  Phe  Cys  Ser  Met  Lys  Ala  Val
1                   5                        10                      15

Met  Leu  Ala  Arg  Asp  Gly  Arg  Gly  Met  Lys  Pro  Arg  Ser  Ser  Asp  Leu
               20                       25                      30

Gln  Leu  Arg  Ala  Gly  Asn  Ala  Gln  Thr  Ser  Leu  Lys  Met  Ile  Asn  Gly
          35                            40                      45

Thr  Lys  Phe  Ser  Tyr  Thr  Glu  Ser  Leu  Lys  Lys  Leu  Pro  Asp  Trp  Ser
     50                             55                           60
```

| | | | | | | | | | | | | | | | |
|---|---|---|---|---|---|---|---|---|---|---|---|---|---|---|---|
| Met 65 | Leu | Phe | Ala | Val | Ile 70 | Thr | Thr | Ile | Phe 75 | Ser | Ala | Ala | Glu | Lys | Gln 80 |
| Trp | Thr | Asn | Leu | Glu 85 | Trp | Lys | Pro | Lys 90 | Pro | Asn | Pro | Pro | Gln 95 | Leu | Leu |
| Asp | Asp | His | Phe 100 | Gly | Pro | His | Gly | Leu 105 | Val | Phe | Arg | Arg 110 | Thr | Phe | Ala |
| Ile | Arg | Ser 115 | Tyr | Glu | Val | Gly | Pro 120 | Asp | Arg | Ser | Thr | Ser 125 | Ile | Val | Ala |
| Val | Met 130 | Asn | His | Leu | Gln | Glu 135 | Ala | Ala | Leu | Asn | His 140 | Ala | Lys | Ser | Val |
| Gly 145 | Ile | Leu | Gly | Asp | Gly 150 | Phe | Gly | Thr | Thr | Leu 155 | Glu | Met | Ser | Lys | Arg 160 |
| Asp | Leu | Ile | Trp | Val 165 | Val | Lys | Arg | Thr | His 170 | Val | Ala | Val | Glu | Arg 175 | Tyr |
| Pro | Ala | Trp | Gly 180 | Asp | Thr | Val | Glu | Val 185 | Glu | Cys | Trp | Val | Gly 190 | Ala | Ser |
| Gly | Asn | Asn 195 | Gly | Arg | Arg | His | Asp 200 | Phe | Leu | Val | Arg | Asp 205 | Cys | Lys | Thr |
| Gly | Glu 210 | Ile | Leu | Thr | Arg | Cys 215 | Thr | Ser | Leu | Ser | Val 220 | Met | Met | Asn | Thr |
| Arg 225 | Thr | Arg | Arg | Leu | Ser 230 | Lys | Ile | Pro | Glu | Glu 235 | Val | Arg | Gly | Glu | Ile 240 |
| Gly | Pro | Ala | Phe | Ile 245 | Asp | Asn | Val | Ala | Val 250 | Lys | Asp | Glu | Glu | Ile 255 | Lys |
| Lys | Pro | Gln | Lys 260 | Leu | Asn | Asp | Ser | Thr 265 | Ala | Asp | Tyr | Ile | Gln 270 | Gly | Gly |
| Leu | Thr | Pro 275 | Arg | Trp | Asn | Asp | Leu 280 | Asp | Ile | Asn | Gln | His 285 | Val | Asn | Asn |
| Ile | Lys 290 | Tyr | Val | Asp | Trp | Ile 295 | Leu | Glu | Thr | Val | Pro 300 | Asp | Ser | Ile | Phe |
| Glu 305 | Ser | His | His | Ile | Ser 310 | Ser | Phe | Thr | Ile | Glu 315 | Tyr | Arg | Arg | Glu | Cys 320 |
| Thr | Met | Asp | Ser | Val 325 | Leu | Gln | Ser | Leu | Thr 330 | Thr | Val | Ser | Gly | Gly 335 | Ser |
| Ser | Glu | Ala | Gly 340 | Leu | Val | Cys | Glu | His 345 | Leu | Leu | Gln | Leu | Glu 350 | Gly | Gly |
| Ser | Glu | Val 355 | Leu | Arg | Ala | Lys | Thr 360 | Glu | Trp | Arg | Pro | Lys 365 | Leu | Thr | Asp |
| Ser | Phe 370 | Arg | Gly | Ile | Ser | Val 375 | Ile | Pro | Ala | Glu | Ser 380 | Ser | Val | | |

( 2 ) INFORMATION FOR SEQ ID NO: 31:

( i ) SEQUENCE CHARACTERISTICS:
        ( A ) LENGTH: 383 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 31:

| | | | | | | | | | | | | | | | |
|---|---|---|---|---|---|---|---|---|---|---|---|---|---|---|---|
| Met 1 | Val | Thr | Thr | Ser 5 | Leu | Ala | Ser | Ala | Phe 10 | Phe | Ser | Met | Lys | Ala 15 | Val |
| Met | Leu | Ala | Pro 20 | Asp | Gly | Ser | Gly | Ile 25 | Lys | Pro | Arg | Ser | Ser 30 | Gly | Leu |
| Gln | Val | Arg 35 | Ala | Gly | Lys | Glu | Gln 40 | Asn | Ser | Cys | Lys | Met 45 | Ile | Asn | Gly |

```
Thr  Lys  Val  Lys  Asp  Thr  Glu  Gly  Leu  Lys  Gly  Arg  Ser  Thr  Leu  His
     50             55                  60

Gly  Trp  Ser  Met  Pro  Leu  Glu  Leu  Ile  Thr  Thr  Ile  Phe  Ser  Ala  Ala
65                  70                      75                            80

Glu  Lys  Gln  Trp  Thr  Asn  Leu  Val  Ser  Lys  Pro  Pro  Gln  Leu  Leu  Asp
               85                       90                       95

Asp  His  Leu  Gly  Leu  His  Gly  Leu  Val  Phe  Arg  Arg  Thr  Phe  Ala  Ile
               100                 105                      110

Arg  Cys  Ser  Glu  Val  Gly  Pro  Asp  Arg  Ser  Thr  Ser  Ile  Val  Ala  Val
               115                 120                      125

Met  Asn  Tyr  Leu  Gln  Glu  Ala  Ala  Cys  Asn  His  Ala  Glu  Ser  Leu  Gly
     130                 135                       140

Leu  Leu  Gly  Asp  Gly  Phe  Gly  Glu  Thr  Leu  Glu  Met  Ser  Arg  Arg  Asp
145                 150                      155                           160

Leu  Ile  Trp  Val  Val  Arg  Arg  Thr  His  Val  Val  Gly  Thr  Tyr  Pro
               165                      170                      175

Ala  Trp  Gly  Asp  Thr  Val  Glu  Val  Glu  Ala  Trp  Ile  Gly  Ala  Ala  Gly
               180                 185                           190

Asn  Ile  Gly  Met  Arg  Arg  His  Phe  Leu  Val  Arg  Asp  Cys  Lys  Thr  Gly
               195                 200                      205

His  Ile  Leu  Ala  Arg  Cys  Thr  Ser  Val  Ser  Val  Met  Met  Asn  Met  Arg
     210                 215                      220

Thr  Arg  Arg  Leu  Ser  Lys  Ile  Pro  Gln  Glu  Val  Arg  Gly  Glu  Ile  Asp
225                      230                 235                           240

Pro  Leu  Phe  Ile  Glu  Lys  Phe  Ala  Val  Lys  Glu  Gly  Glu  Ile  Lys  Lys
               245                      250                      255

Leu  Gln  Lys  Phe  Asn  Asp  Ser  Thr  Ala  Asp  Tyr  Ile  Gln  Gly  Gly  Trp
               260                      265                 270

Thr  Pro  Arg  Trp  Asn  Asp  Leu  Asp  Val  Asn  Gln  His  Val  Asn  Asn  Ile
          275                 280                           285

Lys  Tyr  Val  Gly  Trp  Ile  Phe  Lys  Ser  Val  Pro  Asp  Ser  Ile  Tyr  Glu
     290                 295                      300

Asn  His  His  Leu  Ser  Ser  Ile  Thr  Leu  Glu  Tyr  Arg  Arg  Glu  Cys  Thr
305                      310                      315                      320

Arg  Gly  Arg  Ala  Leu  Gln  Ser  Leu  Thr  Thr  Val  Cys  Gly  Gly  Ser  Ser
               325                      330                      335

Glu  Ala  Gly  Ile  Ile  Cys  Glu  His  Leu  Leu  Gln  Leu  Glu  Asp  Gly  Ser
               340                      345                      350

Glu  Val  Leu  Arg  Gly  Arg  Thr  Asp  Trp  Arg  Pro  Lys  Arg  Thr  Asp  Ser
          355                 360                      365

Phe  Glu  Gly  Ile  Ser  Glu  Arg  Phe  Pro  Gln  Gln  Glu  Pro  His  Asn
370                      375                 380
```

( 2 ) INFORMATION FOR SEQ ID NO: 32:

( i ) SEQUENCE CHARACTERISTICS:
        ( A ) LENGTH: 362 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 32:

```
Met  Leu  Lys  Leu  Ser  Cys  Asn  Ala  Thr  Asp  Lys  Leu  Gln  Thr  Leu  Phe
1               5                       10                      15

Ser  His  Ser  His  Gln  Pro  Asp  Pro  Ala  His  Arg  Arg  Thr  Val  Ser  Ser
```

|   |   |   |   |   | 20 |   |   |   |   | 25 |   |   |   |   | 30 |   |   |
|---|---|---|---|---|---|---|---|---|---|---|---|---|---|---|---|---|---|
| Val | Ser | Cys<br>35 | Ser | His | Leu | Arg | Lys<br>40 | Pro | Val | Leu | Asp | Pro<br>45 | Leu | Arg | Ala |
| Ile | Val<br>50 | Ser | Ala | Asp | Gln | Gly<br>55 | Ser | Val | Ile | Arg | Ala<br>60 | Glu | Gln | Gly | Leu |
| Gly<br>65 | Ser | Leu | Ala | Asp | Gln<br>70 | Leu | Arg | Leu | Gly | Ser<br>75 | Leu | Thr | Glu | Asp | Gly<br>80 |
| Leu | Ser | Tyr | Lys | Glu<br>85 | Lys | Phe | Ile | Val | Arg<br>90 | Ser | Tyr | Glu | Val | Gly<br>95 | Ser |
| Asn | Lys | Thr | Ala<br>100 | Thr | Val | Glu | Thr<br>105 | Val | Ala | Asn | Leu | Leu | Gln<br>110 | Glu | Val |
| Gly | Cys | Asn<br>115 | His | Ala | Gln | Ser | Val<br>120 | Gly | Phe | Ser | Thr | Asp<br>125 | Gly | Phe | Ala |
| Thr | Thr<br>130 | Pro | Thr | Met | Arg | Lys<br>135 | Leu | His | Leu | Ile | Trp<br>140 | Val | Thr | Ala | Arg |
| Met<br>145 | His | Ile | Glu | Ile | Tyr<br>150 | Lys | Tyr | Pro | Ala | Trp<br>155 | Gly | Asp | Val | Val | Glu<br>160 |
| Ile | Glu | Thr | Trp | Cys<br>165 | Gln | Ser | Glu | Gly | Arg<br>170 | Ile | Gly | Thr | Arg | Arg<br>175 | Asp |
| Trp | Ile | Leu | Lys<br>180 | Asp | Val | Ala | Thr | Gly<br>185 | Glu | Val | Thr | Gly | Arg<br>190 | Ala | Thr |
| Ser | Lys | Trp<br>195 | Val | Met | Met | Asn | Gln<br>200 | Asp | Thr | Arg | Arg | Leu<br>205 | Gln | Lys | Val |
| Ser | Asp<br>210 | Asp | Val | Arg | Asp | Glu<br>215 | Tyr | Leu | Val | Phe | Cys<br>220 | Pro | Lys | Glu | Leu |
| Arg<br>225 | Leu | Ala | Phe | Pro | Glu<br>230 | Glu | Asn | Asn | Arg | Ser<br>235 | Leu | Lys | Lys | Ile | Pro<br>240 |
| Lys | Leu | Glu | Asp | Pro<br>245 | Ala | Gln | Tyr | Ser | Met<br>250 | Ile | Gly | Leu | Lys | Pro<br>255 | Arg |
| Arg | Ala | Asp | Leu<br>260 | Asp | Met | Asn | Gln | His<br>265 | Val | Asn | Asn | Val | Thr<br>270 | Tyr | Ile |
| Gly | Trp | Val<br>275 | Leu | Glu | Ser | Ile | Pro<br>280 | Gln | Glu | Ile | Val | Asp<br>285 | Thr | His | Glu |
| Leu | Gln<br>290 | Val | Ile | Thr | Leu | Asp<br>295 | Tyr | Arg | Arg | Glu | Cys<br>300 | Gln | Gln | Asp | Asp |
| Val<br>305 | Val | Asp | Ser | Leu | Thr<br>310 | Thr | Thr | Thr | Ser | Glu<br>315 | Ile | Gly | Gly | Thr | Asn<br>320 |
| Gly | Ser | Ala | Ser | Ser<br>325 | Gly | Thr | Gln | Gly | Gln<br>330 | Asn | Asp | Ser | Gln | Phe<br>335 | Leu |
| His | Leu | Leu | Arg<br>340 | Leu | Ser | Gly | Asp | Gly<br>345 | Gln | Glu | Ile | Asn | Arg<br>350 | Gly | Thr |
| Thr | Leu | Trp<br>355 | Arg | Lys | Lys | Pro | Ser<br>360 | Asn | Leu |   |   |   |   |   |   |

( 2 ) INFORMATION FOR SEQ ID NO: 33:

( i ) SEQUENCE CHARACTERISTICS:
        ( A ) LENGTH: 416 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 33:

| Met<br>1 | Ala | Ser | Thr | Ala<br>5 | Ala | Thr | Ala | Ala | Phe<br>10 | Phe | Pro | Val | Ser | Ser<br>15 | Ser |

```
Thr  Asp  Ser  Val  Ala  Lys  Pro  Lys  Asn  Ile  Gly  Ser  Ala  Gly  Leu  Gly
               20                  25                       30

Gly  Leu  Lys  Ser  Lys  Ser  Ser  Ser  Gly  Arg  Leu  Gln  Val  Lys  Ala  Thr
          35                       40                       45

Ala  Gln  Ala  Pro  Ser  Lys  Ile  Asn  Gly  Thr  Ser  Val  Gly  Leu  Thr  Lys
     50                       55                       60

Pro  Val  Glu  Gly  Leu  Lys  Asn  Glu  Asp  Asp  Met  Pro  Ser  Pro  Pro  Pro
65                       70                  75                            80

Arg  Thr  Phe  Ile  Asn  Gln  Leu  Pro  Asp  Trp  Ser  Met  Leu  Leu  Ala  Ala
                    85                  90                            95

Ile  Thr  Thr  Ile  Phe  Leu  Ala  Ala  Glu  Lys  Gln  Trp  Met  Met  Leu  Asp
               100                 105                      110

Trp  Lys  Pro  Arg  Arg  Ser  Asp  Met  Leu  Ile  Asp  Pro  Phe  Gly  Ile  Gly
          115                 120                      125

Arg  Ile  Val  Gln  Asp  Gly  Leu  Ile  Phe  Arg  Gln  Asn  Phe  Ser  Ile  Arg
     130                 135                      140

Ser  Tyr  Glu  Ile  Gly  Ala  Asp  Arg  Thr  Ala  Ser  Ile  Glu  Thr  Leu  Met
145                      150                 155                           160

Asn  His  Leu  Gln  Glu  Thr  Ala  Leu  Asn  His  Val  Lys  Thr  Ala  Gly  Leu
                    165                      170                      175

Leu  Gly  Asp  Gly  Phe  Gly  Ala  Thr  Pro  Glu  Met  Cys  Lys  Lys  Asn  Leu
               180                      185                      190

Ile  Trp  Val  Val  Thr  Arg  Met  Gln  Val  Val  Val  Asp  Arg  Tyr  Pro  Thr
          195                      200                 205

Trp  Gly  Asp  Val  Val  Glu  Val  Asp  Thr  Trp  Val  Ser  Ala  Ser  Gly  Lys
          210                      215                 220

Asn  Gly  Met  Arg  Arg  Asp  Trp  Leu  Val  Arg  Asp  Gly  Gln  Thr  Gly  Glu
225                           230                 235                      240

Thr  Leu  Thr  Arg  Ala  Ser  Ser  Val  Trp  Val  Thr  Met  Asn  Lys  Gln  Thr
               245                      250                           255

Arg  Arg  Leu  Ser  Lys  Ile  Pro  Asp  Glu  Val  Arg  Gly  Glu  Ile  Glu  Pro
               260                 265                      270

Tyr  Phe  Val  Asn  Ser  Asp  Pro  Val  Val  Asp  Glu  Asp  Ser  Arg  Lys  Leu
               275                 280                      285

Pro  Lys  Leu  Asp  Asp  Asn  Thr  Ala  Asp  Tyr  Val  Cys  Arg  Gly  Leu  Thr
     290                      295                      300

Pro  Arg  Trp  Ser  Asp  Leu  Asp  Val  Asn  Gln  His  Val  Asn  Asn  Val  Lys
305                      310                 315                           320

Tyr  Ile  Gly  Trp  Ile  Leu  Glu  Ser  Ala  Pro  Gln  Ala  Ile  Leu  Glu  Ser
                    325                      330                 335

His  Glu  Leu  Ala  Ser  Met  Thr  Leu  Glu  Tyr  Arg  Arg  Glu  Cys  Gly  Lys
               340                      345                 350

Asp  Ser  Val  Leu  Gln  Ser  Leu  Thr  Ala  Val  Ser  Ser  Ser  Asp  Asn  Gly
          355                      360                 365

Asn  Leu  Ala  Leu  Ser  Gly  Gly  Ala  Glu  Cys  Gln  His  Met  Leu  Arg  His
     370                 375                      380

Glu  Asp  Gly  Pro  Glu  Ile  Val  Arg  Gly  Arg  Thr  Glu  Trp  Arg  Pro  Lys
385                      390                 395                           400

Tyr  Ala  Asn  Asn  Leu  Gly  Asn  Val  Gly  Glu  Val  Pro  Val  Gly  Ser  Ala
                    405                      410                      415
```

PLANT ACYL-ACP THIOESTERASE SEQUENCES

This application is a continuation-in-part of application PCT/US94/13131 filed Nov. 10, 1994, a continuation-in-part of application U.S. Ser. No. 08/261,695 filed Jun. 16, 1994, now abandoned, and a continuation-in-part of application U.S. Ser. No. 08/152,004 filed Nov. 10, 1993, now abandoned.

FIELD OF THE INVENTION

This invention relates to the application of genetic engineering techniques to plants. More specifically, the invention relates to plant acyl-ACP thioesterase sequences and methods for the use of such sequences.

BACKGROUND

Fatty acids are organic acids having a hydrocarbon chain of from about 4 to 24 carbons. Many different kinds of fatty acids are known which differ from each other in chain length, and in the presence, number and position of double bonds. In cells, fatty acids typically exist in covalently bound forms, the carboxyl portion being referred to as a fatty acyl group. The chain length and degree of saturation of these molecules is often depicted by the formula CX:Y, where "X" indicates number of carbons and "Y" indicates number of double bonds.

Fatty acyl groups are major components of many lipids, and their long, non-polar hydrocarbon chain is responsible for the water-insoluble nature of these lipid molecules. The type of covalent linkage of the fatty acyl group to other factors can vary. For example, in biosynthetic reactions they may be covalently bound via a thioester linkage to an acyl carrier protein (ACP) or to CoenzymeA (CoA), depending on the particular enzymatic reaction. In waxes, fatty acyl groups are linked to fatty alcohols via an ester linkage, and triacylglycerols have three fatty acyl groups linked to a glycerol molecule via an ester linkage.

The fatty acid composition of an oil determines its physical and chemical properties, and thus its uses. Plants, especially plant species which synthesize large amounts of oils in plant seeds, are an important source of oils both for edible and industrial uses.

The fatty acid composition of major oilseeds, ordered here by palmitate content, is shown in Table I. With the exception of laurate (C12:0) sources of coconut endosperm and palm kernel, the common edible oils all basically consist of 16:0, 18:0, 18:1 (oleate), 18:2 (linoleate), and 18:3 (linolenate).

TABLE I

| | 12:0 | 14:0 | 16:0 | 18:0 | 18:1 | 18:2 | 18:3 | 20:1 | 22:1 |
|---|---|---|---|---|---|---|---|---|---|
| rape (HEAR) | | | 3 | 0.8 | 9.9 | 13.5 | 9.8 | 6.8 | 53.6 |
| rape (LEAR) | | | 4.9 | 1.4 | 56.4 | 24.2 | 10.5 | | |
| sunflower | | 0.1 | 5.8 | 5.2 | 16 | 71.5 | 0.2 | | |
| peanut | | | 6.7 | 4.3 | 71.4 | 11.1 | 6.5 | | |
| safflower | | | 7.6 | 2 | 10.8 | 79.6 | | | |
| coconut | 40.2 | 15.5 | 7.6 | 2.4 | 5.2 | 1.2 | | | |
| oil palm kernel | 50.9 | 18.4 | 8.7 | 1.9 | 14.6 | 1.2 | | | |
| soybean | | | 15.3 | 3.8 | 20.7 | 55.8 | 9.4 | | |
| cotton | | 1 | 23.4 | 2.5 | 17.9 | 54.2 | | | |
| oil palm mesocarp | 0.1 | 1.2 | 46.8 | 3.8 | 37.6 | | | | |

Plant breeders have successfully modified the yield and fatty acid composition of various plant seed oils through programs of introducing desired traits by plant crosses and selection of progeny carrying the desired trait forward. Application of this technique thus is limited to traits which are found within the same plant species. Alternatively, exposure to mutagenic agents can also introduce traits which may produce changes in the composition of a plant seed oil. However, it is important to note that Fatty Acid Synthesis (FAS) occurs in leaf (chloroplasts) and seed tissue (proplastids). Thus, although a mutagenesis approach can sometimes result in a desired modification of the composition of a plant seed oil, it is difficult to effect a change which will not alter FAS in other tissues of the plant.

A wide range of novel vegetable oils compositions and/or improved means to obtain or manipulate fatty acid compositions, from biosynthetic or natural plant sources, are needed for a variety of intended uses. Plant breeding, even with mutagenesis, cannot meet this need and provide for the introduction of any oil traits which are outside of the target plant's gene pool.

Higher plants appear to synthesize fatty acids via a common metabolic pathway in plant plastid organelles (i.e., chloroplasts, proplastids, or other related organelles) as part of the FAS complex. (By fatty acid is meant free fatty acids and acyl-fatty acid groups.) Outside of plastid organelles, fatty acids are incorporated into triacylglycerols (triglycerides) and used in plant membranes and in neutral lipids. In developing seeds, where oils are produced and stored as sources of energy for future use, FAS occurs in proplastids.

The production of fatty acids begins in the plastid with the reaction between acetyl-CoA and malonyl-ACP to produce butyryl-ACP catalyzed by the enzyme, β-ketoacyl-ACP synthase III. Elongation of acetyl-ACP to 16- and 18- carbon fatty acids involves the cyclical action of the following sequence of reactions: condensation with a two-carbon unit from malonyl-ACP to form a β-ketoacyl-ACP (β-ketoacyl-ACP synthase), reduction of the keto-function to an alcohol (β-ketoacyl-ACP reductase), dehydration to form an enoyl-ACP (β-hydroxyacyl-ACP dehydrase), and finally reduction of the enoyl-ACP to form the elongated saturated acyl-ACP (enoyl-ACP reductase). β-ketoacyl-ACP synthase I, catalyzes elongation up to palmitoyl-ACP (C16:0), whereas β-ketoacyl-ACP synthase II catalyzes the final elongation to stearoyl-ACP (C18:0). The longest chain fatty acids produced by the FAS are typically 18 carbons long. Monounsaturated fatty acids are also produced in the plastid through the action of a desaturase enzyme.

A further fatty acid biochemical step occuring in the plastid is the desaturation of stearoyl-ACP (C18:0) to form oleoyl-ACP (C18:1) in a reaction often catalyzed by a Δ-9 desaturase, also often referred to as a "stearoyl-ACP desaturase" because of its high activity toward stearate the 18 carbon acyl-ACP. The desaturase enzyme functions to add a double bond at the ninth carbon in accordance with the following reaction (I):

Stearoyl-ACP+ferredoxin (II)+$O_2$+2H$^+$→oleoyl-ACP+ferredoxin (III)+2$H_2O$.

Carbon-chain elongation in the plastids can be terminated by transfer of the acyl group to glycerol 3-phosphate, with the resulting glycerolipid retained in the plastidial, "prokaryotic", lipid biosynthesis pathway. Alternatively, specific thioesterases can intercept the prokaryotic pathway by hydrolyzing the newly produced acyl-ACPs into free fatty acids and ACP. Subsequently, the free fatty acids exit the plastids and are incorporated into the "eukaryotic" lipid biosynthesis pathway in the endoplasmic reticulum which is responsible for the formation of phospholipids, triglycerides and other neutral lipids.

Previously, plant acyl-ACP thioesterases specific for 18:1-ACP thioesterases were known, and were termed "long-chain"- or "oleoyl"-ACP thioesterases. Encoded by nuclear genes, 18:1-ACP thioesterases are synthesized as preproteins in the cytoplasm and subsequently imported into the plastids. Sequences have been obtained from several angiosperm families and, aside from high variability in the transit peptides, they are very similar to each other. Recently, Pollard, et al., (Arch. of Biochem. and Biophys.(1991) 284:1–7) identified a medium-chain acyl-ACP thioesterase activity in developing oilseeds of California bay, Umbellularia californica. This activity appears only when the developing cotyledons become committed to the near-exclusive production of triglycerides with lauroyl (12:0) and caproyl (10:0) fatty acids. This work presented the first evidence for a mechanism for medium-chain fatty acid synthesis in plants. The bay thioesterase was subsequently purified by Davies et al., (Arch. Biochem. Biophys. (1991) 290:37–45) which allowed the cloning of a corresponding cDNA which has been used to obtain related clones and to modify the triglyceride composition of plants (Voelker et al. (1992) Science 257:72–74; WO 91/16421 and WO 92/20236).

Following transport of free fatty acids to the endoplasmic reticulum, subsequent sequential steps for triglyceride production can occur. For example, polyunsaturated fatty acyl groups such as linoleoyl and α-linolenoyl, are produced as the result of sequential desaturation of oleoyl acyl groups by the action of membrane-bound enzymes. Difficulties in the solubilization of such membrane-bound enzymes has hindered efforts to characterize these enzymes. Additional double bonds are added at the twelve position carbon and thereafter, if added, at the 15 position carbon through the action of Δ-12 desaturase and Δ-15 desaturase, respectively. These "desaturases" thus create mono- or polyunsaturated fatty acids respectively.

Triglycerides are then formed by action of the 1-, 2-, and 3- acyl-ACP transferase enzymes glycerol-3-phosphate acyltransferase, lysophosphatidic acid acyltransferase and diacylglycerol acyltransferase. The fatty acid composition of a plant cell is a reflection of the free fatty acid pool and the fatty acids (fatty acyl groups) incorporated into triglycerides as a result of the acyltransferase activities. Thus, in a triglyceride molecule, represented as

Formula (I)

where X, Y, and Z each represents a fatty acyl group which may be the same or different from one another. Various combinations of fatty acyl groups in the different positions in the triglyceride will alter the properties of triglyceride. For example, if the fatty acyl groups are mostly saturated fatty acids, then the triglyceride will be solid at room temperature. In general, however, vegetable oils tend to be mixtures of different triglycerides. The triglyceride oil properties are therefore a result of the combination of triglycerides which make up the oil, which are in turn influenced by their respective fatty acyl compositions.

For example, cocoa-butter has certain desirable qualities (mouth feel, sharp melting point, etc.) which are a function of its triglyceride composition. Cocoa-butter contains approximately 24.4% palmitate (16:0), 34.5% stearate (18:0), 39.1% oleate (18:1) and 2% linoleate (18:2). Thus, in cocoa butter, palmitoyl-oleoyl-stearoyl (POS) (i.e., X, Y and Z, respectively, in Formula I) comprises almost 50% of triglyceride composition, with stearate-oleate-stearate (SOS) and palmitoyl-oleoyl-palmitoyl (POP) comprising the major portion of the balance at 39% and 16%, respectively, of the triglyceride composition. Other novel oils compositions of interest might include trierucin (three erucic) or a triglyceride with medium chain fatty acids in each position of the triglyceride molecule.

Of particular interest are triglyceride molecules in which palmitoyl is esterified at the X and Z positions of Formula I and a C18 fatty acyl group is at Y. Vegetable oils rich in such PXP (palmitoyl-C18-palmitoyl) molecules have certain desirable qualities in shortening applications, and will find use as additives to solid shortenings to enhance functional effects for retail consumers or industrial food formulators. For example, dipalmitate may be added to shortenings for baking and frying applications to provide proper crystallization of total fat, for example for cake baking applications. In addition, dipalmitate has less effect on melting properties than other possible fat additives, such as distearate, and can be used to produce shortenings having greater "spreadability" within the baking mass. This property of dipalmitate-containing shortenings is of particular interest where the shortening is used as a layering ingredient, for example in pie crusts or sweet goods.

In addition, vegetable oils rich in saturated fatty acid content, such as from palmitate and or stearate fatty acids, tend to be solid at room temperature. Such vegetable fats can be used directly in shortenings, margarine and other food "spread" products, without the need for chemical hydrogenation. Hydrogenation is a process to convert unsaturated fatty acids in liquid oils to a saturated form which in turn converts the oil into a solid fat useful in margarine and shortening applications. The cost and any other factors associated with chemical hydrogenation can be avoided if the vegetable oil is engineered to be palmitate and/or stearate rich in the plant seed. Of particular interest in this regard are vegetable oils in which palmitate and stearate are excluded from the sn-2 position of the triglyceride.

Furthermore, fatty acids derivatized from vegetable oils containing significant proportions (i.e. 40%) of palmitoyl and stearoyl fatty acyl groups find uses in food emulsification applications due to the desirable softening properties of a palmitate rich fraction that may be obtained from such vegetable oils.

Thus, a variety of plant oils modifications are desired, including alternative crop sources for certain oils products and/or means to provide novel fatty acid compositions for plant seed.

DESCRIPTION OF THE FIGURES

FIGS. 1A–1E. The nucleic acid sequence (SEQ ID NO:1) and translated amino acid sequence (SEQ ID NO:22) of a mango Class I acyl-ACP thioesterase cDNA clone are provided in FIGS. 1A through 1E.

FIGS. 2A–2E. The nucleic acid sequence (SEQ ID NO:2) and translated amino acid sequence (SEQ ID NO:23) of a mango Class II acyl-ACP thioesterase cDNA clone (MANI-2) are provided in FIGS. 2A through 2E.

FIGS. 3A–3D. DNA sequence (SEQ ID NO:3) and translated amino acid sequence (SEQ ID NO:24) of a partial Class II acyl-ACP thioesterase cDNA clone, 8-2, from leek are provided in FIGS. 3A through 3D.

FIGS. 4A–4E. DNA sequence (SEQ ID NO:4) and translated amino acid sequence (SEQ ID NO:25) of a full length Class II acyl-ACP thioesterase cDNA clone, 9-1, from leek are provided in FIGS 4A through 4E.

FIGS. 5A–5E. The nucleic acid sequence (SEQ ID NO:5) and translated amino acid sequence (SEQ ID NO:26) of a bay Class II C12 preferring acyl-ACP thioesterase cDNA clone are provided in FIGS 5A through 5E.

FIG. 6A–6E. The nucleic acid sequence (SEQ ID NO:6) and translated amino acid sequence (SEQ ID NO:27) of a full length Class II *Cuphea hookeriana* thioesterase (CUPH-2) cDNA clone, CMT7, is shown in FIGS 6A through 6E.

FIGS. 7A–7F. The nucleic acid sequence (SEQ ID NO:7) and translated amino acid sequence (SEQ ID NO:28) of a full length Class II *Cuphea hookeriana* thioesterase (CUPH-1) cDNA clone, CMT9, is shown in FIGS 7A through 7F.

FIGS. 8A–8D. The nucleic acid sequence (SEQ ID NO:8) and translated amino acid sequence (SEQ ID NO:29) of an elm C10:0-ACP thioesterase (Class II) partial cDNA clone are provided in FIGS 8A through 8D.

FIGS. 9A–9F. Nucleic acid sequence (SEQ ID NO:9) and translated amino acid sequences (SEQ ID NO:30) of a camphor PCR-generated thioesterase encoding sequence is presented in FIGS 9A through 9F.

FIGS. 10A–10E. Nucleic acid sequence (SEQ ID NO:10) and translated amino acid sequence (SEQ ID NO:31) of a bay thioesterase clone, Bay D, which represents a second class of bay thioesterase genes, is presented in FIGS 10A through 10E.

FIGS. 11A–11D. Nucleic acid sequence (SEQ ID NO:11) and translated amino acid sequence (SEQ ID NO:32) of a *Brassica campestris* long-chain acyl ACP thioesterase clone is shown in FIGS 11A through 11D.

FIGS. 12A–12F. Nucleic acid sequence (SEQ ID NO:12) and translated amino acid sequence (SEQ ID NO:33) of a second mango Class II clone (M4-23) are provided in FIGS 12A through 12F.

FIG. 13. Fatty acid analysis of *Brassica napus* 212/86 pooled seed samples from plants transformed with C16:0-ACP thioesterase CUPH-1 (Ch FatB1) construct pCGN4800.

FIG. 14. Fatty acid analysis of *Brassica napus* 212/86 pooled seed samples from plants transformed with elm Class II acyl-ACP thioesterase construct pCGN4803.

The FIG. 15. Fatty acid analysis of *Brassica napus* pooled seed samples from plants transformed with mango acyl-ACP thioesterase construct pCGN5228.

SUMMARY OF THE INVENTION

This invention relates to plant thioesterases, specifically plant acyl-ACP thioesterases capable of producing C16:0 (palmitate) fatty acids in transgenic plant seeds. Such acyl-ACP thioesterases are referred to herein as palmitoyl-ACP thioesterases, but may also demonstrate activity on other acyl-ACPs of various chain lengths.

By this invention, DNA constructs useful for the expression of a plant palmitoyl-ACP thioesterase in a plant seed cell are described. Such constructs will contain a DNA sequence encoding a plant thioesterase having palmitoyl-ACP hydrolysis activity under the control of regulatory elements capable of preferentially directing expression in seed tissue, as compared with other plant tissues, when such a construct is expressed in a transgenic plant. At least one element of the DNA construct will be heterologous to at least one other of the elements, or when found in a plant cell, at least one element will be heterologous to the plant cell.

In a different embodiment, host plant cells containing a first DNA construct capable of expressing a plant palmitoyl-ACP thioesterase, and a second DNA construct capable of expressing an anti-sense stearoyl-acyl ACP desaturase sequence are desired. Such a first DNA construct will contain a DNA sequence encoding the plant palmitoyl-ACP thioesterase of interest under the control of regulatory elements capable of preferentially directing the expression of the plant thioesterase in seed tissue as compared with other plant tissues when such a construct is expressed in a transgenic plant. The second DNA construct will contain a DNA sequence encoding a plant stearoyl-acyl ACP desaturase element positioned in an anti-sense orientation under the control of regulatory elements capable of directing the transcription of the plant stearoyl-acyl ACP desaturase anti-sense sequence in the plant host seed cell.

In yet a different aspect, this invention relates to methods of using a DNA sequence encoding a plant palmitoyl-ACP thioesterase for the modification of the proportion of free fatty acids produced in a plant seed cell. In a like fashion, this invention relates to methods of using such plant palmitoyl-ACP thioesterase encoding sequences to modify the composition of triglycerides, i.e., plant oils, produced by a plant seed to contain increased levels of C16 fatty acyl groups. Plants and plant parts, particularly seeds and oils extracted from such seeds, having such a modified fatty acid composition are contemplated herein.

Plant palmitoyl-ACP thioesterase sequences exemplified herein include those obtainable from leek, mango, *Cuphea hookeriana* and elm. These exemplified thioesterases may be used to obtain other plant palmitoyl-ACP thioesterases of this invention.

DETAILED DESCRIPTION OF THE INVENTION

By this invention, a mechanism for the increased accumulation of palmitate (C16:0) in plants is demonstrated. Namely, plant acyl-ACP thioesterases having activity toward C16:0-ACP substrates are provided and demonstrated to lead to the production of increased levels of palmitate when expressed in seeds of transgenic plants.

Analysis of the encoding sequences and translated amino acid sequences of a number of plant acyl-ACP thioesterases has demonstrated the existence of two evolutionary classes of plant acyl-ACP thioesterases which we have designated as "Class I" or "FatA" (for fatty acyl transferase type A) and "Class II" (or "FatB"). These classes are not a simple reflection of phylogenetic relationships of the various plants from which the thioesterase encoding sequences were obtained. For example, a *Cuphea hookeriana* FatA clone (clone CLT7 in FIG. 10 of WO 94/10288) is closely related to safflower FatA clones (sequences provided in FIG. 4 of WO 92/20236). In contrast, a *Cuphea hookeriana* FatB clone (FIG. 7 CUPH-1 clone) is equally distant in evolutionary relationship from the *Cuphea hookeriana* FatA clone and the safflower FatA clone.

Class I thioesterases have been found in mango (FIG. 1), safflower, *Brassica campestris* and *Cuphea hookeriana*, which sequences are provided in U.S. Ser. No. 07/949,102, filed Sep. 21, 1992, now pending, and in WO 92/20236 and WO 94/10288. Class II thioesterases have been discovered in California bay (FIGS. 5 & 10), elm (FIG. 8), *Cuphea*

*hookeriana* (FIGS. 6 & 7), and camphor (FIG. 9). Presently, all known plant medium-chain preferring acyl-ACP thioesterases are of the Class II type, and all known 18:1-ACP thioesterases are of the Class I type.

Surprisingly, the *Cuphea hookeriana* Class II clone represented in FIG. 7 was discovered to have preferential activity on palmitoyl-ACP fatty acids and to be capable, when expressed in seeds of transgenic plants, of altering the lipid biosynthesis pathway to increase the content of C16:0 fatty acyl groups incorporated into triglycerides. This discovery was unexpected as this Cuphea species accumulates predominantly C8 and C10 fatty acyl groups in its seed storage lipids. The Cuphea C16:0-ACP thioesterase was demonstrated to be expressed in various plant tissues, including leaves, stems and roots, whereas a different Cuphea Class II thioesterase (CUPH-2; FIG. 6), which was preferentially active on C8:0 and C10:0 substrates, was expressed preferentially in seed tissues.

A Class II acyl-ACP thioesterase clone was also discovered in an Arabidopsis silique cDNA library based on homology of a randomly cloned cDNA fragment to the bay C12:0-ACP thioesterase clone. A full length cDNA clone encoding the Arabidopsis thioesterase was obtained and demonstrated to encode a thioesterase having activity on a range of acyl-ACP substrates, including 16:0-ACP. Thus, it is now seen that Class II type fatty acyl-ACP thioesterase sequences may be found in plant species not known to accumulate medium chain length fatty acids. Such acyl-ACP thioesterase sequences may be examined, for example by expression in *E. coli* or plant cells, to identify those clones having significant or preferential activity on C16:0-ACP substrates.

In this application, cDNA sequence of the *Cuphea hookeriana* palmitoyl-ACP thioesterase (FIG. 7) is provided, as well as additional C16:0-ACP thioesterase sequences from mango (FIGS. 2 and 12), and leek (FIGS. 3 & 4). In addition, DNA sequence of an elm acyl-ACP thioesterase clone is provided (FIG. 8). Expression of the elm clone in transgenic plant seeds results in an increased proportion of C16:0 fatty acyl groups in the triglycerides, as well as a smaller increase in the proportion of C14:0 fatty acyl groups. All of these acyl-ACP thioesterase sequences, which may be used to increase palmitoyl content of transgenic plant seed oil, show significant sequence identity with other Class II plant thioesterase proteins.

Plants having significant presence of C16:0 fatty acids therein are also candidates to obtain naturally-derived palmitoyl-ACP preferring plant thioesterases. However, it is also recognized that other plant sources which do not have a significant presence of palmitate may also be screened as other enzyme sources. As discussed above, it is now believed that proteins demonstrating palmitoyl-ACP thioesterase activity will show a high degree of homology at the DNA and amino acid level, with a particular class of acyl-ACP thioesterases known as "Class II" thioesterases herein. Thus, it is possible to readily screen for additional plant palmitoyl-ACP thioesterases in any plant of interest.

As described in more detail in the following Examples, acyl-ACP thioesterases having activity on C16:0 fatty acids may be expressed in the seeds of target transgenic plants with a resultant increase in the percentage of C16:0 fatty acids in the seed triglycerides. For example, expression of the *Cuphea hookeriana* clone, CUPH-1 (also known as Ch FatB1), in the seeds of transgenic *Brassica napus* plants results in the transformants having C16:0 seed fatty acid contents ranging from 7–26 mol % in pooled seed samples. Analysis of individual seeds from selected transformants revealed C16:0 fatty acid contents of up to 34 mol %. Similarly, expression of a mango Class II clone (MANI-2 sequence shown in FIG. 2) results in transformants having C16:0 seed fatty acid contents ranging from 7–16 mol % in pooled seed samples. Expression of a Class II acyl-ACP thioesterase from elm (FIG. 8) yields transgenic *Brassica napus* plants having C16:0 pooled seed fatty acid contents ranging from 15–32 mol %. In addition, C14:0 fatty acid contents are increased in these seeds to levels ranging from 2–12 mol %, and increases in C10:0 (up to 4 mol %) and C12:0 (up to 1.5 mol %) are also observed. Background levels of C12:0, C14:0, and C16:0 fatty acids in non-transgenic seeds of the transformed variety are approximately 0.02, 0.14 and 6 mol %, respectively. C10:0 fatty acids in non-transgenic seeds are typically determined as being present at less than 1%. (The C10:0 background value in controls may be the result of machine reading of a non-C10:0 peak, as the levels vary from 0 to 1% in analysis of non-transgenic *Brassica napus* plant seed.) TAG positional analysis of the described transgenic plants is expected to reveal the exclusion of the C16:0 fatty acyl groups from the sn-2 position of the seed triglycerides. The seed microsomal 2-acyltransferase in the Brassica plants does not demonstrate efficient activity on substrates other than C18:1-CoA. Furthermore, seed lipids in plants transformed with a bay C12:0-ACP thioesterase contain up to 50 mol % C12:0 fatty acids, but the C12:0 acyl groups were located almost exclusively in the sn-1 and sn-3 positions of the triglycerides (WO 92/20236).

A plant palmitoyl-ACP thioesterase DNA sequence of this invention encodes for amino acids, in the form of a protein, polypeptide or peptide fragment, which amino acids demonstrate the ability to catalyze the production of C16:0 free fatty acid (i.e., palmitate) from palmitoyl-ACP substrates under plant enzyme reactive conditions. By "enzyme reactive conditions" is meant that any necessary conditions are available in an environment (i.e., such factors as temperature, pH, lack of inhibiting substances) which will permit the enzyme to function.

One skilled in the art will readily recognize that antibody preparations, nucleic acid probes (DNA and RNA) and the like may be prepared and used to screen and recover "homologous" or "related" palmitoyl-ACP thioesterases from a variety of plant sources. Typically, nucleic acid probes are labeled to allow detection, preferably with radioactivity although enzymes or other methods may also be used. For immunological screening methods, antibody preparations either monoclonal or polyclonal are utilized. Polyclonal antibodies, although less specific, typically are more useful in gene isolation. For detection, the antibody is labeled using radioactivity or any one of a variety of second antibody/enzyme conjugate systems that are commercially available. Examples of some of the available antibody detection systems are described by Oberfilder (*Focus* (1989) BRL Life Technol., Inc.,11:1–5).

Homologous sequences are found when there is an identity of sequence and may be determined upon comparison of sequence information, nucleic acid or amino acid, or through hybridization reactions between a known thioesterase and a candidate source. Conservative changes, such as Glu/Asp, Val/Ile, Ser/Thr, Arg/Lys and Gln/Asn may also be considered in determining sequence homology. Typically, a lengthy nucleic acid sequence may show as little as 50–60% sequence identity, and more preferably at least about 70% sequence identity, between the target sequence and the given plant thioesterase of interest excluding any deletions which may be present, and still be considered related. Amino acid sequences are considered homologous by as little as 25% sequence identity between the two complete mature proteins. (See generally, Doolittle, R. F., *OF URFS and ORFS* (University Science Books, California, 1986.)

Although all plant thioesterases show approximately 50% sequence identity at the nucleic acid level, between members of Class II the percentage of sequence identity jumps to at least 60%. At the amino acid level, the region corresponding from approximately amino acid 60 through amino acid 150 in the California bay will show a very high degree of conservation between members of Class II thioesterases.

In order to obtain additional palmitoyl-ACP thioesterases, a genomic or other appropriate library prepared from the candidate plant source of interest is probed with conserved sequences from one or more Class II plant thioesterase(s) to identify homologously related sequences. Positive clones are then analyzed by restriction enzyme digestion and/or sequencing. When a genomic library is used, one or more sequences may be identified providing both the coding region, as well as the transcriptional regulatory elements of the thioesterase gene from such plant source. Probes can also be considerably shorter than the entire sequence. Oligonucleotides may be used, for example, but should be at least about 10, preferably at least about 15, more preferably at least 20 nucleotides in length. When shorter length regions are used for comparison, a higher degree of sequence identity is required than for longer sequences. Shorter probes are often particularly useful for polymerase chain reactions (PCR), especially when highly conserved sequences can be identified. (See, Gould, et al., *PNAS USA* (1989) 86:1934–1938.)

When longer nucleic acid fragments are employed (>100 bp) as probes, especially when using complete or large cDNA sequences, one can still screen with moderately high stringencies (for example using 50% formamide at 37° C. with minimal washing) in order to obtain signal from the target sample with 20–50% deviation, i.e., homologous sequences. (For additional information regarding screening techniques see Beltz, et al., *Meth. Enzymology* (1983) 100:266–285).

Again, not only can sequences such as shown in FIGS. 2–10 be used to identify homologous plant palmitoyl-ACP thioesterases, but the resulting sequences obtained therefrom may also provide a further method to obtain plant palmitoyl-ACP thioesterases from other plant sources. In particular, PCR may be a useful technique to obtain related plant thioesterases from sequence data provided herein. One skilled in the art will be able to design oligonucleotide probes based upon sequence comparisons or regions of typically highly conserved sequence.

Once the nucleic acid sequence is obtained, the transcription, or transcription and translation (expression), of the plant palmitoyl-ACP thioesterase in a host cell is desired to produce a ready source of the enzyme and/or modify the composition of fatty acids and/or triglycerides found therein. Other useful applications may be found when the host cell is a plant host cell, in vitro and in vivo.

For example, by increasing the amount of palmitoyl-ACP preferring thioesterase available to the plant FAS complex, an increased percentage of palmitate may be provided. In a like manner, for some applications, by decreasing the amount of stearoyl-ACP desaturase available to the plant FAS complex in conjunction with an increase of the amount of palmitoyl-ACP thioesterase available, a substantial increase in the saturated fatty acids stearate and palmitate may be obtained.

The nucleic acid sequences which encode plant palmitoyl-ACP thioesterases may be used in various constructs, for example, as probes to obtain further sequences. Alternatively, these sequences may be used in conjunction with appropriate regulatory sequences to increase levels of the respective thioesterase of interest in a host cell for recovery or study of the enzyme in vitro or in vivo or to decrease levels of the respective thioesterase of interest for some applications when the host cell is a plant entity, including plant cells, plant parts (including but not limited to seeds, cuttings or tissues) and plants.

A nucleic acid sequence encoding a plant palmitoyl-ACP thioesterase of this invention may include genomic, cDNA or mRNA sequence. By "encoding" is meant that the sequence corresponds to a particular amino acid sequence either in a sense or anti-sense orientation. By "extrachromosomal" is meant that the sequence is outside of the plant genome of which it is naturally associated. By "recombinant" is meant that the sequence contains a genetically engineered modification through manipulation via mutagenesis, restriction enzymes, and the like. A cDNA sequence may or may not contain pre-processing sequences, such as transit peptide sequences. Transit peptide sequences facilitate the delivery of the protein to a given organelle and are cleaved from the amino acid moiety upon entry into the organelle, releasing the "mature" sequence. The use of the precursor plant palmitoyl-ACP thioesterase DNA sequence is preferred in plant cell expression cassettes. Other plastid transit peptide sequences, such as a transit peptide of seed ACP, may be employed to translocate the plant palmitoyl-ACP thioesterase of this invention to various organelles of interest. See, U.S. Ser. No. 07/437,764, filed Nov. 15, 1989 and European Patent Application Publication No. 189,707. In a like manner, once a given plant palmitoyl-ACP thioesterase transit peptide is obtained, it may be used to translocate sequences other than its native coding region. Sequence comparisons to the various Class II thioesterase clones provides information about the transit peptide region for these thioesterase clones. The mature N-terminus of the purified bay C12:0-ACP thioesterase was originally determined by amino acid sequencing as residue 84 (Voelker et al. (1992) *Science* 257:72–74). However, this would place the most N-terminal region conserved between all FatB representatives (residues 60–82 for bay thioesterase, FIG. 5) into the transit peptide. This sequence would be unusual for stromal transit peptides, not only because of the high degree of sequence conservation, but also because it contains a hydrophobic domain resembling thylakoid transit peptides. We now believe that this conserved region is not part of the transit sequence, and that it is included in the N-terminal portion of the processed mature protein. Consistent with this hypothesis, expression of bay thioesterase in transgenic canola seeds produces a bay thioesterase having a $M_r$ of 40 kD, i.e. larger than the 34 kD purified seed protein. The 40 kD form may represent the in vivo state of bay thioesterase, with the 34 kD from resulting from limited N-terminal proteolysis during purification.

Furthermore, as discussed above the complete genomic sequence of the plant palmitoyl-ACP thioesterase may be obtained by the screening of a genomic library with a probe, such as a cDNA probe, and isolating those sequences which regulate expression in seed tissue. In this manner, the transcription and translation initiation regions, introns, and/ or transcript termination regions of the plant palmitoyl-ACP thioesterase may be obtained for use in a variety of DNA constructs, with or without the thioesterase structural gene. Thus, nucleic acid sequences corresponding to the plant palmitoyl-ACP thioesterase of this invention may also provide signal sequences useful to direct transport into a plastid, 5' upstream non-coding regulatory regions (promoters) having useful tissue and timing profiles, 3' downstream non-coding regulatory region useful as transcriptional and translational regulatory regions and may lend insight into other features of the gene.

Once the desired plant palmitoyl-ACP thioesterase nucleic acid sequence is obtained, it may be manipulated in a variety of ways. Where the sequence involves non-coding flanking regions, the flanking regions may be subjected to resection, mutagenesis, etc. Thus, transitions, transversions, deletions, and insertions may be performed on the naturally occurring sequence. In addition, all or part of the sequence may be synthesized. In the structural gene, one or more codons may be modified to provide for a modified amino acid sequence, or one or more codon mutations may be introduced to provide for a convenient restriction site or other purpose involved with construction or expression. The structural gene may be further modified by employing synthetic adapters, linkers to introduce one or more convenient restriction sites, or the like.

The nucleic acid or amino acid sequences encoding a plant palmitoyl-ACP thioesterase of this invention may be combined with other non-native, or "heterologous", sequences in a variety of ways. By "heterologous" sequences is meant any sequence which is not naturally found joined to the plant palmitoyl-ACP thioesterase, including, for example, combinations of nucleic acid sequences from the same plant which are not naturally found joined together.

The DNA sequence encoding a plant palmitoyl-ACP thioesterase of this invention may be employed in conjunction with all or part of the gene sequences normally associated with the thioesterase. In its component parts, a DNA thioesterase encoding sequence is combined in a DNA construct having, in the 5' to 3' direction of transcription, a transcription initiation control region capable of promoting transcription and translation in a host cell, the DNA sequence encoding plant palmitoyl-ACP thioesterase and a transcription and translation termination region.

Potential host cells include both prokaryotic and eukaryotic cells. A host cell may be unicellular or found in a multicellular differentiated or undifferentiated organism depending upon the intended use. Cells of this invention may be distinguished by having a plant palmitoyl-ACP thioesterase foreign to the wild-type cell present therein, for example, by having a recombinant nucleic acid construct encoding a plant palmitoyl-ACP thioesterase therein.

Depending upon the host, the regulatory regions will vary, including regions from viral, plasmid or chromosomal genes, or the like. For expression in prokaryotic or eukaryotic microorganisms, particularly unicellular hosts, a wide variety of constitutive or regulatable promoters may be employed. Expression in a microorganism can provide a ready source of the plant enzyme. Among transcriptional initiation regions which have been described are regions from bacterial and yeast hosts, such as *E. coli, B. subtilis, Sacchromyces cerevisiae*, including genes such as beta-galactosidase, T7 polymerase, tryptophan E and the like.

For the most part, the constructs will involve regulatory regions functional in plants which provide for modified production of plant palmitoyl-ACP thioesterase, and possibly, modification of the fatty acid composition. The open reading frame, coding for the plant palmitoyl-ACP thioesterase or functional fragment thereof will be joined at its 5' end to a transcription initiation regulatory region such as the wild-type sequence naturally found 5' upstream to the thioesterase structural gene. Numerous other transcription initiation regions are available which provide for a wide variety of constitutive or regulatable, e.g., inducible, transcription of the structural gene functions. Among transcriptional initiation regions used for plants are such regions associated with the structural genes such as for nopaline and mannopine synthases, or with napin, ACP promoters and the like. The transcription/translation initiation regions corresponding to such structural genes are found immediately 5' upstream to the respective start codons. In embodiments wherein the expression of the thioesterase protein is desired in a plant host, the use of all or part of the complete plant palmitoyl-ACP thioesterase gene is desired; namely all or part of the 5' upstream non-coding regions (promoter) together with the structural gene sequence and 3' downstream non-coding regions may be employed. If a different promoter is desired, such as a promoter native to the plant host of interest or a modified promoter, i.e., having transcription initiation regions derived from one gene source and translation initiation regions derived from a different gene source, including the sequence encoding the plant palmitoyl-ACP thioesterase of interest, or enhanced promoters, such as double 35S CaMV promoters, the sequences may be joined together using standard techniques.

For such applications when 5' upstream non-coding regions are obtained from other genes regulated during seed maturation, those preferentially expressed in plant embryo tissue, such as ACP and napin-derived transcription initiation control regions, are desired. Such "seed-specific promoters" may be obtained and used in accordance with the teachings of U.S. Ser. No. 07/147,781, filed Jan. 25, 1988 (now U.S. Ser. No. 07/550,804, filed Jul. 9, 1990), and U.S. Ser. No. 07/494,722 filed on or about Mar. 16, 1990 having a title "Novel Sequences Preferentially Expressed In Early Seed Development and Methods Related Thereto," which references are hereby incorporated by reference. Transcription initiation regions which are preferentially expressed in seed tissue, i.e., which are undetectable in other plant parts, are considered desirable for fatty acid modifications in order to minimize any disruptive or adverse effects of the gene product.

Regulatory transcript termination regions may be provided in DNA constructs of this invention as well. Transcript termination regions may be provided by the DNA sequence encoding the plant palmitoyl-ACP thioesterase or a convenient transcription termination region derived from a different gene source, for example, the transcript termination region which is naturally associated with the transcript initiation region. Where the transcript termination region is from a different gene source, it will contain at least about 0.5 kb, preferably about 1-3 kb of sequence 3' to the structural gene from which the termination region is derived.

Plant expression or transcription constructs having a plant palmitoyl-ACP thioesterase as the DNA sequence of interest for increased or decreased expression thereof may be employed with a wide variety of plant life, particularly, plant life involved in the production of vegetable oils for edible and industrial uses. Most especially preferred are temperate oilseed crops. Plants of interest include, but are not limited to, rapeseed (Canola and High Erucic Acid varieties), sunflower, safflower, cotton, Cuphea, soybean, peanut, coconut and oil palms, and corn. Depending on the method for introducing the recombinant constructs into the host cell, other DNA sequences may be required. Importantly, this invention is applicable to dicotyledyons and monocotyledons species alike and will be readily applicable to new and/or improved transformation and regulation techniques.

The method of transformation is not critical to the instant invention; various methods of plant transformation are currently available. As newer methods are available to transform crops, they may be directly applied hereunder. For example, many plant species naturally susceptible to Agrobacterium infection may be successfully transformed via tripartite or binary vector methods of Agrobacterium mediated transformation. In addition, techniques of microinjection, DNA particle bombardment, electroporation have been developed which allow for the transformation of various monocot and dicot plant species.

In developing the DNA construct, the various components of the construct or fragments thereof will normally be inserted into a convenient cloning vector which is capable of replication in a bacterial host, e.g., *E. coli*. Numerous vectors exist that have been described in the literature. After each cloning, the plasmid may be isolated and subjected to further manipulation, such as restriction, insertion of new fragments, ligation, deletion, insertion, resection, etc., so as to tailor the components of the desired sequence. Once the construct has been completed, it may then be transferred to an appropriate vector for further manipulation in accordance with the manner of transformation of the host cell.

Normally, included with the DNA construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Depending upon the number of different host species the expression construct or components thereof are introduced, one or more markers may be employed, where different conditions for selection are used for the different hosts.

It is noted that the degeneracy of the DNA code provides that some codon substitutions are permissible of DNA sequences without any corresponding modification of the amino acid sequence.

As mentioned above, the manner in which the DNA construct is introduced into the plant host is not critical to this invention. Any method which provides for efficient transformation may be employed. Various methods for plant cell transformation include the use of Ti- or Ri-plasmids, microinjection, electroporation, DNA particle bombardment, liposome fusion, DNA bombardment or the like. In many instances, it will be desirable to have the construct bordered on one or both sides by T-DNA, particularly having the left and right borders, more particularly the right border. This is particularly useful when the construct uses *A. tumefaciens* or *A. rhizogenes* as a mode for transformation, although the T-DNA borders may find use with other modes of transformation.

Where Agrobacterium is used for plant cell transformation, a vector may be used which may be introduced into the Agrobacterium host for homologous recombination with T-DNA or the Ti- or Ri-plasmid present in the Agrobacterium host. The Ti- or Ri-plasmid containing the T-DNA for recombination may be armed (capable of causing gall formation) or disarmed (incapable of causing gall formation), the latter being permissible, so long as the vir genes are present in the transformed Agrobacterium host. The armed plasmid can give a mixture of normal plant cells and gall.

In some instances where Agrobacterium is used as the vehicle for transforming plant cells, the expression construct bordered by the T-DNA border(s) will be inserted into a broad host spectrum vector, there being broad host spectrum vectors described in the literature. Commonly used is pRK2 or derivatives thereof. See, for example, Ditta et al., *PNAS USA*, (1980) 77:7347–7351 and EPA 0 120 515, which are incorporated herein by reference included with the expression construct and the T-DNA will be one or more markers, which allow for selection of transformed Agrobacterium and transformed plant cells. A number of markers have been developed for use with plant cells, such as resistance to chloramphenicol, the aminoglycoside G418, hygromycin, or the like. The particular marker employed is not essential to this invention, one or another marker being preferred depending on the particular host and the manner of construction.

For transformation of plant cells using Agrobacterium, explants may be combined and incubated with the transformed Agrobacterium for sufficient time for transformation, the bacteria killed, and the plant cells cultured in an appropriate selective medium. Once callus forms, shoot formation can be encouraged by employing the appropriate plant hormones in accordance with known methods and the shoots transferred to rooting medium for regeneration of plants. The plants may then be grown to seed and the seed used to establish repetitive generations and for isolation of vegetable oils.

Once a transgenic plant is obtained which is capable of producing seed having a modified fatty acid composition, traditional plant breeding techniques, including methods of mutagensis, may be employed to further manipulate the fatty acid composition. Alternatively, additional foreign fatty acid modifying DNA sequence may be introduced via genetic engineering to further manipulate the fatty acid composition. It is noted that the method of transformation is not critical to this invention. However, the use of genetic engineering plant transformation methods, i.e., the power to insert a single desired DNA sequence, is critical. Heretofore, the ability to modify the fatty acid composition of plant oils was limited to the introduction of traits that could be sexually transferred during plant crosses or viable traits generated through mutagensis. Through the use of genetic engineering techniques which permits the introduction of inter-species genetic information and the means to regulate the tissue-specific expression of endogenous genes, a new method is available for the production of plant seed oils with modified fatty acid compositions. In addition, there is the potential for the development of novel plant seed oils upon application of the tools described herein.

One may choose to provide for the transcription or transcription and translation of one or more other sequences of interest in concert with the expression of a plant palmitoyl-ACP thioesterase in a plant host cell. In particular, the reduced expression of stearoyl-ACP desaturase in combination with expression of a plant palmitoyl-ACP thioesterase may be perferred in some applications.

When one wishes to provide a plant transformed for the combined effect of more than one nucleic acid sequence of interest, typically a separate nucleic acid construct will be provided for each. The constructs, as described above contain transcriptional or transcriptional or transcriptional and translational regulatory control regions. One skilled in the art will be able to determine regulatory sequences to provide for a desired timing and tissue specificity appropriate to the final product in accord with the above principles set forth as to the respective expression or anti-sense constructs. When two or more constructs are to be employed, whether they are both related to the same fatty acid modifying sequence or a different fatty acid modifying sequence, it may be desired that different regulatory sequences be employed in each cassette to reduce spontaneous homologous recombination between sequences. The constructs may be introduced into the host cells by the same or different methods, including the introduction of such a trait by crossing transgenic plants via traditional plant breeding methods, so long as the resulting product is a plant having both characteristics integrated into its genome.

A plant stearoyl-ACP desaturase of this invention includes any sequence of amino acids, such as a protein, polypeptide, or peptide fragment, obtainable from a plant source which is capable of catalyzing the insertion of a first double bond into a fatty acyl-ACP moiety in a plant host cell, i.e., in vivo, or in a plant cell-like environment, i.e. in vitro. "A plant cell-like environment" means that any necessary conditions are available in an environment (i.e., such factors as temperatures, pH, lack of inhibiting substances) which will permit the enzyme to function In particular, this invention relates to enzymes which add such a first double bond at the ninth carbon position in a fatty acyl-ACP chain. There may be similar plant desaturase enzymes of this invention with different specificities, such as the Δ-12 desaturase of carrot.

By decreasing the amount of desaturase, an increased percentage of saturated fatty acids is provided. Using anti-sense, transwitch, ribozyme or some other stearoyl-ACP desaturase reducing technology, a decrease in the amount of desaturase available to the plant cell is produced, resulting in a higher percentage of saturates such as one or more of laurate (C12:0), myristate (C14:0), palmitate (C16:0), stearate (C18:0), arachidate (C20:0), behemate (C22:0) and lignocerate (C24:0). In rapeseed reduced desaturase results in increased stearate levels and total saturates. Of special interest is the production of triglycerides having increased levels of palmitate or palmitate and stearate. In addition, the production of a variety of ranges of such saturates is desired. Thus, plant cells having lower and higher levels of palmitate or palmitate and stearate fatty acids are contemplated. For example, fatty acid compositions, including oils, having a 10% level of palmitate and stearate as well as compositions designed to have up to an appropriate 60% level of palmitate and stearate or other such modified fatty acid(s) composition are contemplated.

Oils with increased percentages of palmitate or palmitate and stearate, are desired. Increased stearate percentages (by weight) ranging from native up to 25 fold are described. By manipulation of various aspects of the DNA constructs (e.g., choice of promoters, number of copies, etc.) and traditional breeding methods, one skilled in the art may achieve even greater levels of stearate. By combination of the plant desaturase sequence in combination with the expression of a plant palmitoyl-ACP thioesterase in seed tissue, an increased percentage of palmitate and stearate can be achieved in rapeseed and other plant species.

DNA sequence of C. tinctorius desaturase gene, as well as DNA sequences of desaturase gene from a Ricinus, a Brassica and a Simmondsia plant are found in U.S. Ser. No. 07/949,102, filed Sep. 21, 1992, now pending.

The invention now being generally described, it will be more readily understood by reference to the following examples which are included for purposes of illustration only and are not intended to limit the present invention.

EXAMPLES

Example 1

Thioesterase Gene Sequences

A. Mango

A mango cDNA bank is prepared using the methods as described in Stratagene Zap cDNA synthesis kit (Stratagene; La Jolla, Calif.). Mango embryos are collected from green (mature but not soft) mangos purchased from a grocery store. Total RNA is isolated from the embryos by modifying the DNA isolation method of Webb and Knapp (*Plant Mol. Biol. Reporter* (1990) 8:180–195). Buffers include:

REC: 50 mM TrisCl pH 9, 0.7M NaCl 10 mM EDTA pH8, 0.5% CTAB.

REC+: Add B-mercaptoethanol to 1% immediately prior to use.

RECP: 50 mM TrisCl pH9, 10 mM EDTA pH8, and 0.5% CTAB.

RECP+: Add B-mercaptoethanol to 1% immediately prior to use.

For extraction of 1 g of tissue, 10 ml of REC+ and 0.5 g of PVPP is added to tissue that has been ground in liquid nitrogen and homogenized. The homogenized material is centrifuged for 10 min at 1200 rpm. The supernatant is poured through miracloth onto 3 ml cold chloroform and homogenized again. After centrifugation, 12,000 RPM for 10 min, the upper phase is taken and its volume determined. An equal volume of RECP+ is added and the mixture is allowed to stand for 20 min. at room temperature. The material is centrifuged for 20 min. at 10,000 rpm twice and the supernatant is discarded after each spin. The pellet is dissolved in 0.4 ml of 1M NaCl (DEPC) and extracted with an equal volume of phenol/chloroform. Following ethanol preciptation, the pellet is dissolved in 1 ml of DEPC water.

Briefly, the cloning method for cDNA synthesis is as follows. First strand cDNA synthesis is according to Stratagene instruction Manual with some modifications according to Robinson, et al.(*Methods in Molecular and Cellular Biology* (1992) 3:118–127). In particular, 30 μg of LiCl precipitated total RNA is used instead of 5 μg of poly(A)+ RNA and the reaction is incubated at 45° C. rather than 37° C. for 1 hour.

The library is screened by plating ~15000 pfu on LE392 E. coli cells per 150 mm NZY plate in 0.9% NZY top agarose to provide approximately 300,000 plaques for screening. Plaque lifts onto Colony/Plaque Screen (NEN) and denaturization, neutralization and baking was done as described (Stratagene).

Filters are prehybridized at room temperature in 50% formamide, 5×SSC, 10×Denharts, 0.1% (w/v) SDS, 5 mM Na$_2$EDTA, 0.1 mg/ml denatured salmon sperm DNA (from 2 hours to overnight) in plastic boxes with teflon screens between the filters. Hybridization is conducted at room temperature in the same buffer as above with added 10% (w/v) dextran sulfate and probe. Probe used is a fragment of the Brassica Class I thioesterase containing nucleotides 27–1191 of the sequence shown in FIG. 11. Filters are washed for 2 minutes with 1×SSC/0.1% SDS, and twice for 20 minutes each wash with 0.1×SSC/0.1% SDS. Filters are exposed to X-ray film overnight. Twenty-six hybridizing plaques were identified. Plaque purification and phagemid excision were conducted as described in Stratagene Zap cDNA Synthesis Kit instructions.

Of 25 purified phagemids analyzed, thioesterase clones from two classes were identified by DNA sequence analysis. Nine of the clones encode Class I thioesterase and sixteen encode Class II thioesterase. The sequence of the longest member of each class are shown in FIGS. 1 (Class I) and 2 (Class II).

The mango library was rescreened for additional thioesterase clones. Phage (147200 pfu) are plated on 16 NZY plates (9200 pfu/plate) as described above. For each plate, approximately 9200 phage are mixed with 600 μl of LE392 cells (1 O.D., in 10 mM MgS$_{o4}$) and incubated at 37° C. for 20 min. Cells are then plated by adding 6 mls of 0.9% NZY top agarose (55° C.) and poured directly onto an NZY plate that has been warmed to 37° C. Plates are incubated at 37° C. overnight. Plaque lifts onto Colony/Plaque Screen (NEN) and denaturization and neutralization are as described above (Stratagene). Filters are air dried overnight, prehybed and hybridized as described above. A PCR fragment of the mango class II thioesterase (FIG. 2) is used as the probe. The probe is prepared from pCGN5214 plasmid as the PCR template using the following primers:

4316 (SEQ ID NO:13) 5' CGTCTAGACATATGCCAAG-GACTTTTATTAAC 3'

4343 (SEQ ID NO:14) 5' CGGAATTCCGAGACTG-CAGTAAGGCTAATC 3'.

The following PCR conditions are used: 94° C. 15 sec., 50° C. 30 sec., 72° C. 30 sec. for 30 cycles in a Perkin-Elmer GeneAmp PCR System 9600 thermocycler. The approximately 1200 base pair resulting PCR fragment is radiolabeled using the Stratagene "Prime-it II Random Prime Labeling Kit". The labeled DNA fragments are passed through a Sephadex-G50 spin column to separate unincorporated dNTPs. The labeled probe is added to the hybridization solution. After overnight incubation in this solution at room temperature, the membranes are washed once for 15 minutes at room temperature with 1×SSC plus 0.1% SDS followed by two washes with 0.1×SSC plus 0.1% SDS under the same conditions. The membranes are exposed to X-ray film for 3 days. A total of 28 positive signals were seen on the X-ray films, and the corresponding clones were picked for further screening. By DNA sequence analysis, 17 of the clones were identified as encoding acyl-ACP thioesterases. All but one of the clones were identical to the mango Class II clone provided in FIG. 2. Sequence of the other clone, M4-23, which is closely related to the previous mango Class II thioesterase clone, is provided in FIG. 12.

B. Leek

Similarly to the methods described above for isolation of mango thioesterase sequences, a leek cDNA library in lambda ZAP (Stratagene) is screened for thioesterase clones. Phage (2×10$^5$ pfu) are plated on 10 NZY plates (20,000 pfu/plate) as described above. For each plate, approximately 20,000 phage are mixed with 600 µl of LE392 cells (1 O.D., in 10 mM MgSO$_4$) and incubated at 37° C. for 15 min. Cells are then plated by adding 7 ml of 0.9% NZY top agarose (55° C.) and poured directly onto an NZY plate (see above). Plates are incubated at 37° C. overnight. Following incubation at 4° C. for 2 hours, phage are lifted onto colony/plaque screen membranes (New England Nuclear) as described above. Double lifts are made to prevent false positive signals. After lifting, the membranes are denatured, neutralized, and rinsed as described above. The phage DNA is then crosslinked to the membrane using an UV Stratalinker 2400 (Stratagene). Membranes are then submerged in prehybridization solution containing 50% formamide and 5×SSC, and incubated at room temperature for 2 hours (with shaking).

Three thioesterase DNA fragments were chosen for use in hybridization reactions. The mixed probe contained (1) a bay 12:0 thioesterase fragment (gel-purified 400 bp PstI fragment of the bay cDNA shown in FIG. 5); (2) mango Class II thioesterase (FIG. 2) and (3) Brassica Class I thioesterase (FIG. 11). Approximately 100 ng of each purified DNA fragment is radio-labelled using the Pharmacia "Ready-To-Go" DNA labeling kit. Following the manufacturer's instructions, 50 µCi $^{32}$P-dCTP is used for each reaction. The labeled DNA fragments are passed through a Sephadex-G25 spin column to separate unincorporated dNTPs. The three labeled probes are mixed and added to 75 ml of hybridization solution (prehybridization solution containing 10% dextran sulfate). After overnight incubation in this solution at room temperature, the membranes are washed twice for 15 minutes at room temperature with 1×SSC and 0.1% SDS, followed by two washes with 0.1× SSC plus 0.1% SDS under the same conditions. The membranes are exposed to X-ray film overnight.

A total of 28 positive signals were seen on the X-ray films. Five of the clones (designated as LTE 6-1, 8-2, 8-3, 9-1, 9-4) were picked for further screening. Phage are eluted from the plates in the area of the positive signals by soaking a core of the agarose in 200 µl of SM buffer. Each phage was plated out as described above at a titer of about 100 pfu/plate. Phage DNA were transferred to membranes, denatured, neutralized, and cross-linked as described above. The membranes were hybridized with the same probes used in the initial screening, and washed under identical conditions. The majority of the plaques were also positive in the secondary screening. Well-isolated, positive plaques were picked and subjected to excision using the Exassist/SOLR system from Stratagene. The cloned DNA inserts, now in a pBluescript double-stranded phagemid, were purified, and sequenced using an ABS automated sequencer.

DNA sequences of the five selected clones revealed that clone 8-2, 8-3 and 9-4 are identical, while 9-1 and 6-1 appear to be identical and are very closely related, if not identical to the other three clones. The leek thioesterases encoded by these cDNA clones show high homology to Class II thioesterases. Preliminary nucleic acid sequence and translated amino acid sequence of 8-2 and 9-1 are provided in FIGS. 3 and 4.

C. Cuphea

Acyl-ACP thioesterase clones are isolated from *Cuphea hookeriana* as described in WO 94/10288. Sequence of Class II *C. hookeriana* clones are provided in FIGS. 6 and 7.

D. Elm

A Class II acyl-ACP thioesterase clone is isolated from elm as described in WO 94/10288. DNA sequence of this clone is provided in FIG. 8.

Example 2

Expression of Acyl-ACP Thioesterases in *E. coli*

To determine substrate preference of thioesterases encoded by the isolated sequences, recombinant DNA constructs for expression in *E. coli* are prepared.

A. Mango

To insert the mango Class II thioesterase encoding sequence into a pET3a expression vector, the mango Class II thioesterase cDNA, MANI-2 is digested with EcoRI. The linearized plasmid is used as a PCR template using the following primers:

4317 (SEQ ID NO:15)=5' CGTCTAGACATATGCT-TGACTGGAAACC 3';

4343 (SEQ ID NO:14)=5' CGGAATTCCGAGACTG-CAGTAAGGCTAATC 3'.

The following PCR conditions are used: 94° C. 1 min., 60° C. 30 sec., 72° C. 2 min for 30 cycles in a Perkin-Elmer GeneAmp PCR System 9600 thermocycler. The approximately 1100 base pair resulting PCR fragment contains an NdeI site immediately upstream of the postulated mature protein start codon (Leucine 112). The fragment is cloned into a TA1000 vector (Invitrogen) to generate pCGN5217. pCGN5217 is digested with NdeI and EcoR1 to produce a fragment containing the majority of the mature mango thioesterase coding sequence. The NdeI/EcoRI fragment is inserted into NdeI/EcoRI digested plasmid expression vector pET3a (Novagen; Madison, Wis.) resulting in pCGN5218. For expression analysis, pCGN5218 is used to transform *E. coli* strain BL21(DE3) which contains a T7 polymerase (Novagen).

An additional construct is prepared which includes a different mature protein N-terminus candidate (leucine 88). The PCR is conducted using primers 4466 and 4464 with the following PCR conditions: 94° C. 1 min., 60° C. 30 sec., 72° C. 2 min for 30 cycles. The PCR fragment is cloned into CloneAmp System (GIBCO BRL), and the resulting plasmid is digested with NdeI and EcoRI to produce an approximately 1200 base pair fragment containing the majority of the mature mango thioesterase coding sequence. The NdeI/EcoRI fragment is inserted into NdeI/EcoRI digested plasmid expression vector pET3a (Novagen). For expression analysis, the resulting plasmid is used to transform *E. coli* strain BL21(DE3) which contains a T7 polymerase (Novagen).

For expression as a lacZ fusion protein, PCR is conducted with primers 4463 and 4464 to make an ~1100 base pair XbaI/EcoRI fragment beginning at XbaI site inserted 5' to leucine 112 codon and ending at EcoRI site inserted at nucleotide 1561. Alternatively, primers 4465 and 4464 are used to make an ~1200 base pair fragment beginning with XbaI site inserted 5' to proline 81 codon and ending at EcoRI site inserted at nucleotide 1561. PCR conditions are as follows: 94° C. 1 min., 60° C. 30 sec., 72° C. 2 min for 30 cycles.

The PCR fragments are cloned into CloneAmp System (GIBCO BRL). The plasmids are digested with XbaI and EcoR1 to produce an approximately 1100 or 1200 base pair fragment containing the majority of the mature mango thioesterase coding sequence from one of the two postulated mature protein N-termini. The XbaI/EcoR1 fragment is inserted into XbaI/EcoR1 digested plasmid expression vector such as pBCSK (Stratagene). For expression analysis the vectors are used to transform *E. coli* fadD+ cells (commercially available cells such as SURE cells from BRL may also be used) or an *E. coli* mutant, fadD, which lacks medium-chain specific acyl-CoA synthetase (Overath et al., *Eur. J. Biochem.* (1969) 7:559–574).

To express the mango M4-23 (pCGN 5234) Class II thioesterase encoding sequence as a lacZ fusion protein, the clone is cut with SphI and HindIII. The resulting fragment is isolated from a 0.7% agarose TBE gel using Gene CleanII Kit (Bio101). The fragment is ligated into pUC18 (Novagen; Madison, Wis.) also digested with SphI and HindIII to generate pCGN5235. pCGN5235 is digested with SmaI and HindIII and subcloned into pBC SK (Stratagene) also digested with SmaI and HindIII to generate pCGN5236.
PCR primers 4317 (SEQ ID NO:15) CGTCTAGACATATGCT-TGACTGGAAACC 4343 (SEQ ID NO:14) CGGAATTCCGAGACTGCAG-TAAGGCTAATC 4463 (SEQ ID NO:16) CUACUACUACUAGCTCTA-GAGCTTGACTGGAAACC 4464 (SEQ ID NO:17) CAUCAUCAUCAUCCGAAT-TCGCAGTAAGGCTAATC 4465 (SEQ ID NO:18) CUACUACUACUAGCTCTA-GAGCCAAGGACTTTTAT 4466 (SEQ ID NO:19) CUACUACUACUAGCGCATAT-GCCAAGGACTTTTAT For thioesterase activity assay a 20 ml culture of *E. coli* cells containing the mango thioesterase construct and a similar culture of control cells are grown at 25°–37° C. to an OD600 of ~0.5. Induction of the thioesterase expression may be achieved by the addition of IPTG to 0.4 mM followed by 1–18 hours further growth.

A ten-ml aliquot of each culture is assayed for specific activity towards C10:0-ACP, C12:0-ACP, C14:0-ACP, C16:0-ACP, C18:0-ACP and C18:1-ACP substrates as follows. Cells are harvested by centrifugation, resuspended in 0.4 ml assay buffer and lysed by sonication. Cell debris may be removed by further centrifugation. The supernatant can then used in thioesterase activity assays per Davies et al., *Arch. Biochem & Biophys.* (1991) 290:37–45 using C10:0-ACP, C12:0-ACP, C14:0-ACP, C16:0-ACP, C18:0-ACP and C18:1-ACP substrates.

For analysis of the fatty acid composition, a 4.5 ml sample of *E. coli* cells grown and induced as described above is transferred into a 15 ml glass vial with a teflon-lined cap. 100μl of a 1 mg/ml standards solution containing 1 mg/ml each of C11:0 free fatty acid, C15:0 free fatty acid, and C17:0 TAG in 1:1 chloroform/methanol is added to the sample, followed by addition of 200 μl of glacial acetic acid and 10 ml of 1:1 chloroform/methanol. The samples are vortexed to mix thoroughly and centrifuged for 5 minutes at 1000 rpm for complete phase separation. The lower (chloroform) phase is carefully removed and transferred to a clean flask appropriate for use in a rotary evaporator (Rotovap). The sample is evaporated to near dryness. As medium-chain fatty acids appear to evaporate preferentially after solvent is removed, it is important to use just enough heat to maintain the vials at room temperature. The dried samples are methanolyzed by adding 1 ml of 5% sulfuric acid in methanol, transferring the samples to a 5 ml vial, and incubating the sample in a 90° C. water bath for 2 hours. The sample is allowed to cool, after which 1 ml of 0.9% NaCl and 300 μl of hexane are added. The sample is vortexed to mix thoroughly and centrifuged at 1000 rpm for 5 minutes. The top (hexane) layer is carefully removed and placed in a plastic autosampler vial with a glass cone insert, followed by capping of the vial with a crimp seal.

The samples are analyzed by gas-liquid chromatography (GC) using a temperature program to enhance the separation of components having 10 or fewer carbons. The temperature program used provides for a temperature of 140° C. for 3 minutes, followed by a temperature increase of 5° C./minute until 230° C. is reached, and 230° C. is maintained for 11 minutes. Samples are analyzed on a Hewlett-Packard 5890 (Palo Alto, Calif.) gas chromatograph. Fatty acid content calculations are based on the internal standards.

Results of thioesterase activity and fatty acid composition analyses of *E. coli* cells expressing the mango M4-23 clone are presented in Table II below.

TABLE II

| Acyl-ACP Substrate | Activity (cpm/μg protein) | |
|---|---|---|
| | M4-23 | Control |
| 10:0 | 26.5 | 29.6 |
| 12:0 | 62.4 | 64.1 |
| 14:0 | 113.8 | 99.8 |
| 16:0 | 757.4 | 289.7 |
| 18:0 | 484.2 | 332.8 |
| 18:1 | 687.0 | 209.9 |

The above results demonstrate that the M4-23 mango Class II thioesterase has specificity towards 16:0-ACP substrates, with some activity also on C18:1-ACP and C18:0-ACP substrates.

B. Leek

PCR reactions are used for insertion of convenient restriction sites into the 5' of the mature coding region of the thioesterase cDNA. PCR primers are designed for introduction of unique restriction sites (SacI-NdeI at 5' end and KpnI at 3' end right after the stop codon). The entire mature protein encoding region (beginning at the leucine at amino acid position 118 of FIG. 4) of the leek thioesterase with the described restriction sites at the ends is generated by PCR. The resulting DNA fragment is inserted into a pBluescript cloning vector to create a LacZ fusion construct, or alternatively ligated into a pET plasmid vector to make a non-fusion construct.

*E. coli* cells transformed with leek thioesterase lacZ fusion constructs are grown and induced by IPTG as described above. Cell lysates are assayed for thioesterase activity as described above.

Results of thioesterase activity assays with the 9-1 and 8-2 leek clones indicate that the leek Class II thioesterases have high specificity towards 16:0-ACP substrates, with some minor activities also observed with 14:0, 18:0 and 18:1-ACP substrates.

C. Cuphea and Elm

Expression of *Cuphea hookeriana* (CUPH-1 and CUPH-2) and elm Class II acyl-ACP thioesterase clones in *E. coli* was described in WO 94/10288. The Cuphea CUPH-2 clone demonstrated increased activity with C8 and C10 substrates. This clone was determined to represent the thioesterase activity responsible for the production of C8 and C10 fatty acid in native *Cuphea hookeriana* seeds. Expression of the CUPH-1 clone, however, revealed increased hydrolysis activity on C16:0 and C14:0-ACP substrates. Since *C. hookeriana* seeds do not contain significant levels of C14:0 and C16:0 fatty acids, it was not clear if the production of these fatty acids was the direct result of the CUPH-1 expression, or was the result of some activity in the *E. coli* cells themselves.

Total fatty acid analysis of liquid cultures of CUPH-1 transformed K27 (fadD)) are shown in Table III below.

TALBE III

| Clone | Substrate | Fatty Acids (nmol/ml) |
|---|---|---|
| CUPH-1 | 12:0-ACP | 2 |
| " | 12:1-ACP | 0.3 |
| " | 14:0-ACP | 225.1 |
| " | 14:1-ACP | 1.1 |
| " | 16:0-ACP | 281 |
| " | 16:1-ACP | 124.4 |
| " | 18:1-ACP | 92.7 |
| control | 12:0-ACP | 2.9 |
| " | 12:1-ACP | 0.7 |
| " | 14:0-ACP | 19.3 |
| " | 14:1-ACP | 2.4 |
| " | 16:0-ACP | 141.2 |
| " | 16:1-ACP | 59.1 |
| " | 18:1-ACP | 41.8 |

Levels of 14:0, 16:0, 16:1 and 18:1 are elevated in comparison to the control. As demonstrated herein by expression of the CUPH-1 clone in transgenic plant cells, the *E. coli* phenotype is the result of CUPH-1 acyl-ACP thioesterase having activity predominantly on 16:0-ACP substrates, with some lesser activity on 14:0-ACP.

Expression of an elm acyl-ACP thioesterase resulted in increased hydrolysis activity on C10:0-ACP substrates, which activity could account for the significant levels of C10:0 fatty acids in elm seeds. However, increased activity on C16:0 substrates was also observed, an unexpected result since elm seeds do not contain significant levels of C16:0 fatty acids. Data provided in WO 94/10288 suggested that the C16:0-ACP hydrolysis activity was derived from the *E. coli* cells, rather than the elm thioesterase. However, as demonstrated herein by expression of elm acyl-ACP thioesterase in seeds of transgenic plants, the observed C16:0 activity in *E. coli* is due to actual hydrolysis activity of the elm thioesterase on C16:0-ACP.

Example 3

Expression of Palmitoyl-ACP Thioesterases in Plants

A. Mango

A construct for the expression of the mango Class II thioesterase clone in plants under the regulatory control of a transcriptional initiation region from a gene preferentially expressed in plant seed tissue is prepared as follows. A SalI restriction site is introduced upstream of the start codon of the mango thioesterase open reading frame using the mango thioesterase cDNA sequence shown in FIG. 2 as a template in a polymerase chain reaction (PCR). The sense PCR primer (SEQ ID NO:20)(5'-GCTTGTCGACAAGATGGCTTCTACTG-3') includes the mango thioesterase start codon and the SalI restriction site. The antisense primer (SEQ ID NO:21)(5'-GCGTAAGCTTGCATGCTGGTCA-3') includes sequence surrounding the unique SphI site at nucleotide 421 and provides for insertion of a HindIII restriction site downstream of the SphI site. The product of the PCR reaction (~300 bp) is subcloned by digestion with SalI and HindIII into a chloramphenicol resistant vector pBCSK (Stratagene) that has also been digested with SalI and HindIII. The mango thioesterase gene is reassembled by combining the SphI—EcoR1 fragment from the mango Class II thioesterase encoding sequence (an approximately 1140 bp fragment from the nucleotide 421 SphI site through the EcoRI site located 3' to the translation stop codon at nucleotides 1561–1566) with the ~300 bp of N-terminal coding sequence using the unique SphI and EcoRI sites in the N-terminal fragment/pBCSK construct. The resulting plasmid contains the entire coding sequence and some 3'-untranslated sequence of the mango thioesterase gene flanked by SalI and NcoI (nucleotides 1425–1430) restriction sites. A fragment comprising the mango thioesterase sequence is obtained by digestion with NcoI and blunting with the Klenow fragment of DNA polymerase, followed by digestion with SalI. The blunt end/SalI mango thioesterase fragment is ligated into a napin expression cassette, pCGN3223 (described in WO 92/20236) which has been digested with XhoI, blunted and digested with SalI. The resulting expression cassette contains the mango thioesterase flanked by the napin 5'-sequences and napin 3'-sequences. This expression cassette is cloned into a binary vector for plant transformation by digestion with Asp718 and ligation to Asp718 digested pCGN1557 (McBride et al. (1990) *Plant Mol. Biol.* 14:269–276) resulting in pCGN5228. Constructs are transformed into Agrobacterium cells, such as of strain EHA101 (Hood et al., *J. Bacteriol* (1986) 168:1291–1301), by the method of Holsters et al. (*Mol. Gen. Genet.* (1978) 163:181–187).

B. Leek

Clone 9-1 contains the entire transit peptide and mature sequence of the leek Class II thioesterase. Convenient restriction digestion sites are added by PCR and a fragment containing the entire coding region and flanked by a SalI site at the 5' end and XhoI site at the 3' end is isolated. The fragment is ligated into the SalI/XhoI sites of pCGN3223 (napin expression cassette described above). The napin 5'/leek thioesterase/napin 3' construct is then inserted into pCGN1558, an Agrobacterium/plant transformation binary plasmid (McBride et al. supra). The resulting construct, pCGN5230, is transformed into an Agrobacterium strain and used to generate transformed plants.

C. Cuphea

PCR analysis of a *Cuphea hookeriana* reverse transcribed cDNA (FIG. 5 of WO 94/10288) indicated that the 5' region of the TAA 342 CUPH-1 clone was lacking a guanine nucleotide (G) following nucleotide 144 of the sequence shown in FIG. 5 of WO 94/10288. [DNA sequence analysis of the CMT9 CUPH-1 clone (FIG. 7, herein) confirms the presence of the G nucleotide in that region. Clone CMT-9 can also be used for preparation of CUPH-1 expression constructs, without the requirement for further manipulation of the reading frame in the 5' region.] Thus, a G nucleotide was inserted after nucleotide 144 in TAA 342 by PCR directed mutagenesis resulting in an encoding region beginning at the ATG at 143–145 of the sequence shown in FIG. 5 of WO 94/10288. The corrected encoding sequence was cloned into a convenient vector using SalI and XhoI sites (also inserted in the PCR reaction), resulting in KA2. A SalI fragment of the resulting clone, comprising nucleotides 137–1464 of the sequence shown in FIG. 5 of WO 94/10288 (plus the inserted G nucleotide discussed above), was cloned into napin expression cassette pCGN3223. The napin/Cuphea thioesterase/napin construct was then excised as a HindIII fragment and cloned into the binary vector pCGN1557 (McBride and Summerfelt (1990) *Plant Mol. Biol.* 14:269–276). The resulting construct, pCGN4800, was transformed into *Agrobacterium tumefaciens* and used to prepare transformed plants.

C. Elm Acyl-ACP Thioesterase Expression Construct

A construct for expression of an elm C10 and C8 acyl-ACP thioesterase in plant seed cells using a napin expression cassette is prepared as follows. The elm ULM-1 medium-chain acyl-ACP thioesterase cDNA does not appear to encode the entire thioesterase transit peptide. Thus, the elm thioesterase coding region was fused to the transit peptide encoding region from the Cuphea CUPH-1 clone as follows. pCGN4800 (CUPH-1 in napin cassette) was digested with XbaI, blunted and digested with StuI to remove the mature protein coding portion of the CUPH-1 construct. The StuI site is located at nucleotides 496–501 of the CUPH-1 sequence shown in FIG. 5 of WO 94/10288. The XbaI site is located between the end of the Cuphea thioesterase cDNA sequence and the napin 3' regulatory region. The ULM-1 mature protein encoding region is inserted into the napin/Cuphea transit peptide backbone resulting from removal of the Cuphea mature protein encoding region as follows. The ULM-1 clone is digested with XbaI, blunted and digested with StuI to obtain the elm thioesterase mature protein encoding region. The StuI site is located at nucleotides 250–255 of the sequence shown in FIG. 8, and the XbaI site is located at nucleotides 1251–1256, 3' to the stop codon. Ligation of the elm StuI/XbaI fragment into the napin/Cuphea transit peptide backbone results in pCGN4802, having the napin 5'/Cuphea transit:elm mature/napin 3' expression construct. pCGN4803 is transferred to pCGN1557 as a HindIII fragment resulting in pCGN4803, a binary construct for plant transformation.

Example 4

Plant Transformation and Analysis

A. Transformation Methods

1. Agrobacterium-mediated Transformation

Methods which may be used for Agrobacterium-mediated transformation of Brassica are described by Radke et al. (*Theor. Appl. Genet.* (1988) 75:685–694; *Plant Cell Reports* (1992) 11:499–505).

Transgenic *Arabidopsis thaliana* plants may be obtained by Agrobacterium-mediated transformation as described by Valverkens et al., (*Proc. Nat. Acad. Sci.* (1988) 85:5536–5540).

2. Particle Bombardment

DNA sequences of interest may be introduced as expression cassettes, comprising at least a promoter region, a gene of interest, and a termination region, into a plant genome via particle bombardment as described for example in European Patent Application 332 855 and in co-pending application U.S. Ser. No. 07/225,332, filed Jul. 27, 1988.

Briefly, tungsten or gold particles of a size ranging from 0.5 mM–3 mM are coated with DNA of an expression cassette. This DNA may be in the form of an aqueous mixture or a dry DNA/particle precipitate. Tissue used as the target for bombardment may be from cotyledonary explants, shoot meristems, immature leaflets, or anthers.

The bombardment of the tissue with the DNA-coated particles is carried out using a Biolistics‰ particle gun (Dupont; Wilmington, Del.). The particles are placed in the barrel at variable distances ranging from 1 cm–14 cm from the barrel mouth. The tissue to be bombarded is placed beneath the stopping plate; testing is performed on the tissue at distances up to 20 cm. At the moment of discharge, the tissue is protected by a nylon net or a combination of nylon nets with mesh ranging from 10 mM to 300 mM.

Following bombardment, plants may be regenerated following the method of Atreya, et al., (*Plant Science Letters* (1984) 34:379–383). Briefly, embryo axis tissue or cotyledon segments are placed on MS medium (Murashige and Skoog, *Physio. Plant.* (1962) 15:473) (MS plus 2.0 mg/l 6-benzyladenine (BA) for the cotyledon segments) and incubated in the dark for 1 week at 25±2° C. and are subsequently transferred to continuous cool white fluorescent light (6.8 W/m$^2$). On the 10th day of culture, the plantlets are transferred to pots containing sterile soil, are kept in the shade for 3–5 days are and finally moved to greenhouse.

The putative transgenic shoots are rooted. Integration of exogenous DNA into the plant genome may be confirmed by various methods know to those skilled in the art.

B. Plant Analysis

Plants transformed with C16:0 acyl-ACP thioesterases as described above are analyzed to determine the percentages of various fatty acids in the seeds. Plants containing elevated levels of C16:0 fatty acids are selected for further analysis, including positional analysis of fatty acids on the TAG molecules.

Developing (near-mature) seeds (10–20 seeds/sample) from transgenic plants containing the pCGN4800 and pCGN4803 constructs (expressing CUPH-1 and elm acyl-ACP thioesterases, respectively) are analyzed by GC using parameters as described for analysis of *E. coli* cell cultures. Results of these analyses from the individual transformant from the pCGN4800 and pCGN4803 transformation events demonstrating the greatest increase in the C16 fatty acid levels are provided in Table IV.

Transgenic *Brassica napus* plants (212/86) expressing the CUPH-1, elm and mango (MANI-2) thioesterase clones are analyzed to determine fatty acid composition. Mature seeds (~20 seeds/sample) from transgenic plants containing the pCGN4800, pCGN4803 and pCGN5288 are analyzed by GC using parameters as described for analysis of *E. coli* cell cultures.

In seeds from pCGN4800 (CUPH-1) transformed plants, increased levels of C16:0 fatty acids are detected. In seeds from pCGN4803 (elm) transformants, significant levels of C16:0 fatty acids are detected along with increases in C14:0 and C10:0 contents. In seeds from pCGN5288 (mango MANI-2) transformed plants, increased levels of C16:0 fatty acids are detected.

TABLE IV

| | Fatty Acyl Composition of Transgenic Canola Seeds (mol %) | | | | | | | | | | | | |
|---|---|---|---|---|---|---|---|---|---|---|---|---|---|
| | 8:0 | 10:0 | 12:0 | 14:0 | 16:0 | 16:1 | 18:0 | 18:1 | 18:2 | 18:3 | 20:0 | 20:1 | 22:0 |
| Control | N.D. | N.D. | 0.02 | 0.14 | 6.45 | 0.41 | 1.03 | 47.32 | 25.79 | 17.2 | 0.39 | 0.96 | 0.2 |
| pCGN4800 | N.D. | N.D. | N.D. | 0.98 | 27.61 | 0.61 | 2.3 | 30.13 | 23.21 | 12.83 | 1.03 | 0.74 | 0.56 |
| pCGN4803 | N.D. | 3.94 | 0.53 | 5.44 | 19.96 | 1.07 | 2.85 | 31.36 | 22.43 | 11.03 | 0.64 | 0.41 | 0.24 |

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

What is claimed is:

1. A recombinant DNA construct comprising an expression cassette that produces a plant acyl-ACP thioesterase in a host cell, wherein said construct comprises, in the 5' to 3' direction of transcription, a transcriptional initiation regulatory region functional in said host cell, a translational initiation regulatory region functional in said host cell, a DNA sequence encoding a biologically active plant thioesterase having which preferentially utilizes C16:0 fatty acyl-ACP substrates as compared to C18:1 fatty acyl-ACP substrates, and a transcriptional and translational termination regulatory region functional in said host cell, wherein said plant thioesterase encoding sequence is under the control of said regulatory regions.

2. The construct of claim 1 wherein said host cell is a plant cell.

3. The construct of claim 2 wherein said transcriptional initiation region is obtained from a gene preferentially expressed in plant seed tissue.

4. The construct of claim 1 wherein said sequence is from *Cuphea hookeriana*, elm, mango or leek.

5. The construct of claim 1 wherein said sequence is from a *Cuphea hookeriana* CUPH-1 thioesterase gene.

6. The construct of claim 1 wherein said DNA sequence encodes a *Cuphea hookeriana* thioesterase having the amino acid sequence shown in FIG. 7 (SEQ ID NO:7).

7. The construct of claim 6 wherein said DNA sequence comprises the *Cuphea hookeriana* thioesterase encoding sequence shown in FIG. 7 ( SEQ ID NO: 7).

8. The construct of claim 1 wherein said DNA sequence encodes an elm thioesterase having the amino acid sequence shown in FIG. 8 (SEQ ID NO:29).

9. The construct of claim 8 wherein said DNA sequence comprises the elm thioesterase encoding sequence shown in FIG. 8 (SEQ ID NO:8).

10. The construct of claim 1 wherein said DNA sequence encodes a leek thioesterase having the amino acid sequence shown in FIG. 3 (SEQ ID NO:24).

11. The construct of claim 10 wherein said DNA sequence comprises the leek thioesterase encoding sequence shown in FIG. 3 (SEQ ID NO:3).

12. The construct of claim 1 wherein said DNA sequence encodes a leek thioesterase having the amino acid sequence shown in FIG. 4 (SEQ ID NO:25).

13. The construct of claim 12 wherein said DNA sequence comprises the leek thioesterase encoding sequence shown in FIG. 4 (SEQ ID NO:4).

14. The construct of claim 1 wherein said DNA sequence encodes a mango thioesterase having the amino acid sequence shown in FIG. 2 (SEQ ID NO:23).

15. The construct of claim 14 wherein said DNA sequence comprises the mango thioesterase encoding sequence shown in FIG. 2 (SEQ ID NO:2).

16. The construct of claim 1 wherein said DNA sequence encodes a mango thioesterase having the amino acid sequence shown in FIG. 12 ( SEQ ID NO: 33).

17. The construct of claim 16 wherein said DNA sequence comprises the mango thioesterase encoding sequence shown in FIG. 12 ( SEQ ID NO: 12).

18. The construct of claim 3 wherein said gene preferentially expressed in plant seed tissue is a napin gene.

19. The construct of claim 1 wherein said construct further comprises a T-DNA border element.

20. A host cell transformed with the recombinant DNA construct of any one of claims 1–5.

21. The cell of claim 20 wherein said cell is a plant cell.

22. The cell of claim 21 wherein said plant cell is a Brassica plant cell.

23. A transformed host cell comprising an expressed plant thioesterase which preferentially utilizes C16:0 fatty acyl-ACP substrates as compared to C18:1 fatty acyl-ACP substrates.

24. The cell of claim 23 wherein said host cell is a plant cell.

25. A plant cell transformed with a DNA construct, said construct comprising, in the 5' to 3' direction of transcription as operably linked components, a seed-specific promoter regulatory element, a DNA sequence encoding a plant acyl-ACP thioesterase which preferentially utilizes C16:0 fatty acyl-ACP substrates as compared to C18:1 fatty acyl-ACP substrates, and a transcriptional termination region regulatory element functional in a plant cell, wherein at least one element is heterologous to said plant or to another element of said construct.

26. The plant cell of claim 25 wherein said DNA sequence is from *Cuphea hookeriana*, elm mango or leek.

27. The plant cell of claim 24 or 25 wherein said cell is a Brassica cell.

28. The plant cell of claim 27 wherein said cell is a *Brassica napus* cell.

29. A plant cell comprising a first DNA construct and a second DNA construct,
said first DNA construct comprising, in the 5' to 3' direction of transcription as operably linked components, a seed-specific promoter regulatory element, a DNA sequence encoding a plant acyl-ACP thioesterase which preferentially utilizes C16:0 fatty acyl-ACP substrates as compared to C18:1 fatty acyl-ACP substrates, and a transcriptional termination region regulatory element functional in a plant cell, and
said second DNA construct comprising, in the 5' to 340 direction of transcription as operably linked components, a seed-specific promoter regulatory element, a DNA sequence encoding a plant stearoyl-acyl ACP desaturase element positioned in an anti-sense orientation, and a transcriptional termination region regulatory element functional in a plant cell, wherein said plant stearoyl-acyl ACP desaturase is complementary to an endogenous stearoyl-acyl ACP desaturase of said plant cell.

30. A method of increasing the percentage of C16:0 fatty acids in a plant seed, wherein said method comprises:
growing a plant having integrated into its genome a DNA construct, said construct comprising in the 5' to Y direction of transcription, a transcriptional regulatory region functional in said plant cell and a plant thioesterase encoding sequence, wherein said plant thioesterase is expressed and preferentially utilizes saturated C16:0 fatty acyl-ACP substrates as compared to C18:1 fatty acyl-ACP substrates, and
harvesting seed from said plant, wherein said seed comprises oil having an increased percentage of C16:0 fatty acids as compared to C16:0 fatty acid levels in wild-type seed from an untransformed control plant.

31. The method of claim 30 wherein said plant seed is an oilseed crop plant seed.

32. The method of claim 30 wherein said plant thioesterase encoding sequence is from *Cuphea hookeriana*, elm, mango or leek.

33. The method of claim 30 wherein said plant thioesterase encoding sequence encodes a *Cuphea hookeriana* CUPH-1 thioesterase.

34. A method of producing plant seed triglycerides having an increased proportion of C16:0 fatty acyl groups comprising, growing a transgenic plant to produce seed, wherein said plant comprises a construct according to claim 1.

35. The method of claim 34 wherein said plant is a Brassica plant.

36. The method of claim 35 wherein said Brassica plant is a *Brassica napus* plant.

37. The method of claim 34 wherein said plant acyl-ACP thioesterase active on C16:0-ACP substrate is from leek, mango, *Cuphea hookeriana* or elm.

38. A plant seed having an increased percentage of C16:0 fatty acids as compared to C16:0 fatty acid levels in wild-type seed from an untransformed control plant, wherein said seed is produced according to the method of any one of claims 33–36.

39. The plant seed of claim 38, wherein said plant is Brassica.

40. A plant comprising plant seed according to claim 38.

41. A transgenic *Brassica napus* plant seed comprising a minimum of 20 mole percent palmitate in the storage triglycerides.

42. An oil derived from seed of claim 41.